(12) United States Patent
Hipszer et al.

(10) Patent No.: US 11,065,385 B2
(45) Date of Patent: Jul. 20, 2021

(54) FLUID BOLUS DETECTION

(71) Applicant: Edwards Lifesciences Corporation, Irvine, CA (US)

(72) Inventors: Brian R. Hipszer, Irvine, CA (US); Morgan T. McKeown, Santa Ana, CA (US); Feras Al Hatib, Irvine, CA (US); Peter James Ifft, Lake Forest, CA (US); Geertruida Lucretia Van Der Sar, Alphen aan den Rijn (NL); Peiyuan Li, Amsterdam (NL)

(73) Assignee: Edwards Lifesciences Corporation, Irvine, CA (US)

( * ) Notice: Subject to any disclaimer, the term of this patent is extended or adjusted under 35 U.S.C. 154(b) by 210 days.

(21) Appl. No.: 16/003,498

(22) Filed: Jun. 8, 2018

(65) Prior Publication Data

US 2018/0353683 A1    Dec. 13, 2018

Related U.S. Application Data

(60) Provisional application No. 62/517,040, filed on Jun. 8, 2017, provisional application No. 62/591,900, filed on Nov. 29, 2017, provisional application No. 62/656,511, filed on Apr. 12, 2018.

(51) Int. Cl.
| | | |
|---|---|---|
| *A61M 5/172* | (2006.01) | |
| *A61B 5/07* | (2006.01) | |
| *A61M 5/168* | (2006.01) | |
| *G16H 40/60* | (2018.01) | |
| *A01K 11/00* | (2006.01) | |

(52) U.S. Cl.
CPC ............ *A61M 5/172* (2013.01); *A61B 5/076* (2013.01); *A61M 5/16859* (2013.01); *G16H 40/60* (2018.01); *A01K 11/007* (2013.01)

(58) Field of Classification Search
CPC ............ A61M 5/172; A61M 5/16804; A61M 5/16859; A61M 5/168; A61M 5/16886; A61M 5/16877; A61M 5/16831; A61B 5/03; G16H 40/60; A01K 11/007
See application file for complete search history.

(56) References Cited

U.S. PATENT DOCUMENTS

| | | | |
|---|---|---|---|
| 4,192,303 A | 3/1980 | Young et al. | |
| 4,838,856 A * | 6/1989 | Mulreany | A61M 5/16827 128/DIG. 13 |
| 5,011,477 A | 4/1991 | Winchell et al. | |
| (Continued) | | | |

FOREIGN PATENT DOCUMENTS

| | | | |
|---|---|---|---|
| WO | 2015197397 A1 | 12/2015 | |
| WO | 2017034568 A1 | 3/2017 | |

*Primary Examiner* — Laura A Bouchelle
(74) *Attorney, Agent, or Firm* — David S. Barnhill; Chang & Hale

(57) ABSTRACT

The present disclosure provides systems that include a flow probe that senses fluid flow or mass flow of fluid delivery to a patient. Based at least in part on the sensed fluid or mass flow, the flow probe provides flow-related data (e.g., volume or mass flow rate) that the system uses to derive a volume of fluid being delivered. The fluid can be delivered from an IV bag, another in-line port, or a combination of the two. The disclosed systems provide fluid volume and/or fluid rate for display to a clinician and an informative understanding of what volume of fluid/mass a patient has received.

20 Claims, 26 Drawing Sheets

(56) References Cited

U.S. PATENT DOCUMENTS

| | | | |
|---|---|---|---|
| 5,059,173 A | 10/1991 | Sacco | |
| 5,505,707 A | 4/1996 | Manzie et al. | |
| 5,599,303 A | 2/1997 | Melker et al. | |
| 6,089,103 A | 7/2000 | Smith | |
| 6,981,967 B2 | 1/2006 | Massengale et al. | |
| 7,503,903 B2 | 3/2009 | Carlisle et al. | |
| 7,818,184 B2 | 10/2010 | Penny et al. | |
| 8,372,045 B2 | 2/2013 | Needle et al. | |
| 8,544,815 B2 | 10/2013 | Avery et al. | |
| 8,617,135 B2 | 12/2013 | Rinehart et al. | |
| 8,692,678 B2 | 4/2014 | Warner et al. | |
| 9,132,233 B2 | 9/2015 | Lee | |
| 9,746,093 B2 * | 8/2017 | Peret | G01F 1/661 |
| 2003/0135152 A1 * | 7/2003 | Kollar | A61M 1/3643 604/35 |
| 2003/0153867 A1 | 8/2003 | Grifols Lucas | |
| 2004/0267086 A1 * | 12/2004 | Anstadt | A61M 1/1068 600/17 |
| 2005/0059926 A1 * | 3/2005 | Sage, Jr. | A61M 5/168 604/65 |
| 2007/0255199 A1 * | 11/2007 | Dewey | A61M 5/14224 604/67 |
| 2009/0093774 A1 * | 4/2009 | Wang | A61M 5/142 604/247 |
| 2009/0212966 A1 * | 8/2009 | Panduro | A61M 5/172 340/4.31 |
| 2010/0114027 A1 * | 5/2010 | Jacobson | A61M 5/16886 604/151 |
| 2010/0228100 A1 * | 9/2010 | Vining | A61B 5/036 600/300 |
| 2010/0280486 A1 | 11/2010 | Khair et al. | |
| 2011/0137239 A1 * | 6/2011 | DeBelser | A61M 5/14244 604/67 |
| 2012/0035543 A1 * | 2/2012 | Kamen | A61M 5/1684 604/113 |
| 2012/0065482 A1 * | 3/2012 | Robinson | A61B 5/14532 600/309 |
| 2012/0179007 A1 * | 7/2012 | Rinehart | A61B 5/029 600/301 |
| 2012/0291540 A1 | 11/2012 | Cooke et al. | |
| 2012/0330117 A1 * | 12/2012 | Grudic | A61B 5/02028 600/324 |
| 2013/0211373 A1 * | 8/2013 | Lee | A61M 5/142 604/506 |
| 2013/0310770 A1 | 11/2013 | Cooke et al. | |
| 2013/0310990 A1 * | 11/2013 | Peret | A61M 5/16804 700/282 |
| 2014/0073890 A1 * | 3/2014 | Su | A61B 5/4839 600/324 |
| 2016/0125164 A1 | 5/2016 | Kelly et al. | |

* cited by examiner

FLUID BOLUS DETECTION

CROSS-REFERENCE TO RELATED APPLICATIONS

This application claims the benefit of priority to U.S. Provisional Application No. 62/517,040 filed Jun. 8, 2017 and entitled "ASSISTED FLUID DELIVERY SYSTEM AND METHOD," and to U.S. Provisional Application No. 62/591,900 filed Nov. 29, 2017 and entitled "COMBINING LOW FLOW AND HIGH FLOW IN INTRAVENOUS INFUSION," and to U.S. Provisional Application No. 62/656,511 filed Apr. 12, 2018 and entitled "AUTOMATIC FLUID BOLUS DETECTION," each of which is incorporated by reference in its entirety for all purposes.

BACKGROUND

Field

The present disclosure relates generally to tracking fluid boluses, and more particularly to systems, apparatuses, and methods for prompting, tracking, and displaying information related to delivery of a fluid bolus.

Description of Related Art

Fluid boluses (or fluid challenges) can be used in the fluid management of patients. The principle behind the fluid challenge technique is that by giving a small amount of fluid in a short period of time (e.g., a fluid bolus), the clinician can assess whether the patient has a preload reserve that can be used to increase the stroke volume with further fluids. Continuous cardiac output can be used to monitor a patient's response to a fluid challenge. Therapy guided by determining patients' responses to fluid challenges can lead to reduced hospital stays and fewer postoperative complications.

Physiological indicators such as stroke volume (SV), cardiac output (CO), end-diastolic volume, ejection fraction, stroke volume variation (SVV), pulse pressure variation (PPV), systolic pressure variations (SPV), and plethysmographic variability index (PVI) have been found useful in the assessment of patient status and conditions, particularly in medium to high risk patients undergoing surgery or in the intensive care unit. Many clinicians utilize these parameters to determine how much fluid (or medications) to deliver to their patients, and clinical studies have shown that when used in conjunction with a treatment protocol, these types of parameters guide treatment in a way that improves patient outcomes. For instance, clinicians may give a "fluid challenge," e.g., give the patient a bolus of fluid (ranging from about 200 mL to about 1 L), and observe the corresponding change in the SV. A large change in SV indicates that the patient is "fluid responsive" and may benefit from more fluid; a small change in SV may indicate that the patient is not responsive to fluid and is therefore unlikely to benefit from additional fluid. In spite of their utility, the application of these parameters and protocols has been limited due at least in part to difficulties in tracking the amount of fluid or medication corresponding to the physiological change in the parameters. Highly skilled and/or well-trained clinicians can manually keep track of the timing/rate/amount of the fluids/medication and match it to the corresponding change in physiological parameters, however, the process is tedious and prone to error. Thus, only the most highly skilled, well-trained, and patient clinicians can maintain a high compliance rate to desired treatment protocols.

Software in conventional monitoring systems has attempted to simplify this process by providing calculations and recommendations. However, typical monitoring systems are not configured or equipped for determining or measuring all the fluids and/or medications that are delivered to the subject (e.g., fluid and/or medication delivered through multiple delivery devices simultaneously, concurrently, or intermittently). While in theory this could be accomplished by a clinician manually entering the relevant information, such a process is time-consuming, tedious, and prone to human error.

While methods of precisely tracking fluid using a conventional fluid infusion pump exist, in practice such equipment and methods have proven sub-optimal for various reasons, including that the information from conventional fluid infusion pumps is not connected to physiological monitors, so the calculations, tracking, and comparisons still require significant manual input. Furthermore, standard fluid infusion pumps generally have a fluid delivery limitation of around 1 L/hr, which may be slower than a desired infusion rate. In addition, there are infusion pumps on the market that limit and/or slow integration with existing, commercially-installed monitor base systems. Moreover, conventional systems are typically not configured or equipped for determining or measuring all the fluid that is being delivered to the subject (e.g., fluid delivered through multiple delivery devices simultaneously, concurrently, or intermittently).

Thus, even if healthcare providers desire implementation of a protocolized approach to fluid and/or medication delivery, they are left with sub-optimal options. Currently, there is no easy method of comparing the amount of fluid and/or medication given a patient and the corresponding change in physiological parameters resulting therefrom to implement a robust protocolized approach to fluid and/or medication delivery optimization.

SUMMARY

In a first aspect, the present disclosure relates to a method that includes receiving electronically from a flow probe flow-related data for fluid administered to a subject. The method also includes calculating, using a processor, using the flow-related data, a subsequent administration protocol. The method also includes generating a recommendation corresponding to the subsequent administration protocol.

In some embodiments of the first aspect, the recommendation is provided by a user-interactive graphical user interface (GUI), alphanumeric text, or audible language. In some embodiments of the first aspect, the method further includes receiving electronically from a physiological sensor physiological data of a subject; correlating, using the processor, the physiological data and the flow-related data; and generating the subsequent administration protocol based at least in part on the correlation. In some embodiments of the first aspect, the method further includes controlling subsequently administered fluid to the subject based on the subsequent administration protocol, wherein controlling the fluid is accomplished using a flow controller.

In some embodiments of the first aspect, the method further includes determining a first effect on a physiological state of the subject associated with the flow-related data; storing in a device storage operatively coupled to the processor first administration-related data relating to the first effect; and generating, using the processor, a first subsequent administration protocol based upon the first administration-related data. In further embodiments of the first aspect, the method further includes determining, using the processor, a second effect on the physiological state of the subject associated with administration to the subject of a second fluid administration corresponding to a second flow-related data; storing in the device storage second administration-related data relating to the second effect; and generating, using the processor, a second subsequent administration protocol based upon the second administration-related data and the first administration-related data.

In some embodiments of the first aspect, the method further includes administering the fluid to the subject via a gravity-assisted fluid-delivery system. In some embodiments of the first aspect, the fluid comprises medication to alter or maintain a physiological state of the subject.

In a second aspect, the present disclosure relates to a computer-implemented method for assisting administration of fluid to a subject, the method includes determining, using a processor, a first effect on a sensed physiological parameter of the subject associated with a first administration event under a first administration condition. The method also includes storing, using the processor, first administration-related data relating to the first effect corresponding to the first administration condition. The method also includes determining, using the processor, a subsequent administration protocol based at least in part upon the first administration-related data. The method also includes generating a recommendation as to the subsequent administration protocol.

In some embodiments of the second aspect, the recommendation is provided by a user-interactive graphical user interface (GUI), alphanumeric text, or audible language. In some embodiments of the second aspect, the method further includes determining, using the processor, a second effect on the sensed physiological parameter of the subject associated with a second administration event under a second administration condition; storing, using the processor, second administration-related data relating to the second effect corresponding to the second administration condition; and generating, using the processor, a second subsequent administration protocol based at least in part upon the second administration-related data and the first administration-related data.

In a third aspect, the present disclosure relates to a method includes receiving sensed administration-related data corresponding to an administration event for a subject. The method also includes determining, using a processor, a current physiological state of the subject based at least in part upon the sensed administration-related data. The method also includes calculating, using the processor and an algorithm, a recommendation regarding an amount or rate of fluid to be subsequently administered to the subject based at least in part upon the sensed administration-related data and the current physiological state of subject.

In some embodiments of the third aspect, the recommendation is provided by a user-interactive graphical user interface (GUI), alphanumeric text, or audible language. In some embodiments of the third aspect, the method further includes, based on the recommendation, sending a fluid administration signal to a flow controller that is configured to control an amount of fluid administered to the subject. In some embodiments of the third aspect, the method further includes receiving second sensed administration-related data corresponding to a second administration event; determining, using the processor, a second physiological state of the subject based at least in part upon the second administration-related data; and generating, using the processor, a second subsequent administration protocol based at least in part upon the second administration-related data, the second administration-related data, and the first administration-related data.

In a fourth aspect, the present disclosure relates to a system for managing a hemodynamic state of the subject, the system includes a hemodynamic data sensor configured to sense hemodynamic data of a subject and to provide sensed hemodynamic data. The system also includes a flow probe configured to measure a flow-related data of a fluid configured to alter or maintain a hemodynamic state of a subject and to provide the measured flow-related data. The system also includes a flow controller configured to control a flow of the fluid administered to the subject. The system also includes system electronics configured for communication with the flow probe, the hemodynamic data sensor, and the flow controller. The system also includes a monitor adapted for signal communication with the system electronics or a display. The system also includes a storage device comprising computer program code configured such that, when operated on by one or more processors, causes the one or more processors to perform receiving and/or transmitting of signals between one or more of the flow probe, the hemodynamic data sensor, the flow controller, and the monitor.

In some embodiments of the fourth aspect, the computer program code performs the following operation: sensing data from a physiological sensor sensing one or more dynamic physiological parameter values corresponding to a first physiological parameter state, the physiological sensor communicatively coupled to the system electronics; sensing a fluid flow rate from a flow probe; correlating the dynamic physiological parameters with the fluid flow rate using the processor; and providing a signal to the flow controller to adjust a fluid flow rate to the subject to cause a change in the physiological state of the subject.

In some embodiments of the fourth aspect, the computer program code is further configured to perform the following operations: providing, for display on a monitor, and administration recommendation configured to cause an adjustment of the fluid flow rate or an amount of fluid administered to the subject to change the hemodynamic state of the subject. In some embodiments of the fourth aspect, the fluid flow rate is dynamically measured.

In a fifth aspect, the present disclosure relates to a monitor for tracking a fluid bolus, the monitor includes a display, a memory, and a processor connected to the display and to the memory. The processor is configured to execute instructions that cause the monitor to receive flow-related data from a flow probe; detect initiation of a fluid bolus based at least in part on the received flow-related data; display a prompt on the display indicating that the fluid bolus has started, the prompt including real-time flow-related data received from the flow probe; and detect termination of the fluid bolus based at least in part on the received flow-related data.

In some embodiments of the fifth aspect, the processor is further configured to display hemodynamic parameters received from a hemodynamic sensor. In some embodiments of the fifth aspect, the processor is further configured to send a signal to a flow controller to cause the flow controller to initiate a fluid bolus. In some embodiments of the fifth aspect, the processor is further configured to receive input based on a user interaction with the first prompt declining the suggestion to initiate a fluid bolus. In some embodiments of the fifth aspect, the processor is further configured to receive input based on a user interaction with the third prompt discarding the flow-related data determined for the fluid bolus.

In some embodiments of the fifth aspect, the processor is further configured to receive input based on a user interaction with the third prompt accepting the flow-related data determined for the fluid bolus. In some embodiments of the fifth aspect, the display includes elements that display hemodynamic parameters measured by a hemodynamic sensor. In some embodiments of the fifth aspect, the processor is further configured to execute the instructions without receiving input from a user. In some embodiments of the fifth aspect, the processor is configured to determine that the fluid bolus is desirable is based at least in part on measured hemodynamic parameters or flow-related data. In some embodiments of the fifth aspect, the processor is configured to determine that the fluid bolus has started based at least in part on a flow rate exceeding a programmed threshold.

In some embodiments of the fifth aspect, the processor is further configured to determine that a fluid bolus is desirable. In further embodiments of the fifth aspect, the processor is further configured to display a first prompt on the display indicating that a fluid bolus is suggested.

In some embodiments of the fifth aspect, the processor is further configured to display a second prompt on the display indicating that the fluid bolus has ended, the second prompt including flow-related data determined for the fluid bolus.

In a sixth aspect, the present disclosure relates to a method for automatically detecting and tracking a fluid bolus, the method includes receiving flow-related data from a flow probe. The method also includes detecting initiation of a fluid bolus based at least in part on the received flow-related data. The method also includes displaying a second prompt on the display indicating that the fluid bolus has started, the second prompt including real-time flow-related data received from the flow probe. The method also includes detecting termination of the fluid bolus based at least in part on the received flow-related data.

In some embodiments of the sixth aspect, the method further includes displaying hemodynamic parameters received from a hemodynamic sensor. In some embodiments of the sixth aspect, the method further includes sending a signal to a flow controller to cause the flow controller to initiate a fluid bolus. In some embodiments of the sixth aspect, the method further includes receiving input based on a user interaction with the first prompt declining the suggestion to initiate a fluid bolus. In some embodiments of the sixth aspect, the method further includes receiving input based on a user interaction with the third prompt discarding the flow-related data determined for the fluid bolus. In some embodiments of the sixth aspect, the method further includes receiving input based on a user interaction with the third prompt accepting the flow-related data determined for the fluid bolus.

In some embodiments of the sixth aspect, the method further includes displaying hemodynamic parameters measured by a hemodynamic sensor. In further embodiments of the sixth aspect, the method executes without receiving input from a user.

In some embodiments of the sixth aspect, determining that the fluid bolus is desirable is based at least in part on measured hemodynamic parameters or flow-related data. In some embodiments of the sixth aspect, determining that the fluid bolus has started is based at least in part on a flow rate exceeding a programmed threshold.

In some embodiments of the sixth aspect, the method further includes determining that a fluid bolus is desirable. In further embodiments of the sixth aspect, the method further includes displaying a second prompt on the display indicating that a fluid bolus is suggested.

In some embodiments of the sixth aspect, the method further includes displaying a second prompt on the display indicating that the fluid bolus has ended, the second prompt including flow-related data determined for the fluid bolus.

In a seventh aspect, the present disclosure relates to a flow controller providing a high flow state and a low flow state, the flow controller includes an input port, an output port, and an internal conduit coupled to the input port and to the output port, the internal conduit being partitioned into a high flow path and a low flow path between the input port and the output port. The flow controller also includes a valve positioned at the high flow path, the valve configured to fully open in the high flow state and to fully close in the low flow state to provide a first flow rate in the high flow state that is higher than a second flow rate in the low flow state.

In some embodiments of the seventh aspect, the first flow rate is at least 100 times the second flow rate. In some embodiments of the seventh aspect, the low flow path comprises a separate conduit from the high flow path. In further embodiments of the seventh aspect, the conduit of the low flow path is releasably coupled to the internal conduit, allowing for conduits of different sizes to be used for the low flow path.

In some embodiments of the seventh aspect, an inner diameter of the low flow path is configured to provide a targeted low flow rate in the low flow state. In further embodiments of the seventh aspect, an inner diameter of the high flow path is configured to provide a targeted high flow rate in the high flow state.

In some embodiments of the seventh aspect, the first flow rate is a combination of a flow rate through the high flow path and a flow rate through the low flow path.

In an eighth aspect, the present disclosure relates to a flow controller providing a high flow state and a low flow state, the flow controller includes a conduit configured to receive a liquid from a fluid source and to deliver the liquid to a subject. The flow controller also includes a valve coupled to the conduit, the valve configured to be positioned in a first position to provide the high flow state and in a second position to provide the low flow state, the second position configured to constrict the conduit to provide an uninterrupted low flow rate through the conduit.

In some embodiments of the eighth aspect, the flow rate of the high flow state is at least 100 times the flow rate of the low flow state.

In some embodiments of the eighth aspect, the valve comprises a pinch valve that constricts the conduit in a de-energized state. In further embodiments of the eighth aspect, the pinch valve does not constrict the conduit in an energized state.

In some embodiments of the eighth aspect, the second position is configured to constrict the conduit so that a cross-section of the constricted conduit is configured to provide a targeted low flow rate. In some embodiments of the eighth aspect, a flow rate in the high flow state is at least 1 L/hr and the flow rate in the low flow state is less than or equal to 100 mL/hr.

In a ninth aspect, the present disclosure relates to a flow controller providing a high flow state and a low flow state, the flow controller includes a conduit configured to receive a liquid from a fluid source and to deliver the liquid to a subject, the conduit having a partition dividing the conduit into a high flow path and a low flow path. The flow controller also includes a switch positioned within the conduit at the partition, the switch configured to be positioned in a first position to block the low flow path to provide the high flow state and in a second position to block the high flow path to provide the low flow state.

In some embodiments of the ninth aspect, the cross-section of the low flow path is configured to provide a targeted low flow rate. In some embodiments of the ninth aspect, the cross-section of the high flow path is configured to provide a targeted high flow rate. In some embodiments of the ninth aspect, the flow rate of the high flow state is at least 100 times the flow rate of the low flow state. In some embodiments of the ninth aspect, the switch is only in a steady state in the first position or in the second position.

In a tenth aspect, the present disclosure relates to a method for providing a high flow state and a low flow state for a flow of liquid from a fluid source to a subject, the method includes receiving an electronic signal corresponding to the high flow state. The method also includes manipulating a mechanical component coupled to a conduit to provide a high flow rate through the conduit. The method also includes receiving an electronic signal corresponding to the low flow state. The method also includes manipulating the mechanical component coupled to the conduit to provide a low flow rate through the conduit, the high flow rate being at least 100 times the low flow rate.

In some embodiments of the tenth aspect, the mechanical component comprises a valve that at least partially restricts the conduit in the low flow state. In some embodiments of the tenth aspect, the mechanical component comprises a switch that blocks a high flow path through the conduit in the low flow state. In further embodiments of the tenth aspect, the switch blocks a low flow path through the conduit in the high flow state. In further embodiments of the tenth aspect, the switch opens the high flow path through the conduit in the high flow state so that the high flow rate is a combination of a flow rate through the high flow path and a flow rate through the low flow path.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1A:
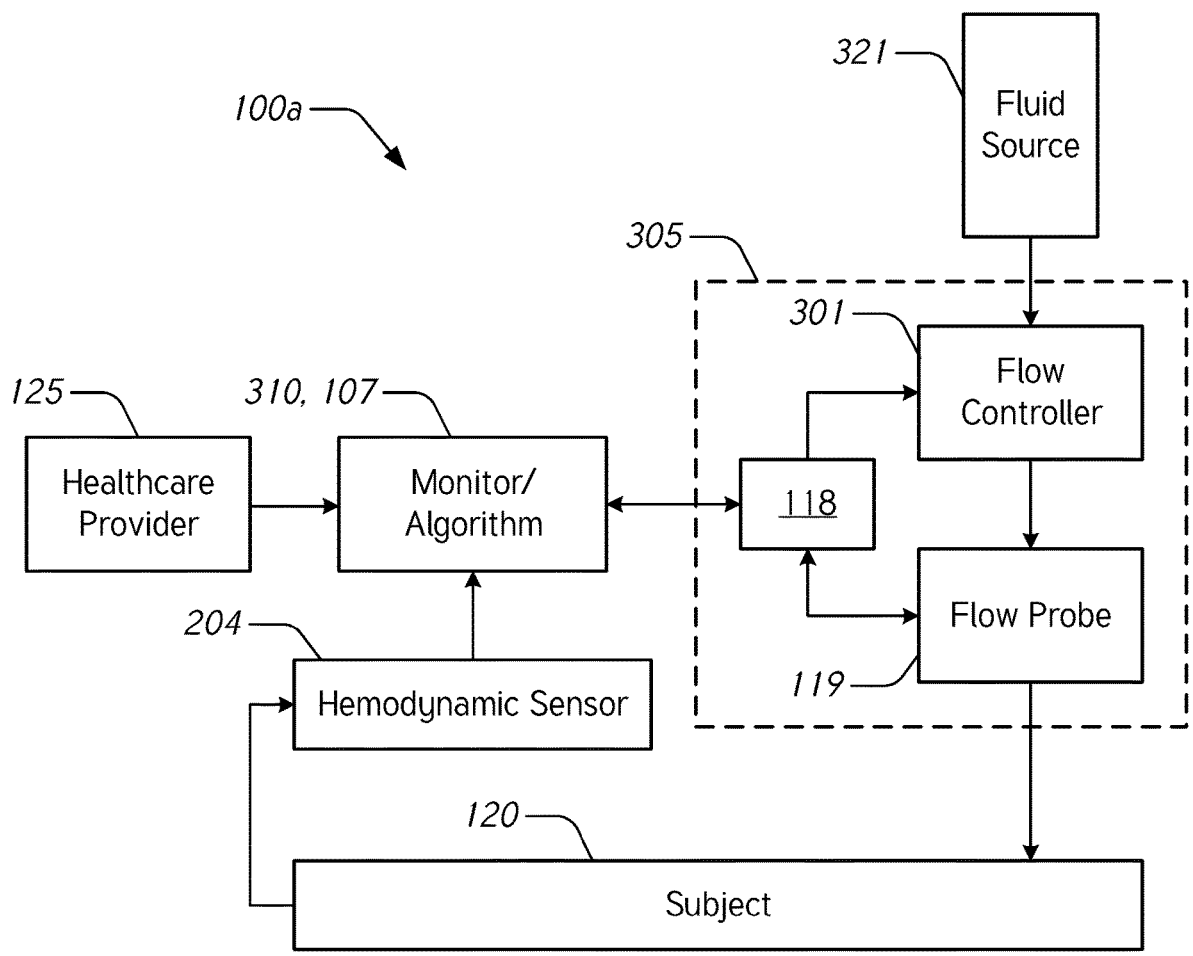
FIG. 1A is a schematic flow diagram of an example subject monitoring system.

The headings provided herein are for convenience only and do not necessarily affect the scope or meaning of the claimed embodiments.

Overview

During intravenous (IV) infusion, there are situations where it is advantageous to deliver a fluid bolus to determine a patient's fluid responsiveness. For example, by giving a small amount of fluid in a short period of time (e.g., a fluid bolus), the clinician can assess whether the patient has a preload reserve that can be used to increase the stroke volume with further fluids. Typically, fluid challenges are administered by a healthcare professional who manually tracks the amount of fluid. Manually tracking these boluses can be tedious and prone to error. When a bolus is not being delivered, it may be desirable to provide a constant or uninterrupted flow of liquid at a relatively low flow rate (e.g., between about 10 mL/hr and about 60 mL/hr) to prevent or reduce blood clot formation at the cannula insertion site.

Accordingly, to address these and other issues, disclosed herein are devices, systems, and methods that automate the identification of the start and end of a fluid bolus and calculate the volume of fluid given during the challenge. A flow measurement device is used to measure fluid flow in a conduit (e.g., IV tubing) and an algorithm is used to determine a start time and the stop time of a fluid bolus. In addition, the volume of fluid given during the bolus is calculated. Advantageously, this provides accurate and automatic collection of the start time of the fluid bolus, the income of the fluid bolus, and the volume of the fluid bolus. Historically, these data are estimated by the clinician used to assess the hemodynamic response to the fluid bolus.

The disclosed devices, systems, and methods use a flow measurement device such as a flow sensor. The flow sensor is configured to determine a flow rate and/or volume of fluid through the conduit (e.g., IV tubing). This flow rate measurement can be used to determine initiation and termination of a fluid bolus, instantaneous flow rates, and fluid volumes over a given period of time.

The disclosed devices, systems, and methods display a user interface that suggests delivery of a fluid bolus to a clinician. The display also indicates detection of initiation of the fluid bolus, flow rate, duration, total volume delivered, and the like. The display also indicates detection of termination of the fluid bolus and can display the determined start time, end time, and volume delivered of the fluid bolus. In some embodiments, the clinician can decline the suggested delivery of the bolus and/or can accept the measured values displayed on the display. In some embodiments, the delivery of a suggested bolus can be done without the clinician providing input to the user interface.

In addition, to address these and other issues, disclosed herein are devices, systems, and methods that control liquid in intravenous (IV) infusion, providing a high flow state to deliver a fluid bolus and a low flow state to provide an uninterrupted flow of liquid to the subject. As described herein, there are situations where it is advantageous to provide a bolus of fluid, corresponding to a relatively high flow rate, and when a bolus is not being delivered it is desirable to provide an uninterrupted low flow. Accordingly, the devices and methods are directed to providing an uninterrupted low flow in the IV line to keep the line open and a device (e.g., a valve) to control flow at a higher targeted rate for bolus delivery.

The disclosed devices, systems, and methods use a flow controller operable in two states: a high flow state and a low flow state. The flow controller includes a mechanical component that is configured to switch between the two states. The mechanical component can be configured to be controlled using an electrical signal or it can be operated manually. The mechanical component can manipulate the conduit itself and/or redirect liquid flow to one or more paths to operate in the high flow state and/or the low flow state.

In some embodiments, the mechanical component is a pinch valve that can be positioned in a low flow position that restricts the size of the conduit to provide a targeted low flow rate and in a high flow position that does not restrict the size of the conduit or that restricts the size of the conduit to provide a targeted high flow rate. The pinch valve can be positioned in one of the two positions so that, at a minimum, the flow controller is configured to provide a targeted low flow rate.

In some embodiments, the flow controller provides a low flow conduit having a cross-section configured to provide a targeted low flow rate and a high flow conduit having a cross-section configured to provide a targeted high flow rate or to provide a flow rate that is larger than the targeted low flow rate. The flow controller includes a pinch valve as the mechanical component, the pinch valve being coupled to the high flow conduit. In the low flow state, the pinch valve is configured to close or pinch the high flow conduit to prevent liquid flow through the high flow conduit. This leaves the low flow conduit open to provide the targeted low flow rate. In the high flow state, the pinch calve is configured to open so that liquid flows freely through the high flow conduit. Thus, the high flow rate provided in the high flow state is a combination of the flow rate through the high flow conduit and the flow rate through the low flow conduit.

In some embodiments, the flow controller includes a valve as the mechanical component, the valve being positioned in a conduit that is divided immediately downstream of the valve. In a low flow state, the valve is positioned in a low flow position to direct liquid to a low flow portion of the divided portion of the conduit. In the high flow state, the valve is positioned in a high flow position to direct liquid to a high flow portion of the divided portion of the conduit. The valve is configured to be positioned in one of the two positions to provide the targeted low flow rate or the high flow rate.

In addition, the present disclosure provides systems that include a flow probe that senses fluid flow or mass flow of fluid delivery to a patient. Based at least in part on the sensed fluid or mass flow, the flow probe provides flow-related data (e.g., volume or mass flow rate) that the system uses to derive a volume of fluid being delivered. The fluid can be delivered from an IV bag, another in-line port, or a combination of the two. Briefly, and as further described below, the disclosed systems provide fluid volume and/or fluid rate for display to a clinician and an informative understanding of what volume of fluid/mass a patient has received. This system finds applicability in determining an amount of fluid delivered, and may be applicable without any flow controlling device or means.

The disclosed systems can include a flow probe, a physiological sensor, and a monitor (and an algorithm) with a graphical user interface (GUI). The flow probe can be configured to sense flow-related information in combination with sensed physiological data from the physiological sensor. In such embodiments, the physiological sensor information can be utilized along with the fluid delivery related data (e.g., provided by the flow probe) to assess the effect of the fluid delivery on the physiology and generate a recommendation to the clinician of subsequent administration protocol(s) that can include a targeted flow rate and volume amounts and/or adjustments to the flow rate and/or volume. In certain implementations, no actual mechanism, device, or recommended method of how to administer that fluid is provided. Thus, in such implementations, it is in the discretion of the clinician to control the subsequent administration of fluid based on the recommendation provided by the system.

In some embodiments, the disclosed systems include a flow probe and a physiological sensor that provides physiological data to an algorithm. The algorithm utilizes the flow related information from the flow probe and the physiological sensor data to provide a recommendation to the clinician (e.g., via a GUI) regarding subsequent administration protocol(s) that can include flow rate and volume amounts and/or adjustments. The disclosed systems can further include a flow controller associated with the source of fluid that is manually manipulated to vary fluid delivery rate and, by extension, the volume of fluid delivered. The flow controller can be configured to be controlled by the clinician manually. The actual physical control of fluid administered could be a standard IV roller clamp, for example. Such manual control of fluid delivery may be part of a standard IV tubing set that can be connected and/or adapted to the disclosed systems. Thus, it is in the discretion of the clinician to control the subsequent administration of fluid based on the recommendation provided by the system.

In some embodiments, the disclosed systems include a flow rate sensor and a physiological sensor that provides physiological data to an algorithm. The algorithm utilizes the flow related information and the physiological sensor data to provide subsequent administration protocol(s) that can include flow rate and volume amounts and/or adjustments. The disclosed systems further include a flow controller, associated with the source of fluid, that is automatically manipulated by the system to vary fluid delivery rate and, by extension, the volume of fluid delivered. Although the flow controller of the system is configured to be controlled essentially automatically by the algorithm, an ability to override the algorithm and its administration protocol by the clinician is provided.

The physiological sensor of the presently disclosed system includes a hemodynamic sensor, such as the FLOTRAC® sensor, configured to provide information capable of being transformed into one or more forms of heart output data. In some embodiments, an oximetry device can be used as the hemodynamic sensor. In certain embodiments, the oximetry device is a finger cuff device that is integrated with the system, the system electronics, and/or the monitor or algorithm. The disclosed systems can utilize an algorithm for determining how the patient responds to certain administered fluid volumes and rates of fluid administration. Based at least in part on the correlated sensed data from the flow probe and the data from the hemodynamic sensor to that of the patient response, the algorithm can provide information to the clinician regarding subsequent bolus administration and/or control (e.g., through the monitor) the amount and/or rate of fluid delivered to the patient by controlling the flow controller.

The terms "subject" and "patient" are used interchangeably herein and relate to mammals, inclusive of warm-blooded animals (domesticated and non-domesticated animals), and humans. The terms "clinician" and "healthcare provider" are used interchangeably herein.

The phrase "vascular access device" as used herein relates to any device that is in communication (or contact) with the vascular system of a subject. Vascular access devices include but are not limited to catheters, shunts, blood withdrawal devices, connectors, fluid couplers, valves, tubing and the like.

The term "sensor" as used herein relates to a device, component, or region of a device capable of detecting and/or quantifying and/or qualifying a physiological parameter of a subject. The phrase "system" as used herein relates to a device, or combination of devices operating at least in part in a cooperative manner, that is inclusive of the "sensor." Sensors generally include those that continually measure the physiological parameter without user initiation and/or interaction ("continuous sensing device" or "continuous sensor"). Continuous sensors include devices and monitoring processes wherein data gaps can and/or do exist, for example, when a continuous pressure sensor is temporarily not providing data, monitoring, or detecting. In some implementations, sensor or continuous sensing device relates to a device, component, or region of a device capable of detecting and/or quantifying and/or qualifying a physiological hemodynamic parameter of a subject.

The phrases "physiological data," "physiological parameter," and/or "hemodynamic parameter" include without limitation, parameters directly or indirectly related to providing or calculating stroke volume (SV), cardiac output (CO), end-diastolic volume, ejection fraction, stroke volume variation (SVV), pulse pressure variation (PPV), systolic pressure variations (SPV), extravascular lung water index (ELWI), pulmonary vascular permeability index (PVPI), global end-diastolic index (GEDI), global ejection fraction (GEF), systolic volume index (SVI), arterial blood pressure (ABP), cardiac index (CI), systemic vascular resistance index (SVRI), peripheral resistance (PR), central venous saturation (ScvO2), and plethysmographic variability index (PVI). Hemodynamic parameters are inclusive of the absolute value of such parameters, a percentage change or variation in the parameters since an event was recorded, and an absolute percentage change within a previous time segment.

The term or phrase "coupling" and "operatively coupling" as used herein relate to a joining or linking together of two or more things, such as two parts of a device or two devices, such that the things can function together. In one example, two devices can be operatively coupled by tubing, such that fluid can flow from one device to another. Coupling does not imply a physical connection. For example, a transmitter and a receiver can be operatively coupled by radio frequency (RF) transmission/communication.

The phrases "electronic connection," "electrical connection," "electrical contact" as used herein relate to any connection between two electrical conductors known to those in the art. In one embodiment, electrodes are in electrical connection with (e.g., electrically connected to) the electronic circuitry of a device.

The term and phrase "electronics" and "system electronics" as used herein relate to electronics operatively coupled to the sensor and configured to measure, process, receive, and/or transmit data associated with a sensor, and/or electronics configured to communicate with a flow controller and to control/monitor fluid metering by the flow controller.

The phrase "fluid communication" as used herein relates to two or more components (e.g., things such as parts of a body or parts of a device) functionally linked such that fluid can move from one component to another without limit to or implication of directionality unless stated.

The phrases "operatively connected," "operatively linked," "operably connected," and "operably linked" as used herein relate to one or more components linked to one or more other components, such that a function is enabled. The terms can refer to a mechanical connection, an electrical connection, or any connection that allows transmission of signals between the components. For example, one or more transducers can be used to detect pressure and to convert that information into a signal; the signal can then be transmitted to a circuit. In such an example, the transducer is "operably linked" to the electronic circuitry. The terms "operatively connected," "operatively linked," "operably connected," and "operably linked" include wired and wireless connections.

The term "monitor" as used herein as a noun, refers to a device configured to observe, record, oversee, detect, supervise, regulate, receive, and/or transmit one or more signals, operations or conditions over a fixed, intermittent, or continuous period of time, for example, signals from a flow probe or hemodynamic sensor. The monitor can include a display for presenting data or other information. The monitor can include one or more processors or processing modules.

The term "display" as used herein as a noun, refers to a device configured to provide a visual representation of data (e.g., text and/or graphics and/or symbols) or any other information from a processor, computer, or monitor.

The term and phrase "processor" or "processing module," as used herein relates to components and the like designed to perform arithmetic or logic operations using logic circuitry that responds to and processes basic instructions, for example, instructions that drive a computer and/or perform calculations of numbers or their representation (e.g., binary numbers).

The terms "substantial" and "substantially" as used herein relate to a sufficient amount that provides a desired function. For example, an amount greater than 50 percent, an amount greater than 60 percent, an amount greater than 70 percent, an amount greater than 80 percent, or an amount greater than 90 percent.

Embodiments of the disclosure include closed-loop systems and/or partial closed-loop systems for fluid management that establish communication between a monitor and a source of liquid infusate. The present systems, apparatus, apparatuses, and methods can provide assisted automated delivery of fluid. Assisted automated delivery of fluid, or assisted fluid delivery, can be based on a determination of delivered fluid volume. In some implementations, assisted automated delivery of fluid, or assisted fluid delivery, can be based on determined delivered fluid volume in combination with optimization of physiological hemodynamic parameters. The present systems can be configured to determine total fluid delivered by all sources of infusion, e.g., whether delivered by an infusion pump and/or IV bag or other means of fluid administration. The present systems provide for a reduction in the burden placed on a clinician, provide for standardize care, and/or improve or optimize clinical outcomes.

The present apparatuses, systems and methods overcome significant limitations of conventional systems. The present system can be configured to operate using an infusion rate obtained by gravity assist. This can include, for example, a flow rate of about 6 L/hr, e.g., an infusion rate corresponding to a 100 mL bolus delivered in 1 minute. The present system can be also configured for use with a separate fluid delivery device with an infusion rate of about 10 L/hr, 8 L/hr, 6 L/hr, 5 L/hr, 4 L/hr, 3 L/hr, or 2 L/hr. The disclosed systems can be readily interchangeable and integrated with previously installed base systems (e.g., agnostic to any infusion pump or other fluid delivery method mechanism). In addition, the acquisition of total fluid volumes of all fluid delivered to the subject are provided, regardless of the mode of infusion (e.g., pump or IV-bag). Moreover, the disclosed systems provide for methods of obtaining and exploiting hemodynamic parameter related infusion events, among other physiological parameters. In some implementations, the disclosed systems provide for methods of obtaining and exploiting hemodynamic parameter related infusion events, among other physiological parameters occurring as a result of an infusion event at an infusion rate of about 1 L/hr to about 10 L/hr, about 0 L/hr to about 10 L/hr, about 1.5 L/hr to about 8 L/hr, or 2 L/hr to about 6 L/hr.

In some implementations, the disclosed systems are devoid of any primary infusion means not otherwise capable of infusing fluid to a subject at a rate of greater than 2 L/hr, such as for example, conventional infusion pumps. To be clear, such conventional infusion pumps may be used in combination with the presently disclosed infusion source, for example, to administer medicament to the subject.

Hemodynamic parameter data obtained by the hemodynamic sensor includes, for example, blood pressure parameters and blood pressure waveform information either in analog or digital form. From such blood pressure parameters, stroke volume variation (SVV), pulse pressure variation (PPV), systolic pressure variation (SPV), and plethysmographic variability index (PVI) can be calculated or derived and displayed.

The disclosed systems include programming, for example, in the form of one or more algorithms, configured to diagnose a condition of the subject using the combination of HD-sensor data and flow probe data and corresponding subject responsiveness to infusion events. The systems can be configured to intermittently or continuously determine at least some hemodynamic information (e.g., stroke volume (SV), cardiac output (CO), end-diastolic volume, ejection fraction, stroke volume variation (SVV), pulse pressure variation (PPV), systolic pressure variations (SPV), plethysmographic variability index (PVI), and/or the like). For example, the system can be configured to make such determinations responsive to the HD-sensor sending hemodynamic data and/or the flow probe sending time-related mass flow volume or rate data to the system electronics.

Thus, in some embodiments, the disclosed systems include a hemodynamic sensor (e.g., a FLOTRAC™ sensor and/or a CLEARSIGHT™ sensor provided by Edwards Lifesciences located in Irvine Calif.) that provides one or more hemodynamic parameter dependent signals or data of a subject to a monitor having an algorithm that utilizes the hemodynamic parameter data, and a flow probe that measures an amount of fluid infused into the subject and an algorithm that utilizes the flow-related data. The algorithms provide recommendations to a health care provider based on the received hemodynamic parameter data and the received flow probe data. The healthcare provider can be presented with a recommendation to infuse fluid, to alter an infusion rate, or to terminate infusion to the subject to adjust or otherwise manipulate one or more hemodynamic parameters. The recommendation can be based on a combination of the flow probe data and the hemodynamic parameter data.

In some embodiments, the disclosed systems include a hemodynamic sensor and a flow probe. In such embodiments, the system provides one or more hemodynamic parameter dependent signals or data of a subject to an algorithm that utilizes the hemodynamic parameter data in combination with a flow probe that measures an amount or rate of fluid infused into the subject and provides one or more administration-related signals or data of the infusion to the algorithm. The algorithm is configured to provide recommendations to a health care provider to infuse or not to infuse fluid to the subject based on the received hemodynamic parameter data and the received flow probe data. The healthcare provider can be presented with a recommendation as to whether or not to accept the prompts relating to recommended administration protocols determined by the algorithms (e.g., the prompts can include recommendations to infuse fluid, to alter an infusion rate, or to terminate infusion to the subject). Upon accepting the recommendation, the system provides one or more signals to a flow controller to adjust or to otherwise manipulate the infusion rate and to manage one or more hemodynamic parameters based on a combination of the flow probe data and the hemodynamic parameter data.

In some embodiments, the disclosed systems include a hemodynamic sensor and a flow probe. The hemodynamic sensor provides one or more hemodynamic parameter dependent signals or data to a monitor having an algorithm that utilizes the hemodynamic parameter data. The flow probe is coupled to a gravity-feed IV bag and measures an amount of fluid infused into the subject and/or provides mass flow information to the algorithm. The algorithm can be configured to provide recommendations to a health care provider based on the combination of the received hemodynamic parameter data and the received flow probe data. The healthcare provider can then be presented with a recommendation to infuse fluid, to alter an infusion rate, or to terminate infusion to the subject to adjust or to otherwise manipulate one or more hemodynamic parameters based on a combination of the flow probe data and the hemodynamic parameter data. In some implementations, the system is configured to operate with an IV bag capable of infusing fluid into the subject using gravity-assistance. In various implementations, the system includes an infusion source capable of infusing fluid into the subject using gravity assistance and controlling the fluid flow rate within a range that includes about 0 L/hr to about 10 L/hr, about 1 L/hr to about 9 L/hr, 1.5 L/hr to about 8 L/hr, or 2 L/hr to about 6 L/hr.

In some embodiments, the disclosed systems include a hemodynamic sensor and a flow probe. The hemodynamic sensor provides one or more hemodynamic parameter dependent signals or data corresponding to a subject to an algorithm that utilizes the hemodynamic parameter data and provides recommendations to a health care provider of whether or not to infuse fluid to the subject based on the received hemodynamic parameter data. The flow probe is in communication with a monitor and measures an amount or rate of fluid infused into the subject from at least one infusion source and provides that information to the algorithm.

In some embodiments, the disclosed systems further include a flow controller providing control of the at least one infusion source in fluid communication with the subject.

In some embodiments, the disclosed systems include a gravity feed IV bag as the primary source of infusate of the system. The gravity feed IV bag, in some implementations, can be the only source of fluid infused into the subject. In various implementations, the disclosed systems include a gravity assisted IV bag as the primary source of infusate in combination with one or more secondary sources of infusate. In certain implementations, the disclosed systems include a second infusion source capable of infusing fluid into the subject. The second infusion source can be a gravity assisted source of fluid or can be an infusion pump. In some embodiments, the second infusion source provides for a fluid flow rate different from the first infusion source. For example, the second infusion source provides a fluid flow rate of about 0 L/hr to about 10 L/hr, about 1 L/hr to about 9 L/hr, 1.5 L/hr to about 8 L/hr, or 2 L/hr to about 6 L/hr, whereas all other sources of infusion into the subject are at a rate less than about 2 L/hr, less than about 1 L/hr, or less than about 0.5 L/hr.

In some embodiments, the IV bag can be initially pressurized and this pressure can be independently obtained, monitored, and/or maintained. One or more signals representing the pressure of the IV bag can be sent to the algorithm and/or manipulated by the algorithm to provide a constant head pressure of the infusion fluid over one or more intervals of time. In certain implementations, the head pressure of the infusion fluid can be varied over one or more intervals of time.

In certain embodiments, the IV bag can be configured such that its weight is dynamically, intermittently, or continuously monitored. This information can be used to determine mass flow data. The mass flow data may be transmitted to the monitor for incorporation into the algorithm and/or for presentation to the user. This can be done independently or as a backup or redundant system to the flow probe sensor and associated electronics.

As described herein, embodiments of the flow probe can provide dynamic, continuous, intermittent, or on-demand data in the form of analog or digital signals for use by the algorithm or the healthcare provider. The flow probe can be cooperatively engaged with a flow controller and controlled by the algorithm. For example, the flow probe and the flow controller can be used in an open-loop or closed-loop feedback system to control fluid flow based at least in part on measured flow-related data.

The flow probe data can be used to present on the monitor or another display flow-related data via numerical, textual, or pictorial information. This can be displayed or presented in addition to hemodynamic data. The information can include a dynamic mass flow rate and/or a mass flow rate history. The information can also include one or more recommendations as to subsequent administrations.

In some embodiments, where the system lacks any coupled flow controlling device, the healthcare provider can manually control and/or adjust the flow rate including terminating infusion. Manually controlling the flow rate by the healthcare provider can be accomplished by manipulating an independent mechanical device cooperatively engaged with the source of infusate. In certain embodiments, where the system includes an operatively coupled flow controlling device, the healthcare provider can respond to one or more prompts on the monitor or display to facilitate sending one or more electronic signals to the flow controller.

The flow probe and the flow controller can be independently or concurrently controlled by the algorithm. For example, the flow controller can be set to automatically cease infusion upon reaching a threshold infusion rate determined by the flow probe, or the flow probe can detect a disruption in the total mass flow of infusate which can signal an alarm or other indicia on the monitor or display and/or automatically terminate infusion via the flow controller. The algorithm can use existing mass flow rate history in combination with a hemodynamic parameter history to provide predictive management of future infusion events or the lack thereof.

The flow controller can be configured to stop, start, and/or vary the flow rate of the infusate along the flow path between the source of infusion fluid and the subject. The flow controller can be a valve and/or solenoid actuated. In some embodiments, the flow controller can be a mechanical valve operated by a healthcare provider. For example, the mechanical valve can be a pinch valve, a proportional valve, a two-state valve, or the like. The flow controller can be independently or concurrently controlled by the algorithm. For example, the flow controller can be set to automatically cease infusion or return to a baseline maintenance infusion rate upon reaching a threshold infusion rate determined by the flow probe, or the healthcare provider can intervene and/or override algorithmic control.

In various embodiments, the disclosed systems and methods are configured to find a plateau and/or stable window of data in response to the hemodynamic parameter sensor data, flow probe data, and subject status. In certain embodiments, if the system cannot reach the plateau and/or stable window of data, the system can be configured to "fail-safe." In general, the term "fail-safe" includes modifying the system processing and/or display of data in some manner responsive to a detected error, or unexpected condition, and thereby avoids processing of potentially inaccurate or clinically irrelevant hemodynamic parameter value and changing infusion parameters. In some embodiments, the disclosed systems and methods are configured to process a flow probe signal corresponding to a subject condition to determine whether the flow probe signal corresponds to an infusion rate or amount that is within a predetermined or expected subject condition range or change; if the signal falls outside the expected or predetermined range, the system is configured to fail-safe.

The following description illustrate some example embodiments in detail. Those of skill in the art will recognize that there are numerous variations and modifications of the present disclosure that are encompassed by its scope. Accordingly, the description of certain embodiments should not be deemed to limit the scope of the disclosure.

Example Subject Monitoring Systems

FIG. 1A illustrates a schematic flow diagram of a subject monitoring system 100a. The subject monitoring system 100a includes flow probe 119 in fluid communication with a fluid source 321. The fluid source can be, for example, an IV-bag, another in-line source, or a combination of the two. The subject monitoring system 100a can, in some implementations, further include at least one sensor 204 coupled to a subject 120 and/or a flow controller 301, the sensor 204 and the flow controller 301 being electronically coupled to the system via a cable or via a wireless connection. In some embodiments, the at least one sensor 204 is a hemodynamic parameter sensor. In various embodiments, flow controller 301 and flow probe 119 are configured to couple with a processing algorithm 107 and/or monitor 310 via coupler/hub 118. Coupler/hub 118 provides electronic signaling in one or both directions between processing algorithm 107 and/or monitor 310 (and/or display device) and flow controller 301 and flow probe 119. The coupler/hub 118 can include at least a portion of the system electronics. The system electronics can be configured to power the flow probe 119 and/or the flow controller 301 and/or to detect, to transmit, to receive and/or to provide signal processing for the sensed data. In some embodiments, as shown by dotted area 305, the coupler/hub 118, flow controller 301, and flow probe 119 are configured for single use/disposable components of the system 100a. The system 100a can be controlled or otherwise manipulated by a healthcare provider 125.

In various embodiments, as shown in FIG. 1A, the flow controller 301 is spatially separated, e.g., positioned "upstream" from the flow probe 119, where upstream refers to a relative position along a shared flow path relative to the subject 120. For example, the flow probe 119 can be positioned closer to the subject 120 relative to the flow controller 301 along the shared flow path from the fluid source 321. In this configuration, the flow controller 301 can selectively control the fluid source 321 (that can include one or more sources of infusion fluid) delivering fluid to the subject 120. Other sources of fluid infusion can be present in the system 100a provided that the other sources of fluid present in the system 100a are in combination with the fluid source 321 controlled by the flow controller 301 so that the fluid being delivered from the fluid source 321 and the other sources of fluid infusion pass through the flow probe 119.

In the system 100a with the upstream flow probe 119 and flow controller 301 arrangement, the healthcare provider 125 can be presented with a recommendation as to whether or not to accept the prompt generated by the algorithms 107, where the prompt can include, for example and without limitation, infuse fluid, alter an infusion rate, or terminate infusion to the subject 120. The clinician can accept the recommendation provided by the algorithms 107. Responsive to receiving an indication of acceptance, the system 100a can be configured to provide one or more signals to the flow controller 301 to adjust, to terminate or to otherwise manipulate the infusion rate of the one or more sources of infusion fluid to manage hemodynamic parameters of the subject 120 based on a combination of the flow probe data (e.g., provided by the flow probe 119) and/or subject hemodynamic parameter data (e.g., provided by the sensor 204).

In some embodiments, the subject monitoring system 100a with the flow probe 119 inline between the fluid source 321 (e.g., an IV bag) and the subject 120 is configured to deliver fluids to the subject 120 that include, for example, blood, saline, intravenous medicine, and the like. Such a system can be differentiated from flushing devices that deliver fluid to a patient to clean or clear an area during surgery.

The flow probe 119 is configured to be in line between the fluid source 321 and the patient 120, meaning that the flow of fluids passes through the flow probe 119, the flow probe 119 is attached to the conduit carrying the fluid, or the flow probe 119 is positioned (at least partially) within the conduit carrying the fluid. Such systems can be differentiated from systems that measure fluid flow or fluid delivery using other means such as by weight of the fluid in the fluid source, the level of fluid in the fluid source, a measure of fluid at the patient end (e.g., fluid suctioned into a collection container), movement of a piston or similar component in a pump, and the like. In addition, the flow probe 119 can be configured to provide an instantaneous measurement of fluid flow rate by measuring fluid flow in the conduit.

The flow probe 119 can employ any suitable means of measuring flow rate including, but not limited to, ultrasonic measurements, thermal mass measurements, pressure differentials, optoacoustic, inline turbines, or the like. The flow probe 119 can be part of a flow measurement device (e.g., the dotted box 305) that includes a housing and a length of tubing within the housing configured to couple to an input conduit and to an output conduit so that fluid flowing from the fluid source 321 flows through the flow probe 119 to the patient 120. The length of tubing of the flow measurement device can include the flow probe 119. The flow probe 119 is configured to determine a flow rate of fluid through the tubing. This flow rate measurement can be used, it in addition to properties of the tubing, to determine instantaneous flow rates as well as fluid volumes over a particular period of time.

The flow controller 301 can be configured to upstream of the flow probe 119. Flow-related data from the flow probe 119 can be processed by the algorithm 107 to control the flow controller 301. In some embodiments, the flow controller 301 is configured to operate in one of two states: a high flow state and a low flow state. The high flow state can be configured to provide a bolus or fluid challenge to the subject 120. The low flow state can be configured to provide a targeted low flow rate to prevent or reduce clots forming at the site of the cannula or to provide a background maintenance infusion.

In some embodiments, the flow controller 301 can operate to provide a targeted flow rate as determined by the algorithm 107 and/or the healthcare provider 125. The flow controller 301 can change operating parameters to provide a flow rate that changes to deliver the targeted flow rate. In some embodiments, the flow controller 301 can include one or more mechanical components that manipulate the conduit from the fluid source 321 to the subject 120 to deliver the targeted flow rate. In some embodiments, the flow controller 301 can include one or more mechanical components that direct liquid flow to one or more paths to deliver the targeted flow rate. The mechanical components of the flow controller can include, for example and without limitation, pinch valves, solenoids, rollers, clamps, valves, switches, walls, baffles, partitions, and the like. The flow controller can be configured to be a proportional valve or a discrete state valve (e.g., a valve having 2, 3, 4, or 5 or more discrete valve positions to provide a corresponding number of discrete flow rates). As an example, a proportional valve can be controlled by a stepper motor that allows the valve to control the flow rate. This may be preferable to a two-state valve that changes between two states (e.g., on and off, or low and high flow rates).

Figure 1B:
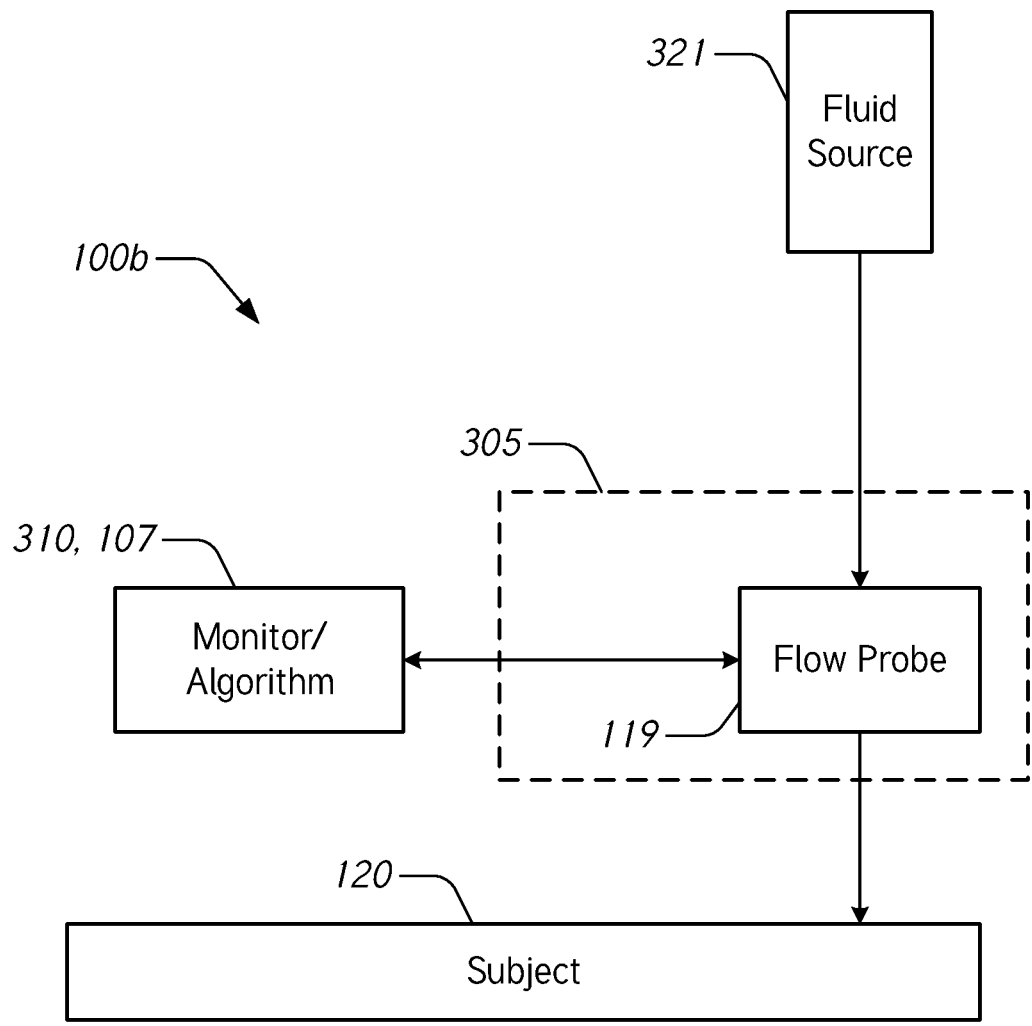
FIG. 1B is a schematic flow diagram of another subject monitoring system.

FIG. 1B illustrates another example embodiment of the subject monitoring system 100b with the system 100b including the flow probe 119 that senses volume flow or mass flow of fluid delivery to the subject 120. Based at least in part on the sensed fluid or mass flow, the flow probe 119 provides flow-related data (e.g., fluid flow rate and/or mass flow rate) that the system 100b uses to derive a volume of fluid being delivered. The fluid can be delivered from the fluid source 321 that can include an IV bag, another in-line port, or a combination of the two. The monitor 310 and/or algorithm 107 can receive the flow-related data from the flow probe 119 and can derive fluid volume and/or fluid rate. This information can be displayed on the monitor 310 and/or the flow probe 119. A clinician can use this information to gain an understanding of the volume of fluid/mass the subject 120 has received. This system 100b finds applicability in determining an amount of fluid delivered, and is applicable without any flow controlling device or means.

Figure 1C:
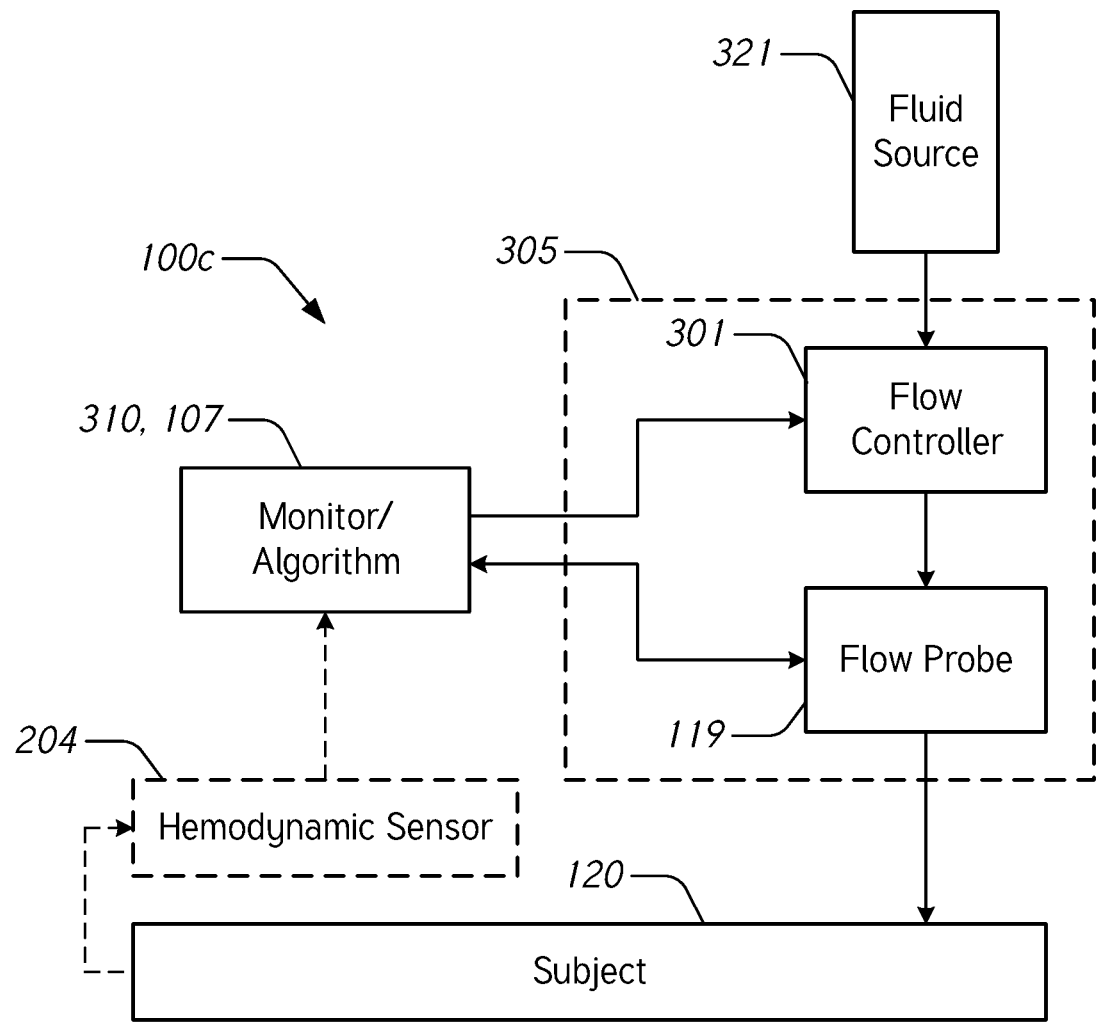
FIG. 1C is a schematic flow diagram of another subject monitoring system.

FIG. 1C illustrates another example embodiment of the subject monitoring system 100c with the system 100c including the flow probe 119 that senses fluid flow or mass flow of fluid delivery to the subject 120 and the flow controller 301 that controls the fluid flow from the fluid source 321 to the subject 120. The flow probe 119 provides flow-related data (e.g., fluid flow rate and/or mass flow rate) that the system 100c uses to derive a volume of fluid being delivered. The fluid can be delivered from the fluid source 321 that can include an IV bag, another in-line port, or a combination of the two. The monitor 310 and/or algorithm 107 can receive the flow-related data from the flow probe 119 and can derive fluid volume and/or fluid flow rate. This information can be displayed on the monitor 310 and/or the flow probe 119. A clinician can use this information to gain an understanding of the volume of fluid/mass the subject 120 has received. In addition, this information can be used in a feedback loop to control the fluid flow via the flow controller 301.

In some embodiments, the system 100c also includes the physiological sensor 204 that provides physiological data to the algorithm 107. The physiological sensor 204 can be a hemodynamic sensor, for example. The hemodynamic sensor can be the FLOTRAC® sensor, in certain implementations. The physiological sensor 204 can be configured to provide information capable of being transformed into one or more forms of heart output data. In some embodiments, an oximetry device can be used as part of the physiological sensor 204. In certain embodiments, the oximetry device can be a finger cuff device that is integrated with the system 100c, the system electronics, and/or the monitor 310 and/or the algorithm 107. The system 100c can utilize the physiological data in the algorithm 107 to determine how the subject 120 responds to administered fluid volumes. Based on the correlated sensed data from the flow probe 119 and the data from the physiological sensor 204, the algorithm 107 can determine the response of the subject 120, provide information (e.g., a recommendation) to the clinician regarding subsequent bolus administration, and/or control the amount and rate of volume of fluid delivered to the subject 120 using the flow controller 301.

In some embodiments, the flow controller 301 is operated independently of the sensed fluid flow (e.g., manually or electronically but without being part of a feedback loop using flow-related data). This may be useful to deliver a bolus to the subject at a desired time and/or for a desired duration. In some embodiments, although the flow controller 301 is configured to be controlled automatically by the algorithm 107, the system 100c can be configured to provide the clinician the ability to override the algorithm 107 and its administration protocol.

Figure 1D:
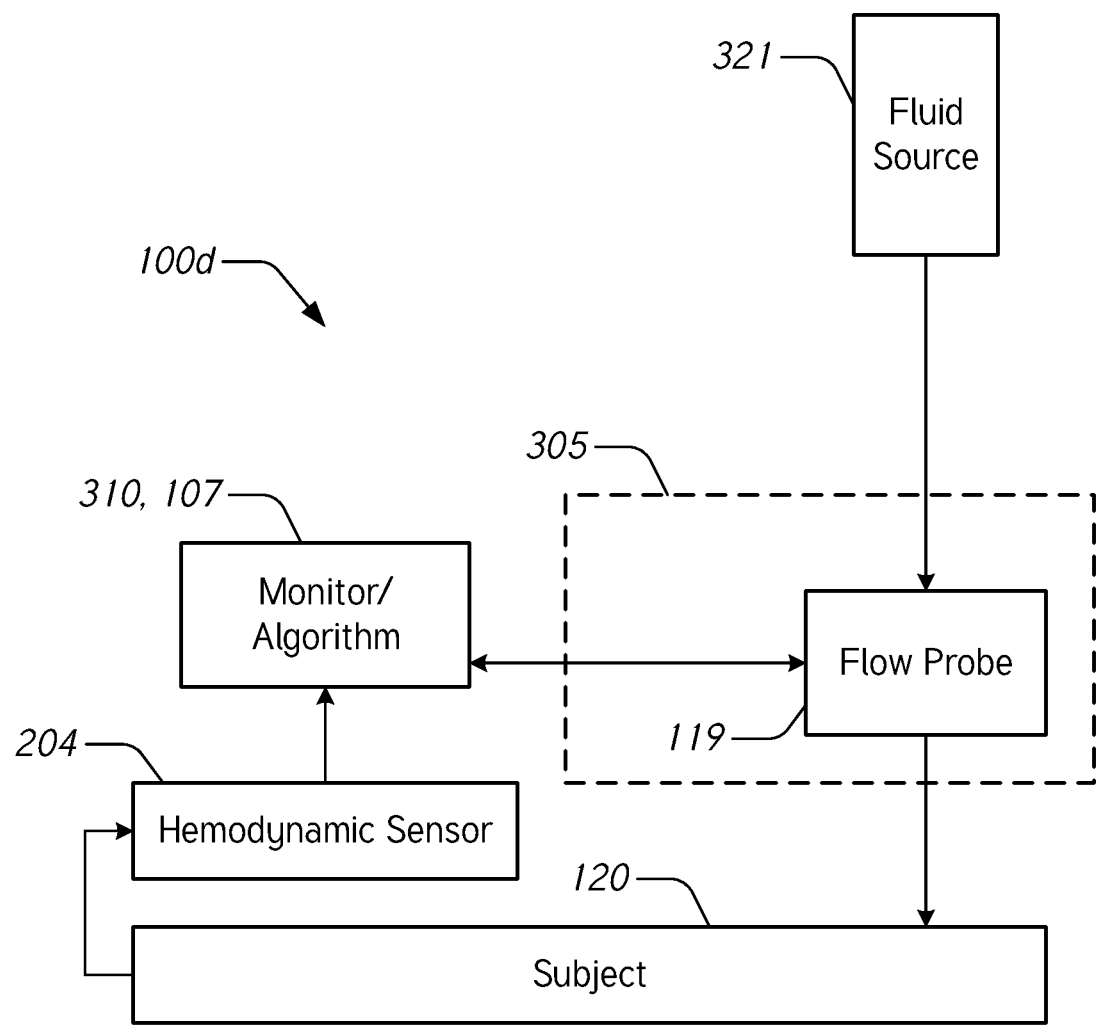
FIG. 1D is a schematic flow diagram of another subject monitoring system.

FIG. 1D illustrates an example embodiment of the subject monitoring system 100d that includes the flow probe 119, the physiological sensor 204, and the monitor 310 with the algorithm 107. The monitor 310 can, for example, include a graphical user interface (GUI). In the system 100d, the flow probe 119 can be configured to sense flow-related information in combination with sensed physiological data from the physiological sensor 204. In such implementations, the physiological sensor information (e.g., provided by the physiological sensor 204) can be utilized along with the fluid delivery related data (e.g., provided by the flow probe 119) to generate a recommendation to a clinician of one or more subsequent administration protocols that can include adjustments or targeted flow rates and/or fluid volumes. In various implementations, there is no automated flow controller or other automated device to automatically control administration of the fluid. Thus, in this aspect, it is in the discretion of the clinician to control the subsequent administration of fluid based on the recommendation provided by the system 100d (e.g., displayed or communicated using the monitor 310).

Figure 1E:
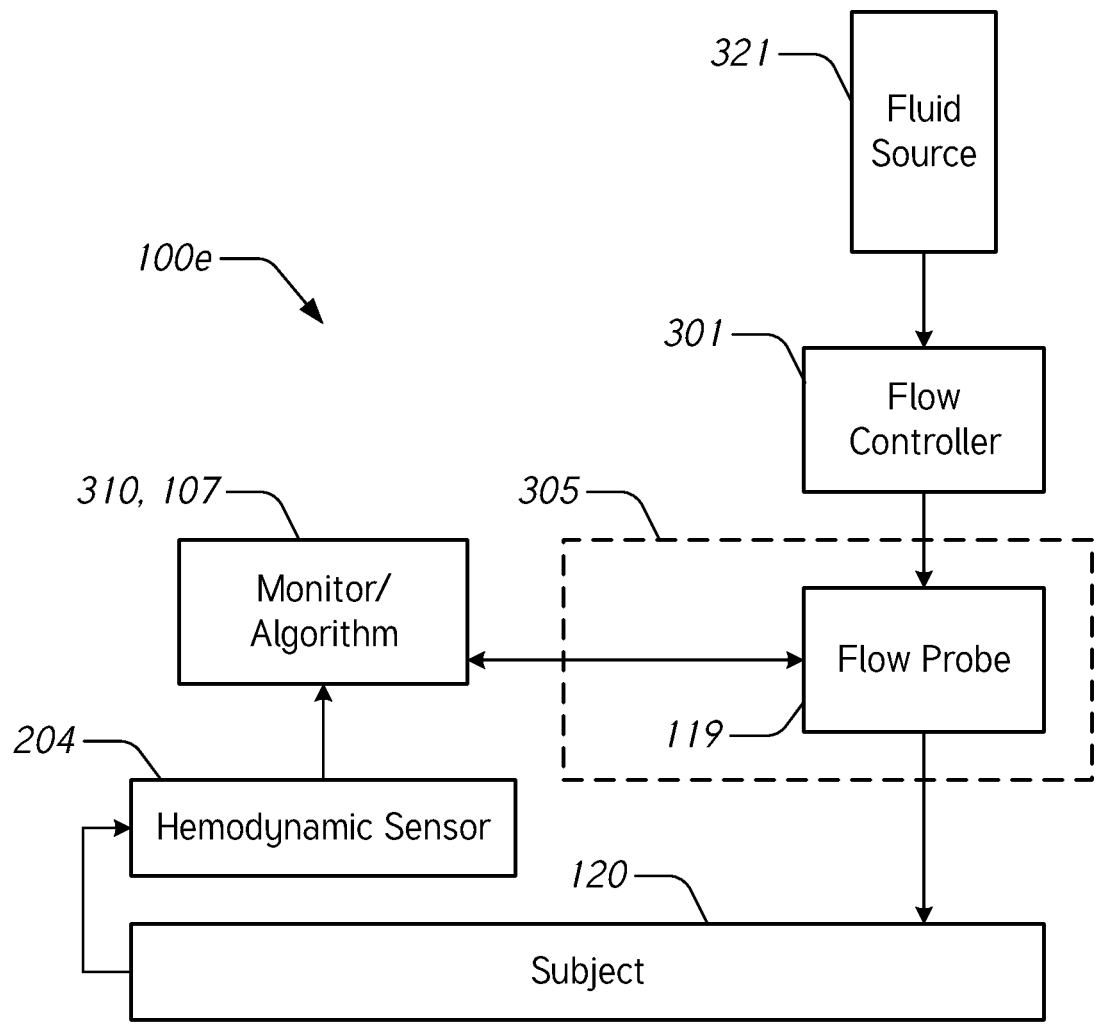
FIG. 1E is a schematic flow diagram of another subject monitoring system.

FIG. 1E illustrates another example embodiment of the subject monitoring system 100e that includes the flow probe 119, the physiological sensor 204 that provides physiological data to the algorithm 107 wherein the algorithm 107 utilizes the flow-related information and the physiological sensor data to provide recommendations regarding subsequent administration protocol(s) that can include a targeted flow rate and/or volume and/or adjustments to the flow rate and/or volume. The system 100e also includes the flow controller 301 in fluidic communication with the fluid source 321, that can be manually manipulated to vary fluid delivery rate and, by extension, the volume of fluid delivered. The flow controller 301 is configured to be controlled by the clinician manually. The actual physical control of fluid administered can be a standard IV roller clamp, for example. Such manual control of fluid delivery may be part of a standard IV tubing set that can be connected and/or adapted for use with the system 100e. Thus, it may be in the discretion of the clinician to control the subsequent administration of fluid based on the recommendation provided by the system (e.g., through the algorithm 107 and the monitor 310).

Figure 1F:
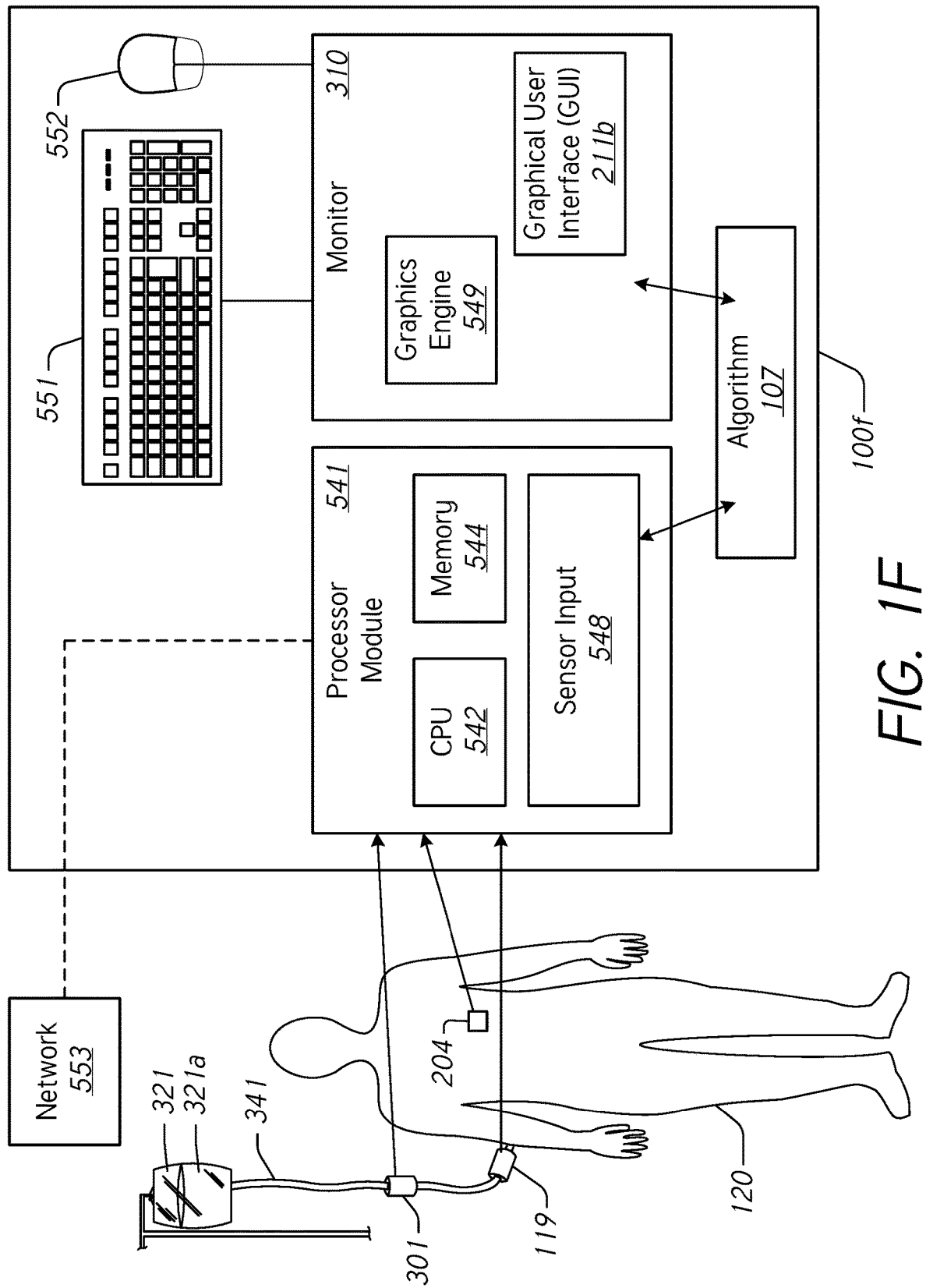
FIG. 1F is an example schematic block diagram of the subject monitoring system of FIG. 1A.

FIG. 1F illustrates a schematic diagram of a subject monitoring system 100f similar to the subject monitoring system 100a of FIG. 1A. The subject monitoring system 100f includes at least one sensor 204 coupled to a subject 120. In some embodiments, the monitoring system 100f is a bed-side system, and can be integrated into an existing drug delivery stand, bedbox, or monitoring system rack. In certain implementations, the at least one sensor 204 is a hemodynamic parameter sensor. The system 100f also includes the flow probe 119. Sensor 204 and flow probe 119 are configured to couple with a processor module 541. In some embodiments, the processor module 541 is connected to a network 553, such as a wired or wireless network, to allow monitoring on a remote display (not shown). The memory unit 544 can be a volatile memory, such as flash memory, or non-volatile memory, such as read-only memory. In addition, the memory unit 544 can be a database that is located within the system 100f, or alternatively, located remotely from the system 100f. In some embodiments, the memory unit 544 can be located within or coupled to the monitor 310.

Processor module 541 is coupled to the monitor 310. Monitor 310 includes a graphics engine 549 and graphical user interface (GUI) 211b to render and display the signals received from the processor module 541. The graphics engine 549 and the GUI 211b outputs images and graphics corresponding to the physiological data to the monitor 310 or other display device. In some embodiments, the monitor 310 can be configured through the graphical user interface 211b to be touch-sensitive, and allows data or commands to be entered by an application of pressure, via, for example, a clinician's finger or a stylus, to the monitor 310. Furthermore, the monitor 310 can include a keyboard 551 for data input. The keyboard 551 can be a touch sensitive keyboard located on a portion of the monitor 310, or it can be an external hard keyboard coupled to the monitor 310. A mouse or pointing device 552 can be coupled to the monitor 310 and used to enter data or commands into the system 100f. The monitor 310 can be configured to receive voice command instructions using dictation software stored on or in the processor module 541.

In some embodiments, the monitor 310 and the processor module 541 can be an integrated unit within a single housing. In certain embodiments, the processor module 541 can be separate from the monitor 310.

The processor module 541 and/or the monitor 310 can include one or more data storage devices comprising computer program code, e.g., algorithm 107, specifically configured such that when operated on by one or more electronic processors causes said one more electronic processors to perform operations, such as running code related to receiving and/or transmitting signals (e.g., to/from the sensors, telemetry components, display, user input devices, etc.), calculating values, interactions with graphical interfaces, and the like.

Figure 2:
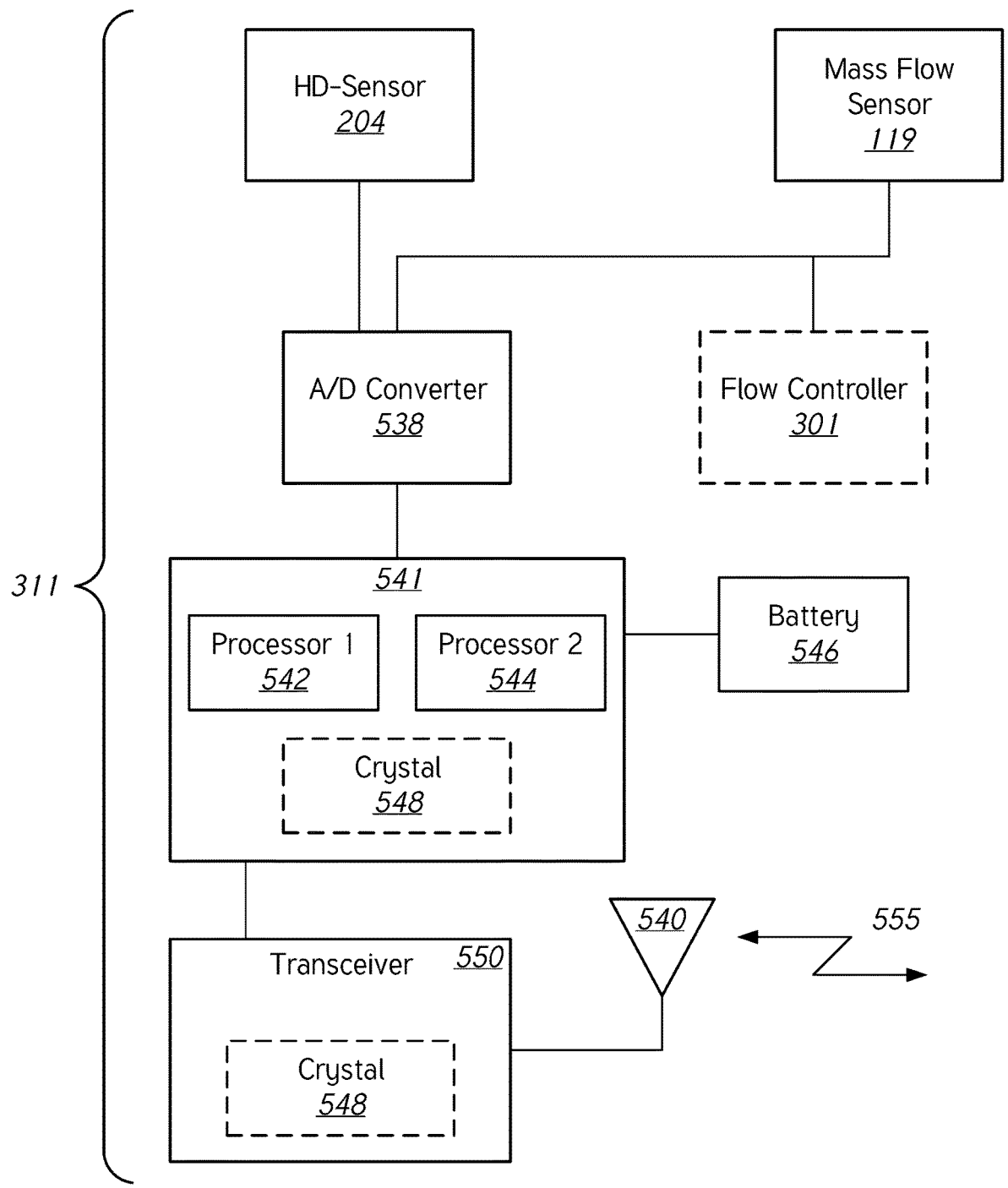
FIG. 2 is a block diagram of an example embodiment of system electronics.

FIG. 2 illustrates system electronics 311 associated with the processor module 541 that acts as central control unit and that houses, for example, a first processor 542 and a second processor 544 (e.g., where the processor can be an EEPROM, SRAM, or the like). The processor module 541 is configured to control the processing of the system electronics 311. In certain embodiments, a computer system other than a microprocessor is used to process data as described herein. In some embodiments, the processors can include an application specific integrated circuit (ASIC) for some or all the central processing. The EEPROM 542 provides semi-permanent storage of data, for example, storing data such as sensor identifier (ID) and programming to process data streams. The SRAM 544 can be used for the system's cache memory, for example for temporarily storing recent sensor data. In some alternative embodiments, memory storage components comparable to EEPROM and SRAM may be used instead of or in addition to the disclosed hardware, such as dynamic RAM, non-static RAM, rewritable ROMs, flash memory, or the like.

A transceiver 550 (e.g., an RF transceiver) can be operably connected to the microprocessors 542, 544 to transmit the sensor data from either the HD-sensor 204 (e.g., hemodynamic sensor or physiological sensor) or the flow probe 119 to a receiver within a wireless transmission 555 via antenna 540. Although an RF transceiver is shown here, embodiments can include a wired rather than wireless connection to the receiver. A second quartz crystal 548 can provide the system time for synchronizing the data transmissions from the RF transceiver 550. It is noted that the transceiver 550 can be substituted with a transmitter in some embodiments. In some embodiments, other mechanisms such as optical, infrared radiation (IR), ultrasonic, or the like may be used to transmit and/or receive data.

In addition to receiving signals from the flow probe 119 and/or controlling fluid infusion, the processor module 541 includes systems and methods for receiving and processing signals such as an analog-to-digital (A/D) converter 538 to obtain one or more sensor values from either sensor independently or each of the hemodynamic parameter sensor 204 and the flow probe 119. In addition, the processor module 541 includes systems and methods for displaying the one or more sensor values from either or both the hemodynamic parameter sensor 204 and the flow probe 119.

With reference to FIG. 1F, the data or results can be displayed on the monitor 310, e.g., via a graphics engine 549. The processor module 541 can include systems and methods for sending and receiving one or more sensor signals or calculated values from the hemodynamic parameters sensor 204, the flow probe 119, and/or flow controller 301 to a network 553 via the Internet, intranet, or telecommunication system.

The telemetry (e.g., radiotelemetry) devices contemplated for use in conjunction with either of the hemodynamic parameter sensing device, flow probe, and flow controller possess features including small package size, adequate battery life, acceptable noise-free transmission range, freedom from electrical interference, and easy data collection and processing. Telemetry provides several advantages, including the ability of an implanted or inserted device to measure hemodynamic parameter values in a sealed-off, sterile environment. The present disclosure is not limited by the nature of the telemetry equipment or methods for its use. Indeed, commercially available equipment can be modified for use with the devices of the present disclosure. Similarly, custom-designed telemetry devices used in hemodynamic parameter monitoring can be used in conjunction with the hemodynamic parameter sensing devices of the present disclosure. In some implementations, transmitters can be configured (including programming) with an external magnet to transmit at 4-, 32-, or 256-second intervals, with battery lifetimes at the current longest transmission intervals (about 256 seconds) approximately up to two years or more. In various implementations, transmitters, along with the hemodynamic parameter sensing device, are configured as "disposables," with lifetimes of days, weeks, or months.

With reference to FIG. 2, a battery 546 or other power source is operably connected to the microprocessor 542 and provides power for sensor 204, flow probe 119, and/or flow controller 301. In some embodiments, the battery 546 is rechargeable. In various embodiments, a plurality of batteries can be used to power the system. In certain embodiments, one or more capacitors can be used to power the system. A quartz crystal 548 may be operably connected to the processor module 541 to maintain system time for the system as a whole.

Figure 3A:
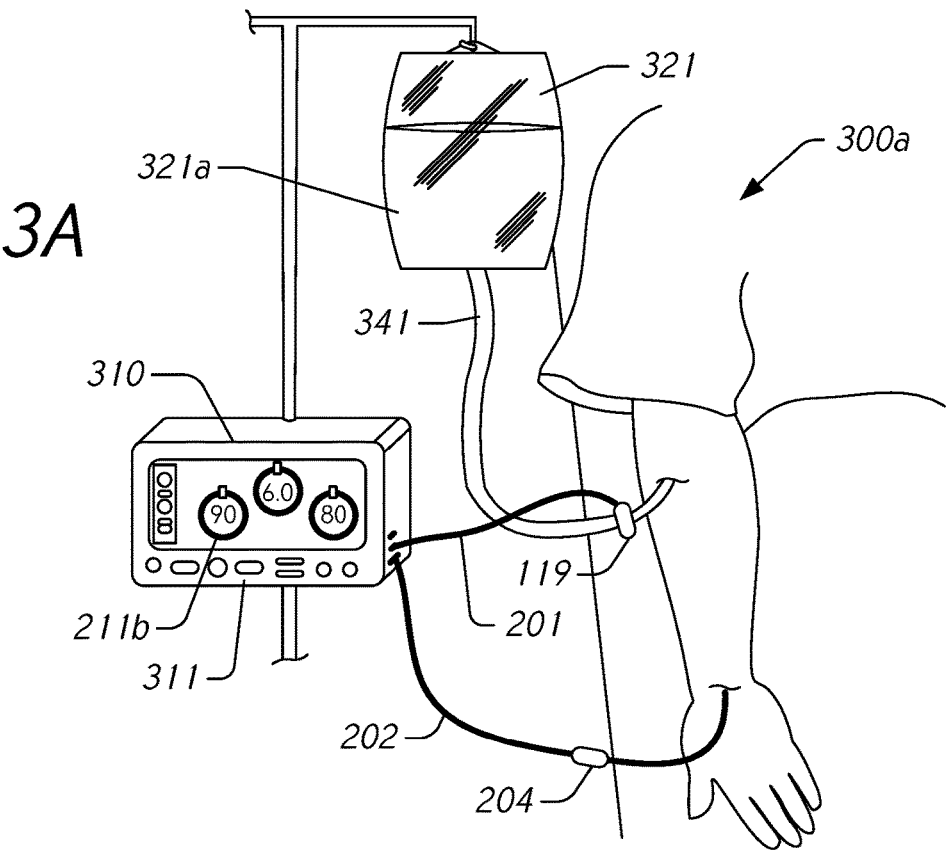
FIGS. 3A and 3B are representations illustrating various embodiments of a system configuration for managing a hemodynamic state.
Figure 3B:
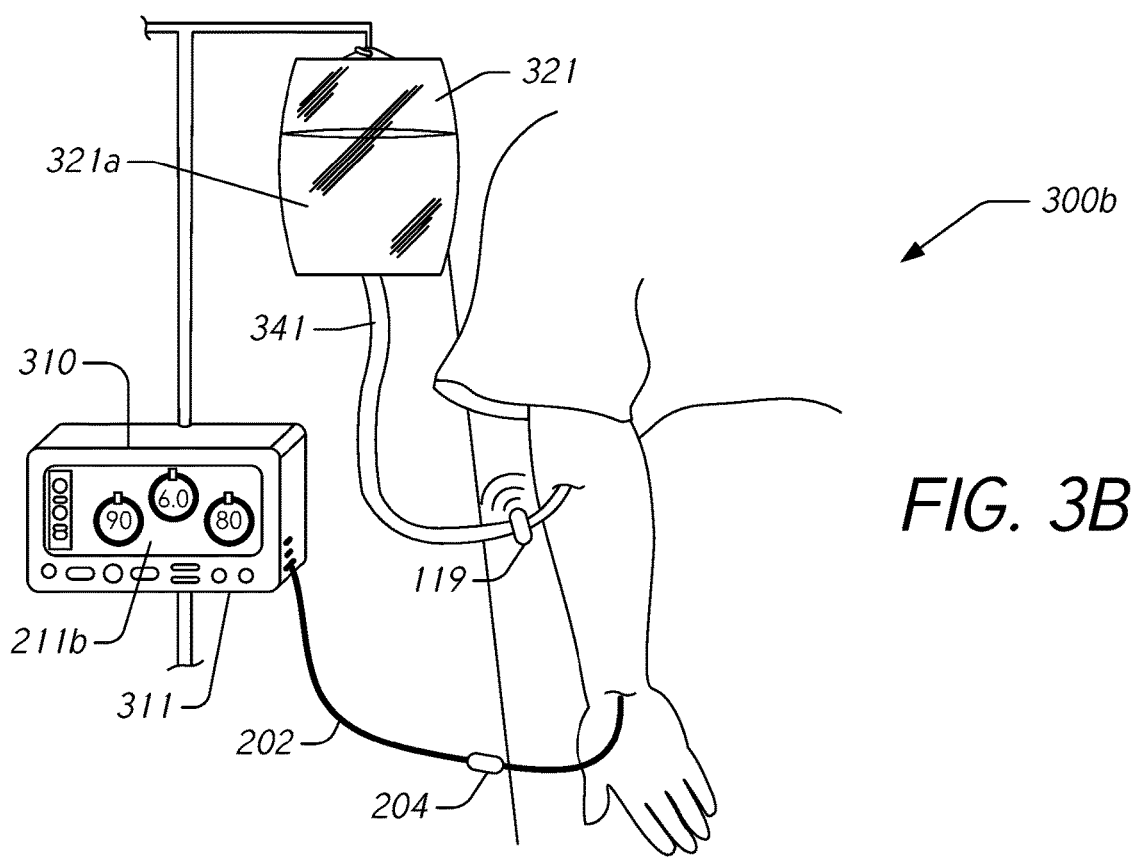

FIGS. 3A and 3B illustrate example embodiments of subject monitoring systems described herein. FIG. 3A depicts an integrated system 300a (as a variation of any of the systems 100a-100f described herein with reference to FIGS. 1A-1F) for hemodynamic management. FIG. 3B depicts a partially wireless system 300b (as a variation of any of the systems 100a-100f described herein with reference to FIGS. 1A-1F) for hemodynamic management. Systems 300a, 300b comprises a hemodynamic parameter data sensor 204 (also referred to as "HD-sensor" or "hemodynamic parameter sensor") and a flow probe 119 (also referred to as "mass flow sensor" or "flow rate sensor") with fluid 321a being infused via an IV bag 321, for example, into a subject via tubing 341. Referring to FIGS. 3A and 3B, the systems 300a, 300b include a flow probe 119 that is wired or wirelessly coupled to the monitor 310, respectively.

FIG. 3A illustrates the flow probe 119 with a dedicated system cable 201 to the electronic module, communication module, and/or monitor 310. While system 300a can include an HD-sensor and a flow-sensor of any type, the discussion hereinafter is directed to pressure sensors and magnetic or ultrasonic flow sensors, as an example embodiment of the system 300a. Thus, the system 300a includes HD-sensor 204, a vascular access device, such as a catheter, and the flow probe 119 along the flow path of the catheter and coupled to system electronics 311 or otherwise coupled to a processor module and/or the monitor 310. In some embodiments, the HD-sensor 204 is a pressure sensor configured and arranged to generate a signal associated with or corresponding to the blood pressure of the circulatory system of a subject.

The vascular access device (not shown) such as a catheter, is connected to an infusion source 321, such as an IV bag, containing an infusion fluid 321a, via tubing 341. The infusion source 321 is capable of infusing fluid into the subject via gravity, or at a rate of about 2 L/hr to about 6 L/hr. The tubing 341 is fluidically coupled with the flow probe 119, which is configured to determine the mass/time rate or total volume of one or more infused fluids into the subject and is responsive to the system electronics 311. The vascular access device coupled to the tubing 341 may comprise multiple ports or lumens for the introduction of one or more fluids independent of or in cooperation with the contents of the gravity feed IV bag. For example, the vascular access device can include a Swan-Ganz type catheter implanted in the subject's circulatory system (e.g., a vein or artery), and/or the flow probe 119 connected to the catheter can be configured to detect and/or monitor total fluid introduction to the subject from one of the access ports associated with the Swan-Ganz catheter.

With reference to FIGS. 3A and 3B, the systems 300a, 300b include system electronics 311 operably connected to one or both of the HD-sensor 204 and the flow probe 119, and configured to receive and/or process one or more signals generated by the HD-sensor 204 and/or the flow probe 119. The one or more signals can be associated with a hemodynamic parameter (e.g., a static or a dynamic value) of the subject's hemodynamic state and the mass flow rate or total mass volume infused into the subject.

In FIG. 3A, the system electronics 311 are operably coupled to electronic cable 201, which in turn can be operably coupled to the flow probe 119, such as but not limited to an ultrasonic or magnetic flow probe or device that measures the weight (load) of an IV bag and provides continuous, intermittent, or on-demand estimates to the system electronics 311 and/or algorithm of the weight of the bag for determining infusion volume and/or infusion rate.

With continued reference to FIG. 3A, an electronic cable 201 is operably coupled to the system electronics 311 and monitor 310 and is configured and arranged to operably connect with the flow probe 119. Alternatively, as in system 300b depicted in FIG. 3B, wireless communication operably couples the monitor 310 and flow probe 119. The system can include a unique and/or interactive display/monitor 211b, which can be configured to communicate with the systems 300a, 300b by wired and/or wireless transceiver components known in the art.

Figure 4A:
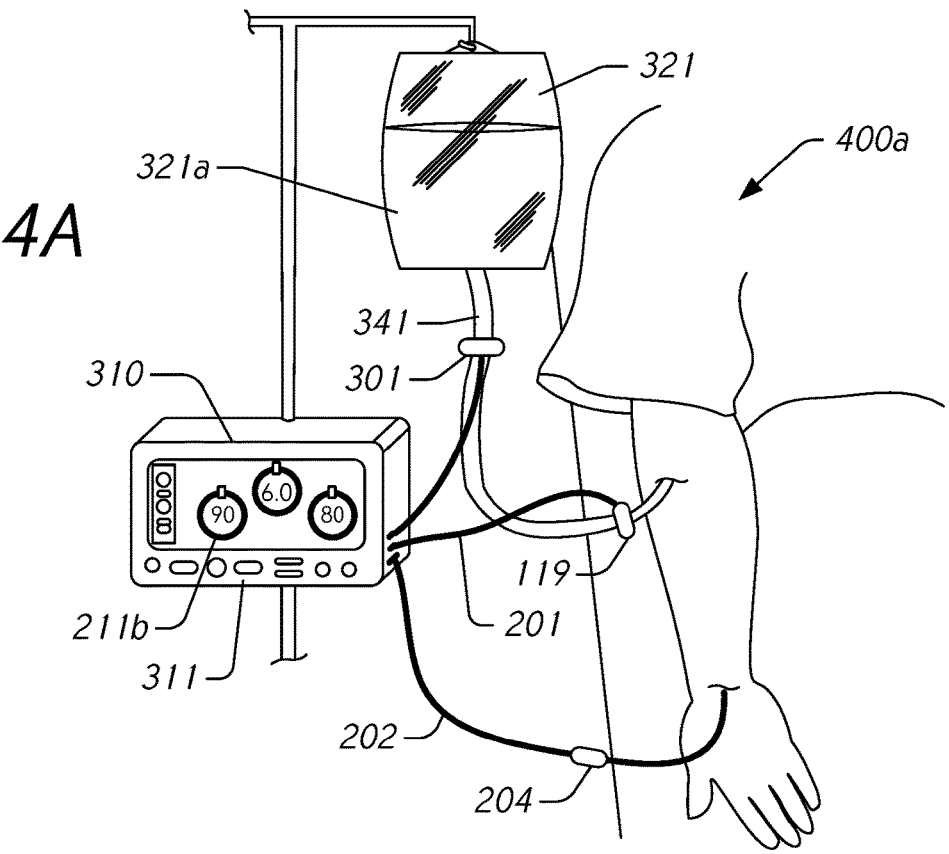
FIGS. 4A and 4B are representations illustrating various embodiments of a system configuration for managing a hemodynamic state.
Figure 4B:
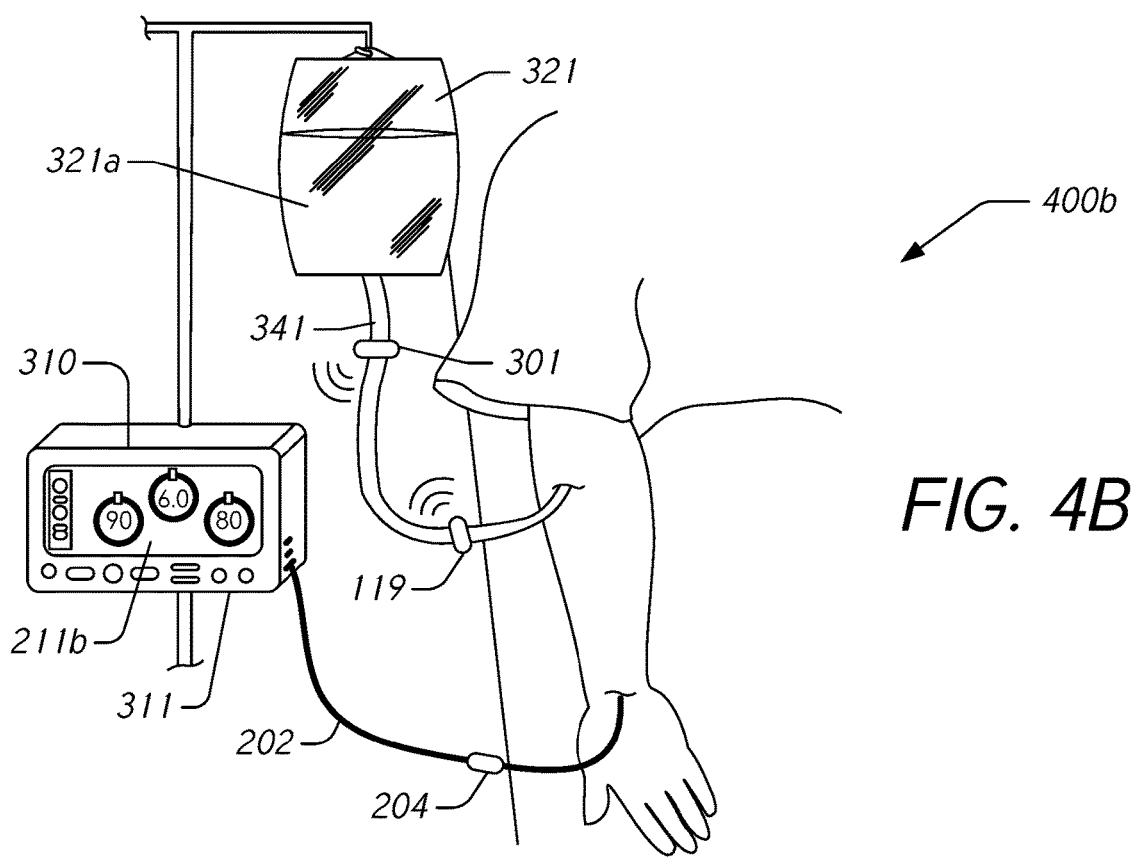

FIGS. 4A and 4B illustrate example infusion systems 400a, 400b, respectively, that include an apparatus configured to control delivery of fluid. The apparatus is coupled to a processor module, an algorithm, and/or the monitor 310. Systems 400a, 400b are similar to the systems 300a, 300b of FIGS. 3A and 3B, respectively, with the addition of the flow controller 301. Examples of flow controllers are described herein with reference to FIGS. 6A-6E.

A process controller of the systems 400a, 400b determines a first effect on a physiological parameter of the subject associated with administration to the subject of a first fluid bolus corresponding to a first mass flow condition, and stores first administration-related data relating to the first effect within device storage. The first mass flow condition can include infusion of a fluid to the subject at a rate of about 0 L/hr to about 10 L/hr, about 1 L/hr to about 9 L/hr, 1.5 L/hr to about 8 L/hr, or 2 L/hr to about 6 L/hr (e.g., a high flow rate). The process controller then determines a second effect on the physiological parameter of the subject associated with administration to the subject of a second fluid bolus corresponding to a second mass flow condition, and stores second administration-related data relating to the second effect within the device storage. The second mass flow condition can include infusion of a fluid to the subject at a rate the same or different from the first mass flow condition by sending a signal to the flow controller 301 to adjust the flow rate of fluid 321a. The process controller provides a fluid administration signal based upon at least one of the first administration-related data or the second administration-related data. In some embodiments, the fluid administration signal is directed to the flow controller 301.

The systems 400a, 400b can be configured to incorporate one or more algorithms that receive and/or transmit information from the hemodynamic parameter sensor 204, flow probe 119, and flow controller 301 for providing methods of improved patient outcomes, assisted fluid delivery, and/or automated fluid optimization while using a clinician's preferred workflow. The systems 400a, 400b can be used with methods for open-loop and/or closed-loop patient-adaptive hemodynamic management, such as those disclosed in U.S. Pat. No. 8,617,135, entitled "System and Method for Closed-Loop Patient-Adaptive Hemodynamic Management," issued Dec. 31, 2013, which is incorporated herein by reference in its entirety.

In some embodiments, the HD-sensor 204 is a pressure sensor that generates a signal associated with or corresponding to the blood pressure of the circulatory system of a subject and the flow probe 119 is a magnetic or ultrasonic mass flow measuring device that generates a signal associated with the infusion rate and/or infusion volume of one or more fluids introduced to a patient through the catheter or tubing. Other means of monitoring the flow rate or mass of fluid can be used, such as a mass or weight method.

Figure 5:
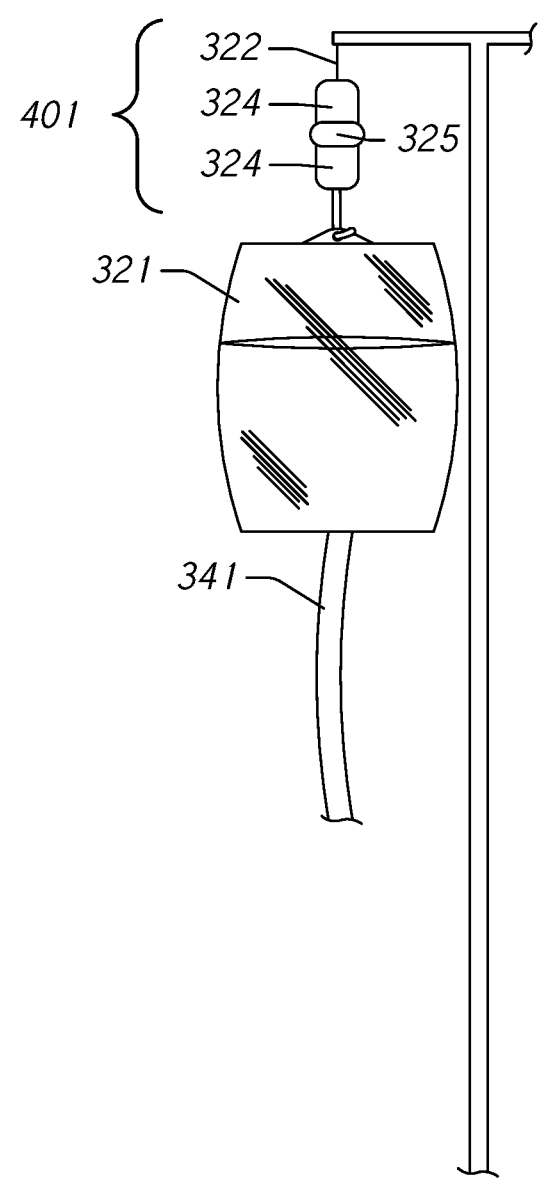
FIG. 5 is a diagram representation of an exemplary weight sensor as disclosed and described herein.

For example, FIG. 5 depicts and IV bag weight monitoring device 401 shown attached to a stand and an IV bag. IV bag weight monitoring device 401 includes a load cell 325 with vertically opposing projecting members 324, one member connected to a coupler 322 for suspending from a stand, and the other member for connecting to the IV bag. Load cell 325 are available commercially such as an iLoad Mini Sensor (LoadStar Sensors (Fremont, Calif.)) or a LSB200 Miniature-Beam Load Scale (FUTEK Advanced Sensor Technology, Inc, Irvine Calif.). The IV bag weight monitoring device 401 is configured to provide IV fluid levels/flow rates based on the weight of the IV bag and its contents. The IV bag weight monitoring device 401 monitors the weight of the IV bag and provides a signal to an interface that can calculate the amount of fluid present and the rate of dispensing of the fluid per minute. The IV bag weight monitoring device 401 interface can be configured to provide signals to a processor module (e.g., the processor module 541 described herein) for use by an algorithm (e.g., the algorithms 107 described herein) and/or as a user-friendly GUI interface to display on a monitor (e.g., the monitor 310 described herein). In some embodiments, the IV bag weight monitoring device 401 provides a signal to a processor module, algorithm, and/or monitor as an alternative to signals otherwise provided by a flow probe (e.g. the flow probe 119 described herein). In some embodiments, the IV bag weight monitoring device 401 provides a signal to the processor module, algorithm, and/or monitor in addition to signals provided by the flow probe.

Thus, the systems described herein provide for a clinical device that is capable of administering fluids, determining infusion volumes and/or rates, controlling infusion, and providing for the administration of fluids, (e.g., blood products, and medications), such administrations being calculated and/or controlled by an algorithm, monitoring the subject response to fluids administered, and displaying one or more of the sensed parameters, mass flow rates of infusion fluids, calculated values, and dynamically, intermittently, or continuously monitored information to the healthcare provider. The disclosed systems provide for the automation and standardization of administration of intravenous fluids, blood products, and/or blood-pressure modifying medications, for example, to improve patient outcomes.

The disclosed apparatuses, methods, and systems also provide devices and systems configured to administer or direct the administration of anesthetics or for use in anesthesiology, among other healthcare related functions.

The systems, in combination with the disclosed methods, are capable of improving methods of dynamically adapting to specific subjects using known biases in conjunction with associated physiological parameters, their means and standard deviations in relationship to one another, and observed responses to previous interventions by the systems; determining whether a fluid bolus (of an amount and/or at a specified infusion rate) and/or blood-pressure adjusting medications are indicated; and, if so, administering them or providing an indication to the healthcare provider to administer them. The systems are also configured for monitoring responses in combination with mass flow data and adapting to the subject, and determining whether additional fluid bolus and/or blood product administration is indicated, and, if so, administering them or providing an indication to the healthcare provider to administer them.

The disclosed apparatuses, methods, and systems also provide for improved enhanced learning and adaptation by data (of a multitude of subjects) shared between devices over time to improve the algorithm of the systems and to improve expectations across patient populations. The use of fluid administration volumes, for example, at rates of about 2 L/hr to about 6 L/hr in the adapting process provides for improved dynamic and/or real-time adjustments to future fluid administration volumes and/or rates and their thresholds, as well as improved control of the administration dose and threshold of medication, as well as automatic adjustments to the weight of each measured parameter in decision-making by the algorithm of the apparatus.

Using a combination of the change in fluid predictive parameters and the change in cardiac output in response to a bolus delivered at rates of about 2 L/hr to about 6 L/hr corresponding to a specific mass flow rate or volume allows an improved measurement of the bias present in a particular subject at a particular time and allows for subject-adaptive responses to be addressed more accurately. Using a combination of the change in the fluid predictive parameters and the change in cardiac output in response to a bolus corresponding to a mass flow rate or volume infused at about 2 L/hr to about 6 L/hr provides for a dynamically accurate measurement of the bias present in a particular subject at a particular time and allows for subject-adaptive responses to be addressed and/or improved.

The disclosed apparatuses, systems and methods provide for one or more hemodynamic parameters to be used in combination with high infusion volumes and/or high infusion rates, the hemodynamic parameters corresponding to cardiac output information, for administration of fluids and/or pharmacologic agents, such as blood-pressure affecting drugs, among other things. Thus, the disclosed systems and methods include a device capable of administering or instructing the administration of IV fluids, blood, and/or medications to subjects autonomously and a set of processes for measuring and/or controlling fluid administration volume to achieve a target or predicted hemodynamic profile. The method includes receiving administration-related data relating to one or more physiological processes of a subject corresponding to infusion rates of about 0 L/hr to about 10 L/hr, about 1 L/hr to about 9 L/hr, 1.5 L/hr to about 8 L/hr, or 2 L/hr to about 6 L/hr. The method also includes determining, based at least in part upon the administration-related data, administration-related data associated with a current state of the subject. The method also includes adjusting, using a processor and algorithm, administration of fluid to the subject based at least in part upon the administration-related data.

The systems and devices include one or more processors and memory operatively coupled to the one or more processors. The memory stores signals from at least one hemodynamic sensor and at least one flow probe which, when executed by the one or more processors, cause the one or more processors to receive administration-related data relating to one or more physiological processes of the subject and mass flow data, and to determine, based at least in part upon the administration-related data, administration-related data associated with a current state of the subject. The signals further cause the one or more processors to adjust (directly or indirectly) administration of fluid to the subject based at least in part upon the administration-related data.

Example Flow Controllers

Figure 6A:
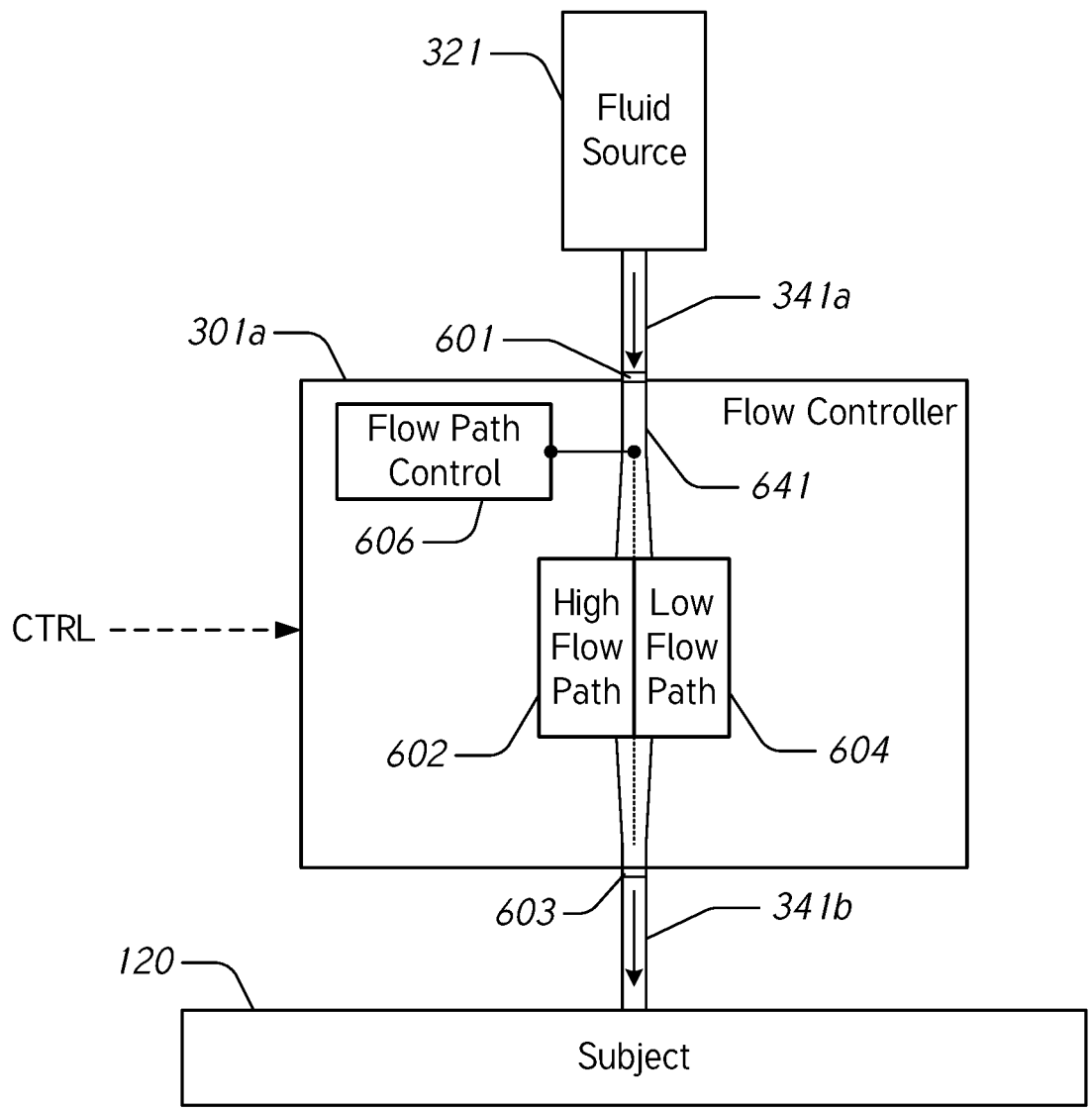
FIG. 6A illustrates a schematic diagram of a flow controller that combines high flow and low flow.

FIG. 6A illustrates a schematic diagram of an example flow controller 301a that is configured to operate in a low flow state and in a high flow state. The flow controller 301a is configured to regulate liquid flow between the fluid source 321 and the subject 120. The fluid source 321 provides liquid that flows through the input conduit 341a (e.g., an IV line) and the flow controller 301a that can provide an uninterrupted low flow of liquid and, when desired, a high flow rate for bolus delivery. The flow controller 301a includes an input port 601 that couples to the input conduit 341a and an output port 605 that couples to an output conduit 341b. The flow controller 301a includes an internal conduit 641 between the input port 601 and the output port 603 to provide a path for liquid through the flow controller.

The flow controller 301a includes a high flow path 602 and a low flow path 604 to respectively provide a high flow rate and a low flow rate. The flow controller 301a includes a flow path control 606 to direct liquid to the high flow path 602 (e.g., when operating in a high flow state) or the low flow path 604 (e.g., when operating in a low flow state). The flow path control 606 can include one or more mechanical components that direct liquid flow to a targeted path. In some embodiments, the flow path control 606 is coupled to the internal conduit 641. The flow path control 606 can be within the internal conduit 641, partially within the internal conduit 641, or wholly outside the internal conduit 641 but in contact with the internal conduit 641 to manipulate a cross-section or inner diameter of the internal conduit 641 to control flow. In certain implementations, the internal conduit 641 may be partitioned or divided to provide different paths corresponding to the high flow path 602 and to the low flow path 604. In various implementations, the internal conduit 641 is not partitioned or divided and the flow path control 606 is configured to manipulate the internal conduit 641 to control the inner diameter of the internal conduit 641 to provide the high flow path 602 and the low flow path 604. For example, in the low flow state, the flow path control 606 can restrict the inner diameter of the internal conduit 641 to a first size thereby providing the low flow path 604. Similarly, in the high flow state, the flow path control 606 can release the internal conduit 641 or can restrict the inner diameter of the internal conduit 641 to a second size larger than the first size thereby providing the high flow path 602.

In some embodiments, when operating in the high flow state, the flow path control 606 is configured to direct liquid from the fluid source 321 to the high flow path 602 and to the low flow path 604 so that the resulting flow rate is a combination of the flow rate through the high flow path 602 and the low flow path 604. In such embodiments, when operating in the low flow state, the flow path control 606 is configured to shut or block the high flow path 602 so that the resulting flow rate is the flow rate through the low flow path 604. This can allow the flow controller 301a to provide a targeted low flow rate based at least in part on properties of the low flow path 604.

In some embodiments, the flow controller 301a receives a control signal (CTRL) that is used to control the flow path control 606. The control signal can correspond to a high flow state or a low flow state. Responsive to receiving a control signal corresponding to the high flow state, the flow path control 606 directs liquid from the fluid source 321 to the high flow path 602. Similarly, responsive to receiving a control signal corresponding to the low flow state, the flow path control 606 directs liquid from the fluid source 321 to the low flow path 604.

In some embodiments, the flow controller 301a is manually operated to switch between the low flow state and the high flow state. For example, an operator can manipulate the flow path control 606 to switch from the low flow state to the high flow state or vice versa.

As used herein, a high flow rate can correspond to a flow rate that is greater than or equal to about 0.5 L/hr and/or less than or equal to about 10 L/hr, greater than or equal to about 1 L/hr and/or less than or equal to about 8 L/hr, or greater than or equal to about 2 L/hr and/or less than or equal to about 6 L/hr. As used herein, a low flow rate can correspond to a flow rate that is greater than or equal to about 1 mL/hr and/or less than or equal to about 100 mL/hr, greater than or equal to about 5 mL/hr and/or less than or equal to about 80 mL/hr, or greater than or equal to about 10 mL/hr and/or less than or equal to about 60 mL/hr. In some embodiments, a ratio of the high flow rate to the low flow rate is at least about 10 and/or less than or equal to about 1000, at least about 100 and/or less than or equal to about 800, or at least about 300 and/or less than or equal to about 600.

In some embodiments, the flow controller 301a is configured to attach to a conduit rather than coupling to the input conduit 341a and the output conduit 341b. In such embodiments, the flow controller 301a can be coupled to an existing conduit between the fluid source 321 and the subject 120 to provide a high flow rate and an uninterrupted low flow rate to the subject 120. Examples of such flow controllers are described herein with reference to FIGS. 6B and 6D.

In some embodiments, the flow controller 301a can be configured to provide a range of flow rates from no flow (e.g., completely closed) to a high flow rate (e.g., completely opened) with flow rates that fall within these values being provided by partially opening (or partially closing) the internal tubing 641 with any suitable mechanism (e.g., a plunger).

Figure 6B:
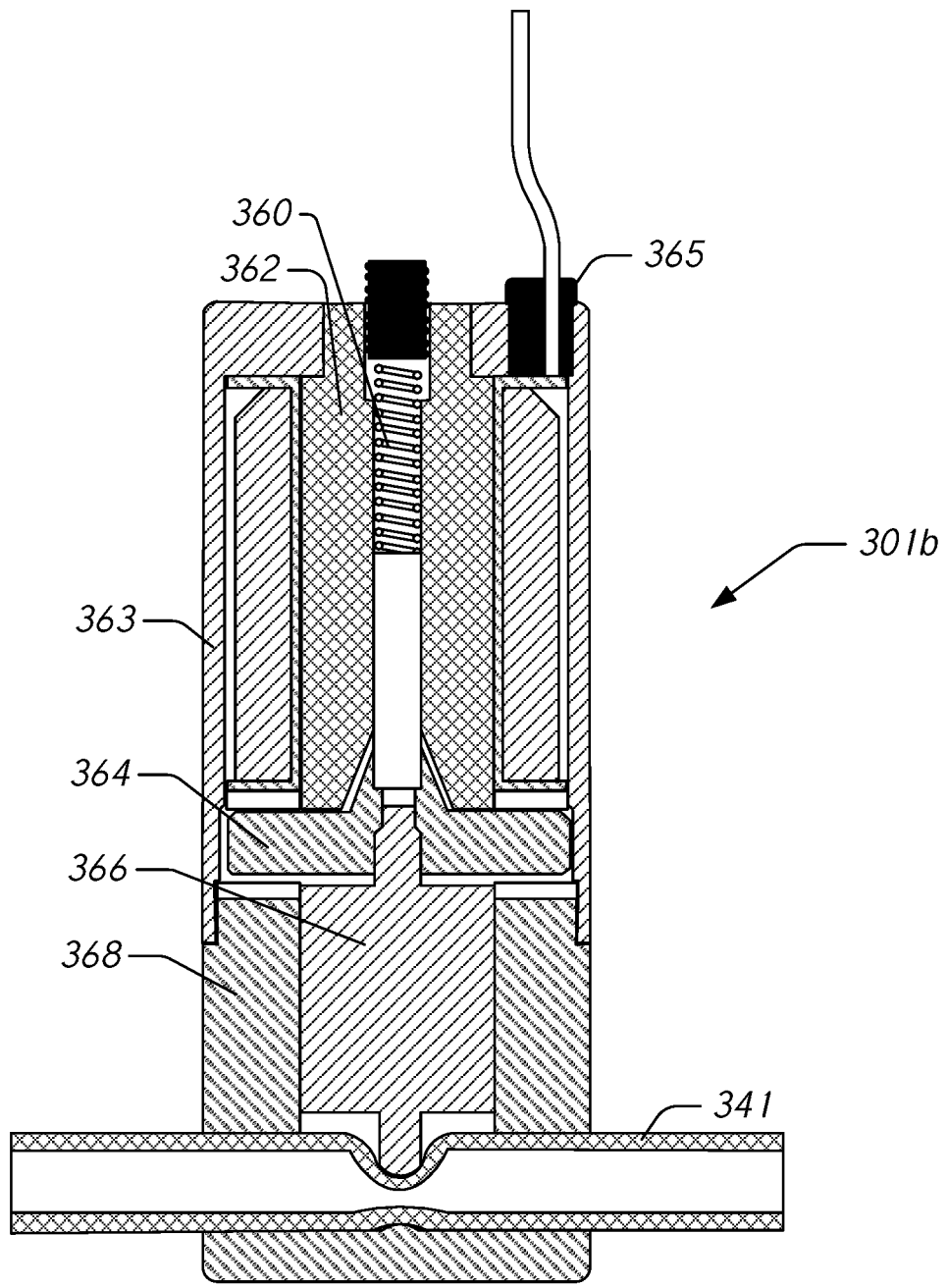
FIG. 6B is a sectional view of an exemplary solenoid flow controller as disclosed and described herein.

FIG. 6B illustrates an example flow controller 301b that includes a solenoid-based, "pinch valve." The flow controller 301b can be attached to an existing conduit 341 and/or can provide an internal conduit as described herein with reference to FIG. 6A. The flow controller 301b is configured to be energized to provide the high flow state and to be de-energized to provide the low flow state. However, it is to be understood that the flow controller 301b can be configured to provide a range of flow rates by applying different amounts of electrical energy.

The flow controller 301b includes a solenoid 362 electrically coupled to energizing means 365, solenoid 362 encased in housing 363 coupled to body 368, solenoid 362 having biasing spring 360 coupled to armature 364 for driving plunger 366 against tubing 341 to compress the tubing and restrict fluid flow therethrough. Energizing solenoid 362 via energizing means 365 causes retraction of the plunger 366 for allowing unrestricted fluid flow through tubing 341 receiving fluid from IV bag 321. The energizing solenoid 362 causes spring 360 to bias plunger 366 and to reduce the internal diameter of tubing 341 to restrict fluid flow. In some embodiments, the flow controller 301b can be configured such that unrestricted fluid flow is provided in the de-energized state (reversed configuration as previously described). Energizing means 365 can be configured for control by an algorithm (e.g., the algorithm 107 described herein) and can include user override and/or other safety protocols. Other types of pinch valve flow controllers can be used. Pinch valve flow controllers are commercially available, for example, from BIO-Chem, Neptune Research, ASCO Valve Inc., Clippard Instrument Laboratory, and Valcor Engineering Corp.

The flow controller 301b can be configured to operate in a high flow state when the solenoid 362 is energized. The flow controller 301a can be configured to operate in a low flow state when the solenoid 362 is de-energized to reduce the internal diameter of tubing 341 to restrict fluid flow to a targeted flow rate.

Figure 6C:
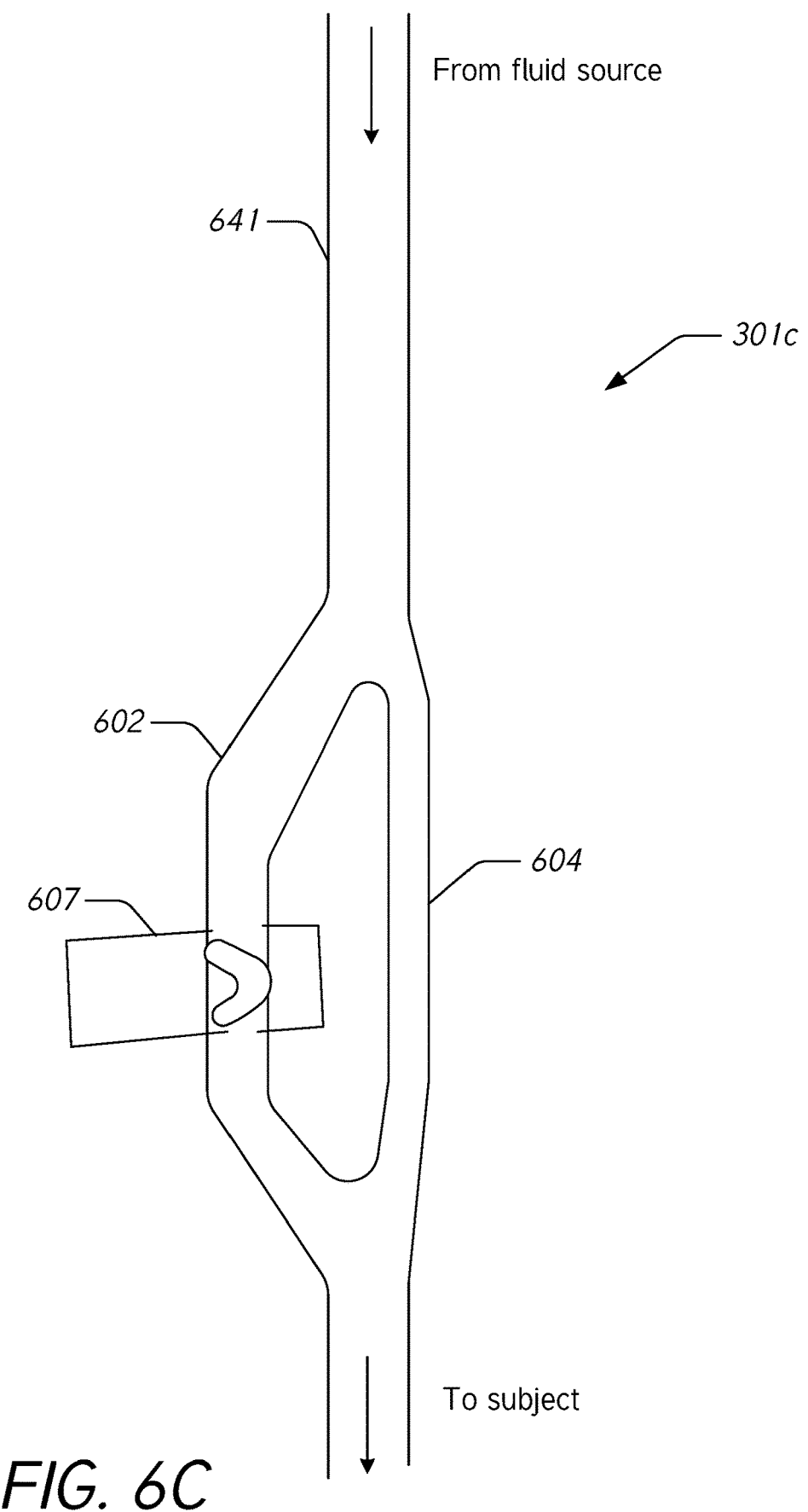
FIG. 6C illustrates an example flow controller that combines high flow and low flow.

FIG. 6C illustrates an example flow controller 301c that combines high flow and low flow. The flow controller 301c uses a bypass tube to selectively provide the high flow rate and the low flow rate. The flow controller 301 includes internal conduit 641 that splits into two conduits providing two fluid paths, a high flow path 602 and a low flow path 604. Along the low flow path 604, there is no valve and the inner diameter of the conduit determines the low flow rate. In some implementations, the conduit of the low flow path 604 can be replaceable so that a targeted low flow rate can be achieved by installing a conduit with a targeted diameter. Along the high-flow or bolus path 602, a pinch valve 607 or other similar flow control device operates to fully open or fully close the conduit in the high flow path 602. This allows a fluid delivery system, doctor, or other suitable person to control delivery of a bolus to a patient. The volume of liquid from both the high flow path 602 and the low flow path 604 can be added together to determine the total liquid volume delivered to the patient.

The pinch valve 607 can be electrically or communicably coupled to a control system that commands the valve 607 to open and close. In some embodiments, the valve 607 operates in one of two states: in a high flow state the valve is completely open (e.g., not restricting or minimally restricting the inner diameter of the conduit of the high flow path 602), and in a low flow state the valve is completely closed (e.g., restricting the conduit of the high flow path 602 to block fluid flow through that conduit). In this low flow state, the flow of liquid from the fluid source to the subject passes entirely through the low flow path 604.

Figure 6D:
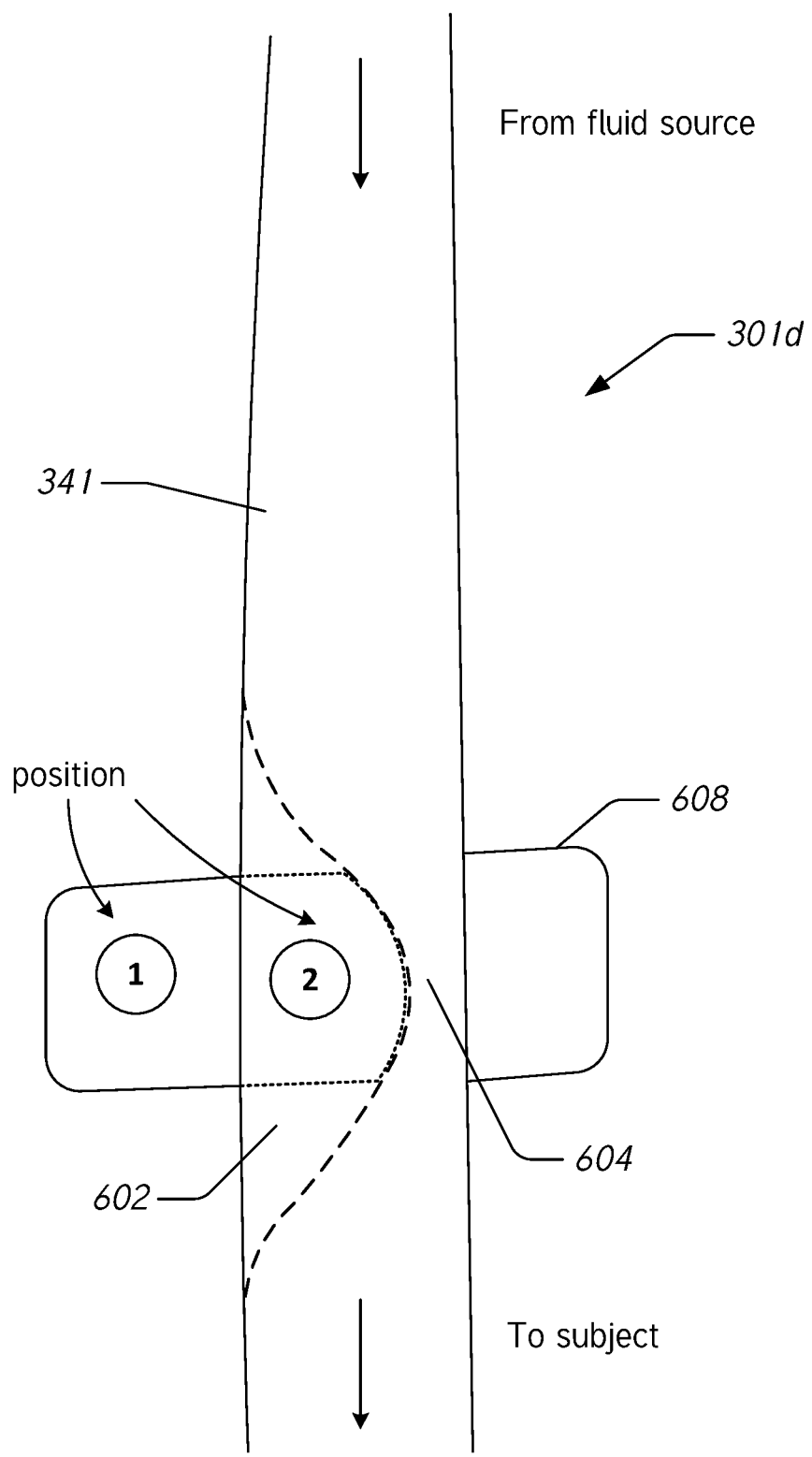
FIG. 6D illustrates another example flow controller that combines high flow and low flow.

FIG. 6D illustrates another example flow controller 301*d* that combines high flow and low flow. The flow controller 301 uses a tailored pinch valve 608 that is configured to never fully close the conduit 341. The pinch valve 608 can be similar to the pinch valve described herein with respect to FIG. 6B.

The pinch valve 608 is tailored so that it operates to move between two defined positions: an open position (illustrated as position #1) and a closed position (illustrated as position #2). With the valve 608 in an open position (i.e., position #1), a high-flow rate can be provided for bolus delivery. With the valve in a closed position (i.e., position #2), the valve 608 clamps the conduit 341 to generate a gap of a targeted size to provide a targeted low flow rate of liquid to the patient. The valve 608 can be tailored or customized to change either position (e.g., the open position and/or the closed position) to provide targeted flow rates to the patient. In such implementations, the open position and/or the closed position can be customized and the valve 608 moves between these two defined positions during operation. The valve 608 can be electrically or communicably coupled to a control system that commands the valve to move between these two positions.

When the valve 608 is in the closed position, the size of the restricted diameter is a primary factor in determining the low flow rate. Similarly, when the valve 608 is in the open position, the size of the unrestricted (or less-restricted) diameter is a primary factor in determining the high flow rate. Accordingly, the sizes of the respective paths in the open and closed positions can be tailored or tuned to provide targeted high and low flow rates.

Figure 6E:
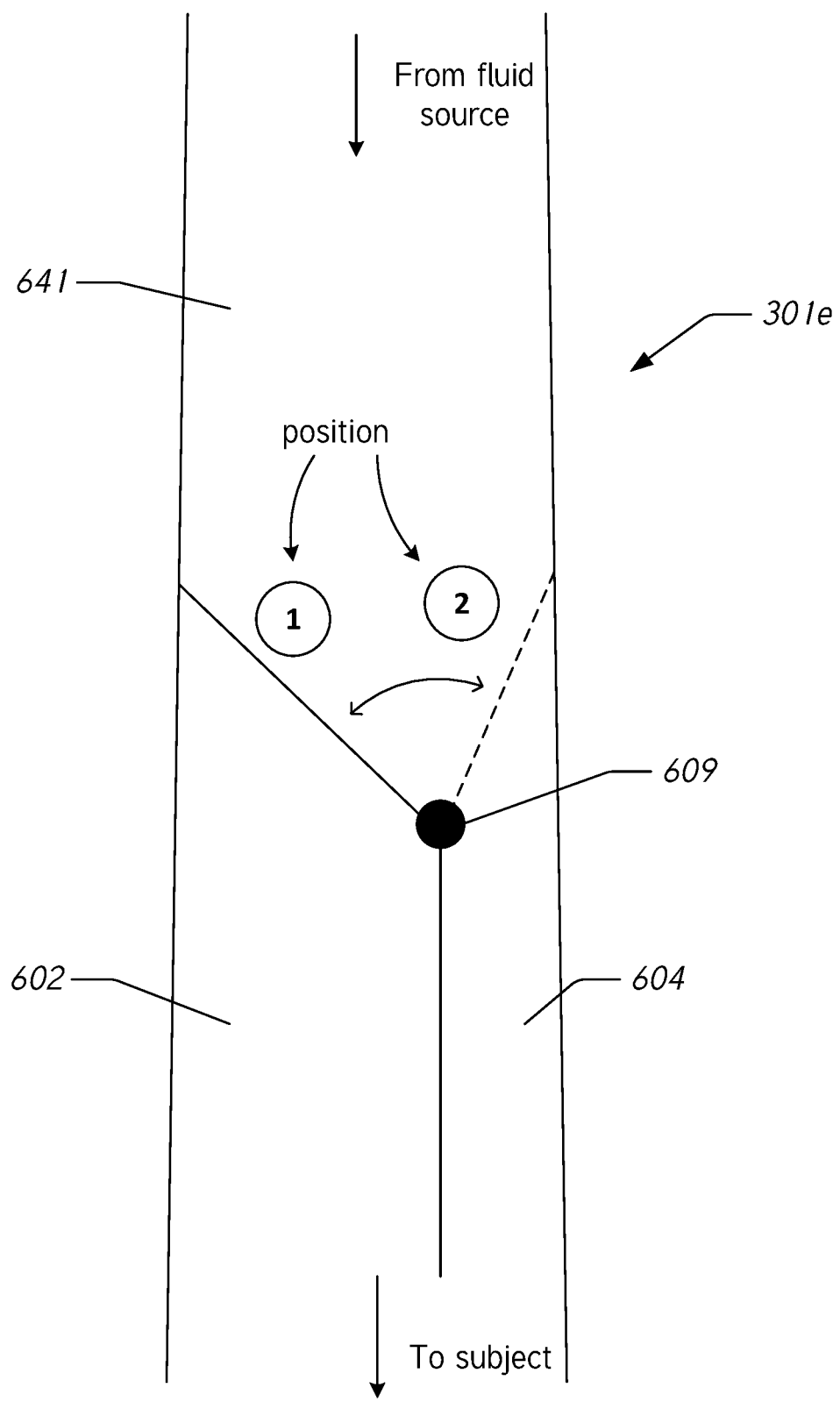
FIG. 6E illustrates another example flow controller that combines high flow and low flow.

FIG. 6E illustrates another example flow controller 301*e* that combines high flow and low flow. The flow controller 301*e* includes a valve (switch) 609 to switch between two outlet paths: a low-flow path 604 and a high-flow path 602. In a first position (e.g., illustrated as position #1), the switch 609 blocks fluid flow to the high-flow path 602 resulting in a low flow rate through the low-flow path 604. In a second position (e.g., illustrated as position #2), the switch 609 blocks fluid flow to the low-flow path 604 resulting in a high flow rate through the high-flow path 602. The switch 609 can be electrically or communicably coupled to a control system that commands the switch 609 to move between these two positions.

When the switch 609 is in the first position, the cross-section (e.g., inner diameter) of the low flow path 604 is a primary factor in determining the low flow rate. Similarly, when the switch 609 is in the second position, the cross-section (e.g., inner diameter) of the high flow path 602 is a primary factor in determining the high flow rate. Accordingly, the sizes of the respective paths can be tailored or tuned to provide targeted high and low flow rates.

Example Methods for the Administration of Fluid to a Subject

The disclosed systems can be configured to carry out one or more computer-implemented methods. In a first aspect, a computer-implemented method for facilitating the administration of fluid to a subject is provided. The computer-implemented method includes determining a first effect on a physiological parameter of the subject associated with administration to the subject of a first fluid bolus event under a first mass flow condition, and then storing, using a processor, first administration-related data relating to the first effect corresponding to the first mass flow condition. In some embodiments, the first mass flow condition includes infusion of a fluid to the subject at a rate of about 2 L/hr to about 6 L/hr.

The method further includes determining a second effect on the physiological parameter of the subject associated with administration to the subject of a second fluid bolus event corresponding to a second mass flow condition, and then storing, using a processor, second administration-related data relating to the second effect corresponding to the second mass flow condition. In some embodiments, the second mass flow condition comprises infusion of a fluid to the subject at a rate of about 2 L/hr to about 6 L/hr. The method further includes generating, using the processor, a fluid administration signal based at least in part upon the first administration-related data and the second administration-related data on the physiological parameter of the subjects. In some implementations, the fluid administration signal is directed to a flow controller.

In some embodiments, a method is provided comprising a device that includes one or more processors, and a memory operatively coupled to the one or more processors, the memory storing program code which, when executed by the one or more processors, determines a first effect on a physiological parameter of the subject associated with the method of administration to the subject of a first fluid bolus corresponding to a first mass flow condition, and storing first administration-related data relating to the first effect within device storage. In some embodiments, the first mass flow condition comprises infusion of a fluid to the subject at a rate of about 2 L/hr to about 6 L/hr. The method further comprises providing for the program code determining a second effect on the physiological parameter of the subject associated with administration to the subject of a second fluid bolus corresponding to a second mass flow condition, storing second administration-related data relating to the second effect within the device storage, and generating a fluid administration signal based upon at least one of the first administration-related data and the second administration-related data. In some embodiments, the second mass flow condition comprises infusion of a fluid to the subject at a rate of about 2 L/hr to about 6 L/hr. In some embodiments, the fluid administration signal is directed to a flow controller. In some embodiments, the first and the second bolus related data is obtained from an infusion to the subject at a rate of about 6 L/hr.

In certain embodiments, a computer-implemented method for providing clinical decision support relating to the administration of fluid to a subject at a rate of about 2 L/hr to about 6 L/hr is provided. The method includes receiving administration-related data comprising sensor data corresponding to one or more physiological processes of a subject corresponding to at least one infusion mass flow condition, determining, based at least in part upon the administration-related data, administration-related data associated with a current state of the subject, and providing, using a processor, a fluid administration recommendation based at least in part upon the administration-related data.

In various embodiments, a computer-implemented method for providing clinical decision support relating to the administration of fluid to a subject at a rate of about 2 L/hr to about 6 L/hr is provided. The method comprises determining a first effect on a physiological parameter of the subject associated with an administration of a first fluid bolus to the subject corresponding to a first mass flow condition, storing, using a processor, first administration related data relating to the first effect, determining a second effect on the physiological parameter of the subject associated with administration of a second fluid bolus to the subject corresponding to a second mass flow condition, storing, using a processor, second administration-related data relating to the second effect, and providing, using the processor, a fluid administration recommendation based at least in part upon at least one of the first administration-related data and the second administration-related data.

In some embodiments, a computer-implemented method for providing clinical decision support relating to the administration of fluid to a subject is provided. The method includes receiving administration-related data relating to one or more effects on a state of the subject associated with prior administration of fluid to the subject corresponding to a prior mass flow condition of infusion of a fluid to the subject at a rate of about 2 L/hr to about 6 L/hr, then determining, using a processor and based upon the administration-related data, a predicted change in a physiological parameter of the subject in response to the administration of a fluid bolus to the subject. The method further includes providing, using the processor, a fluid administration recommendation corresponding to a mass flow condition based upon the predicted change.

In some embodiments, a computer-implemented method for facilitating the administration of fluid bolus to a subject is provided. The method includes receiving administration-related data relating to one or more effects on a state of the subject associated with prior administration of a fluid bolus to the subject corresponding to a prior mass flow condition of infusion of a fluid to the subject at a rate of about 2 L/hr to about 6 L/hr, and determining, using a processor, and based upon the administration-related data, a predicted change in a physiological parameter of the subject in response to the administration of a fluid bolus to the subject corresponding to a new mass flow condition of infusion of a fluid to the subject at a rate of about 2 L/hr to about 6 L/hr. The method further includes generating, using the processor, a fluid administration signal corresponding to the new mass flow condition based upon the predicted change. In some embodiments, the fluid administration signal is directed to a flow controller.

Figure 7:
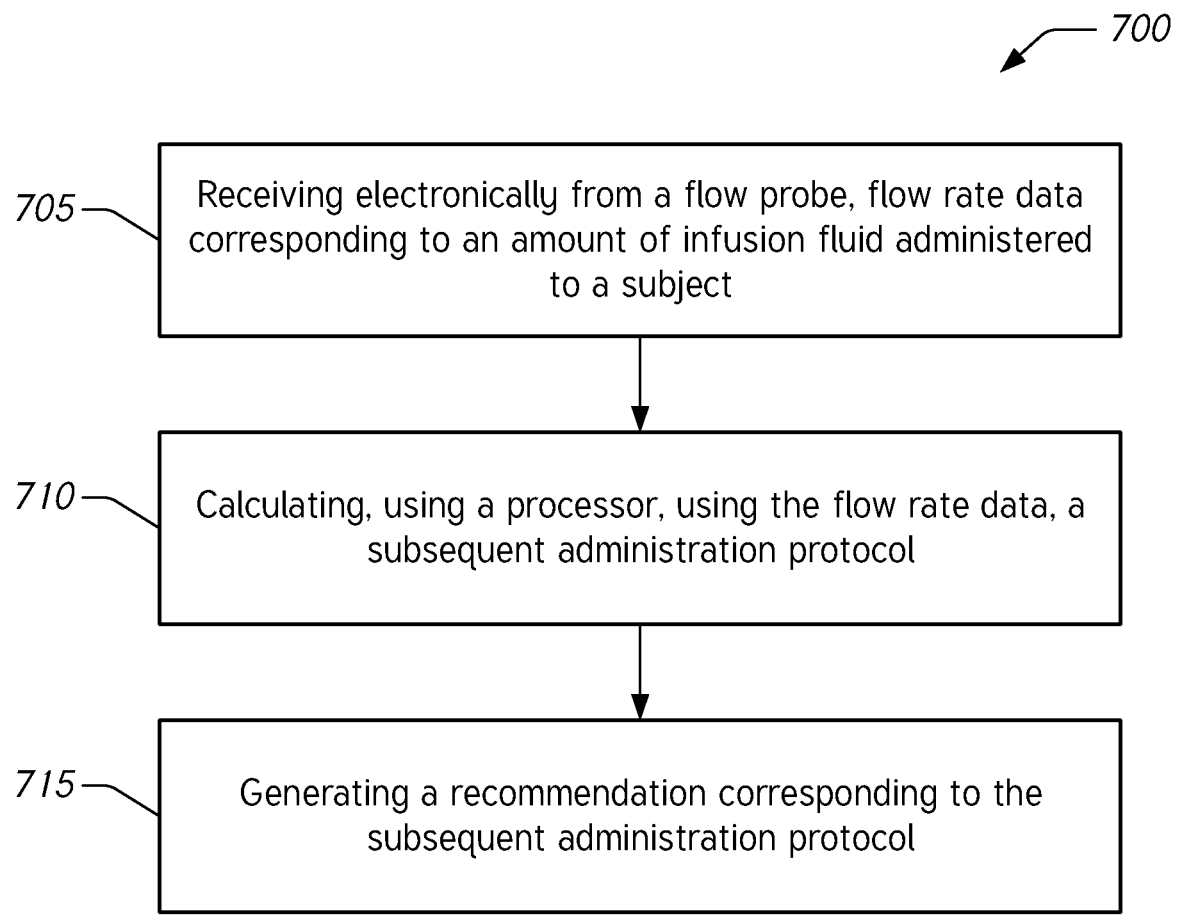
FIG. 7 is a flow chart of an example method as disclosed and described herein.

FIG. 7 illustrates a flowchart of an example process 700 for providing assisted delivery management in combination with the systems, apparatuses, and methods disclosed herein. The process 700 can be performed by any of the subject monitoring systems 100a-100f respectively illustrated in FIGS. 1A-1F and FIG. 2 and/or the systems 300a, 300b, 400a, 400b respectively illustrated in FIGS. 3A, 3B, 4A, and 4B. Accordingly, for ease of description, the process 700 is described as being performed by the system and/or a processor of the system. However, it is to be understood that the process 700 can be performed by any component or combination of components of the systems described herein. Similarly, any step, portion of a step, or combination of steps in the process 700 can be performed by any component or combination of components of the systems described herein. The process 700 is an example and not intended to limit the scope of the disclosure. The process 700 can be altered, e.g., by having steps added, removed, rearranged, combined and/or performed concurrently.

The process 700 begins at step 705 where the system receives electronically from a flow probe, flow rate data corresponding to an amount of infusion fluid administered to a subject. In some embodiments, the amount of the infusion fluid administered is configured to alter or maintain a physiological state of the subject. At step 710, the processor calculates, using the flow rate data, a subsequent administration protocol. At step 715, the processor generates a recommendation corresponding to the subsequent administration protocol. In some embodiments, the recommendation comprises a visual, audio, or textual presentation of the amount and/or duration of administration for a health care provider to manually act on or ignore.

In some embodiments, the representation is provided on a user interface which corresponds to the fluid administration protocol for the health care provider. The user interface provides a visual, audio, or textual adaptation of the subsequent administration protocol for which the healthcare provider has full discretion as to comply or not.

In some embodiments, the administration protocol corresponds to providing an infusion of a fluid to the subject at a rate corresponding to a gravity-assisted delivery system, such as an IV bag. The administration protocol can be an electronic signal to a monitor or display (a user interface) to provide graphical information or digitally created language that functions as a recommendation to the clinician as to subsequent fluid administrations, or the electronic signal can be presented to a flow controller to stop a fluid bolus currently being administered, or to continue a current action and continue to acquire physiological data and/or mass flow (rate) parameters, or to start a new fluid bolus, modify and/or or continue an existing fluid bolus or medication administration if one is being administered and/or to provide a maximum fluid bolus. The received physiological data can be used by a processor with an algorithm to provide parameters ("physiological parameters") such as hemodynamic data, e.g., cardiac output, stroke volume, heart rate, blood pressure and arterial pressure, for example.

In some implementations, the user interface provides a recommendation regarding a subsequent administration protocol. In some implementations, the user interface provides a recommendation regarding the subsequent administration protocol and is configured to receive a user input, e.g., indicating acceptance or rejection of the intervention command and for which the system provides an electronic signal to the flow controller. For example, a selection of fluid volume rates can be presented for the user to select/accept, or for the user to input a specific value using a keyboard. Additional graphical displays or representations can be employed and may comprise a standard "Starling Curve" of ventricular function, a graphical indicator of where the subject is perceived to be presently along that curve, and a band showing the ideal range of the curve for the subject, among other representations. In addition, minimum and maximum curves can be displayed showing the observed ranges of cardiac function in a given subject (not shown).

Figure 8:
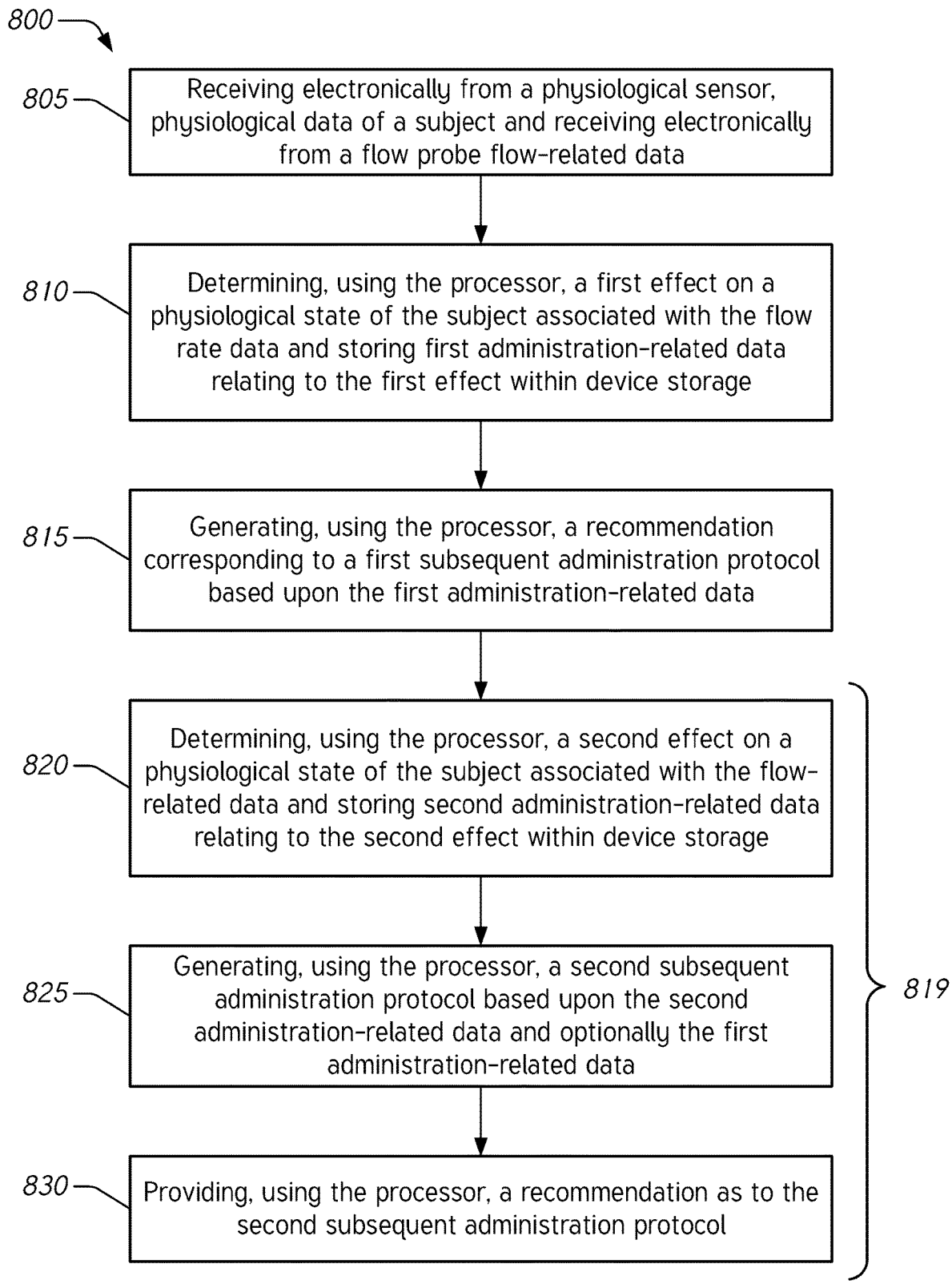
FIG. 8 is a flow chart of another example method as disclosed and described herein.

FIG. 8 illustrates a flowchart of an example process 800 for providing assisted delivery management in combination with the systems, apparatuses, and methods disclosed herein. The process 800 can be performed by any of the subject monitoring systems 100a-100f respectively illustrated in FIGS. 1A-1F and FIG. 2 and/or the systems 300a, 300b, 400a, 400b respectively illustrated in FIGS. 3A, 3B, 4A, and 4B. Accordingly, for ease of description, the process 800 is described as being performed by the system and/or a processor of the system. However, it is to be understood that the process 800 can be performed by any component or combination of components of the systems described herein. Similarly, any step, portion of a step, or combination of steps in the process 800 can be performed by any component or combination of components of the systems described herein. The process 800 is an example and not intended to limit the scope of the disclosure. The process 800 can be altered, e.g., by having steps added, removed, rearranged, combined and/or performed concurrently.

The process 800 begins at step 805 where the system receives electronically from a physiological sensor, physiological data and receives electronically from a flow probe, flow related data. The flow related data corresponds to an amount of fluid administered to a subject. In some embodiments, the amount of the fluid administered is configured to alter or maintain a physiological state of the subject. At step 810, the processor determines a first effect on a physiological state of the subject associated with the flow related data and stores first administration related data relating to the first effect within device storage. At step 815, the processor generates a recommendation corresponding to a subsequent administration protocol based upon the first administration related data. In some embodiments, the recommendation comprises a visual, audio, or textual presentation of the amount and/or duration of administration for a health care provider to manually act on or ignore.

Optional steps 819 (encompassing steps 820, 825, and 830) includes step 820 where the processor determines a second effect on a physiological state of the subject associated with the flow related data and stores second administration related data relating to the second effect within device storage. At step 825, the processor generates a second subsequent administration protocol based upon the second administration related data and optionally the first administration related data. At step 830, the processor provides a recommendation as to the second subsequent administration protocol in a manner similar to that described above.

Figure 9:
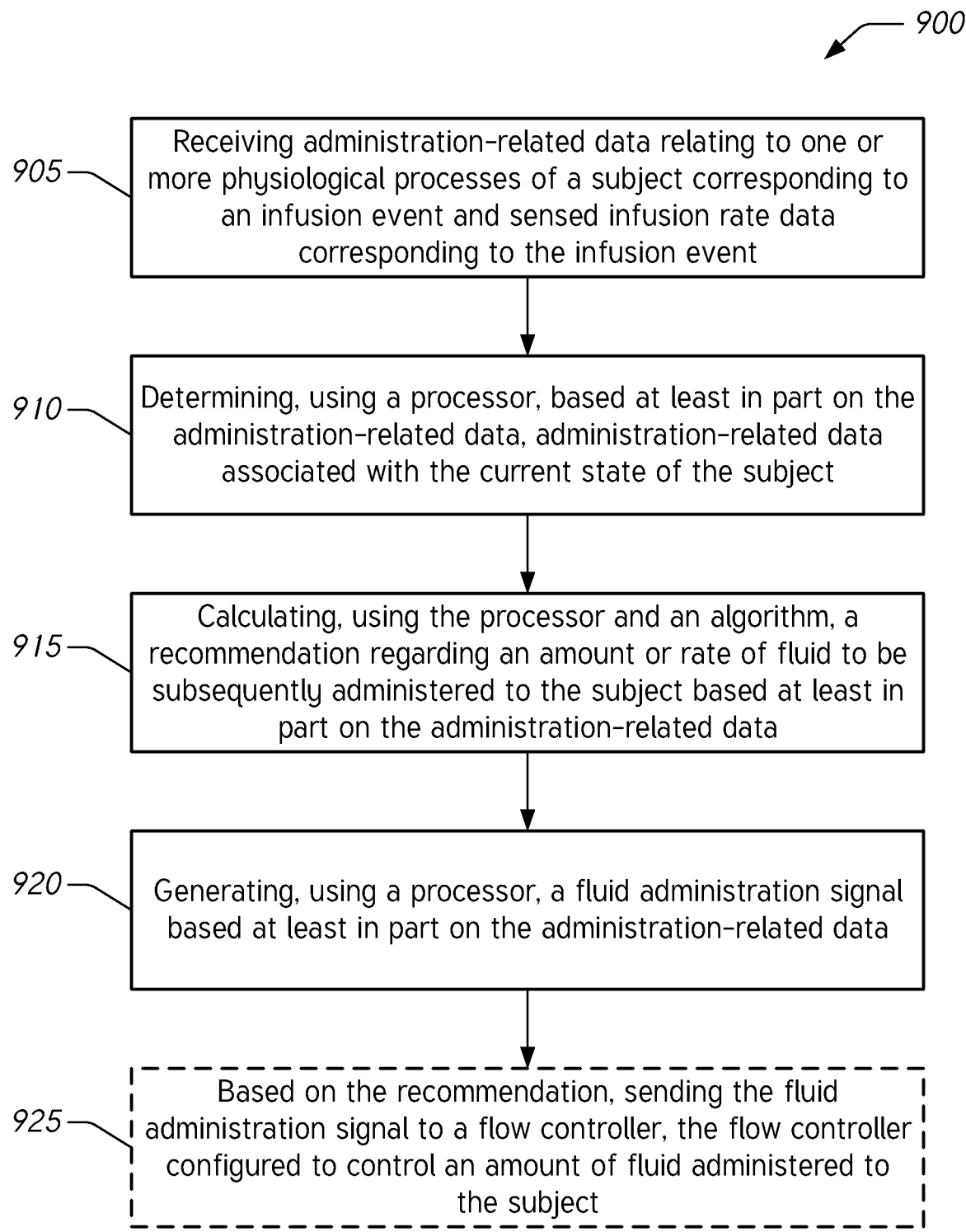
FIG. 9 is a flow chart of another example method as disclosed and described herein.

FIG. 9 illustrates a flowchart of another example process 900 for providing assisted fluid delivery management in combination with the systems, apparatuses, and methods disclosed herein. The process 900 can be performed by any of the subject monitoring systems 100a-100f respectively illustrated in FIGS. 1A-1F and FIG. 2 and/or the systems 300a, 300b, 400a, 400b respectively illustrated in FIGS. 3A, 3B, 4A, and 4B. Accordingly, for ease of description, the process 900 is described as being performed by the system and/or a processor of the system. However, it is to be understood that the process 900 can be performed by any component or combination of components of the systems described herein. Similarly, any step, portion of a step, or combination of steps in the process 900 can be performed by any component or combination of components of the systems described herein. The process 900 is an example and not intended to limit the scope of the disclosure. The process 900 can be altered, e.g., by having steps added, removed, rearranged, combined and/or performed concurrently.

The process 900 starts at step 905 where the system (e.g., a processing module) using sensor input data receives administration-related data relating to one or more physiological processes of a subject corresponding to an infusion event and sensed infusion rate data corresponding to the infusion event. At step 910, the system can then determine, using a processor, and based at least in part upon the administration-related data, administration-related data associated with the current state of the subject. For example, the current state can be a hemodynamic state. At step 915, the processor in combination with an algorithm, can calculate an amount of fluid to be administered to the subject based at least in part upon the administration-related data. At step 920, the processor can generate a fluid administration signal based at least in part upon the first administration-related data. At step 925, the administration signal can optionally be sent to a flow controller, the flow controller configured to control an amount of infusion fluid to be administered to the subject.

The process 900 can be configured such that the user interface receives user input indicating acceptance or rejection of the fluid administration signal, where upon acceptance of the fluid administration signal a control signal for the flow controller is generated.

In some embodiments, the processor can be configured to calculate a predicted change in the subject's physiological parameter. A predicted change in the physiological parameter in response to administration of a first or second bolus to the subject can be determined using a process based at least in part on one or more of a subject-population database or a patient history record.

Figure 10:
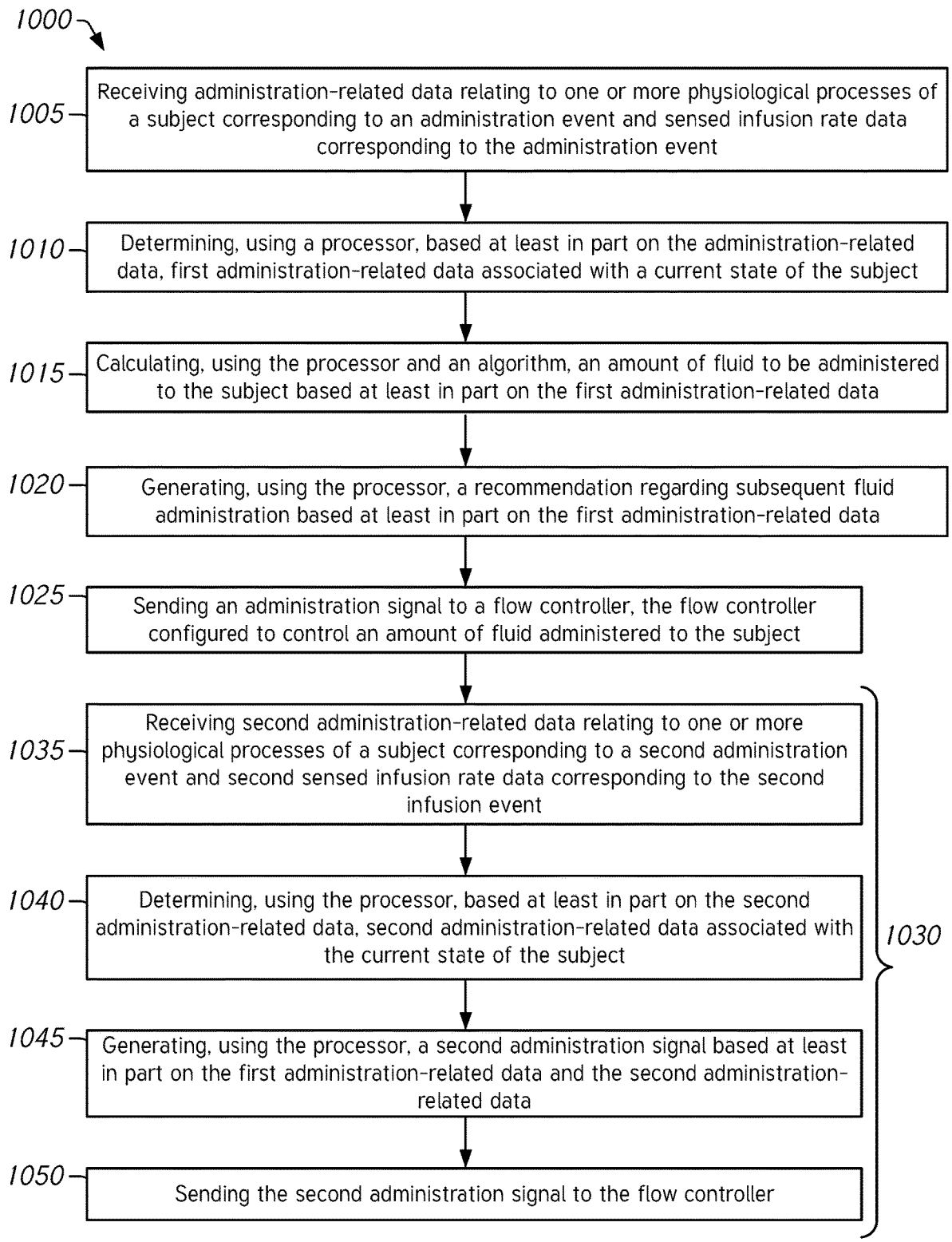
FIG. 10 is a flow chart of another example method as disclosed and described herein.

FIG. 10 illustrates a flowchart of an example process 1000 for providing assisted fluid delivery management in accordance with the systems, apparatuses, and methods disclosed herein. The process 1000 can be performed by any of the subject monitoring systems 100a-100f respectively illustrated in FIGS. 1A-1F and FIG. 2 and/or the systems 300a, 300b, 400a, 400b respectively illustrated in FIGS. 3A, 3B, 4A, and 4B. Accordingly, for ease of description, the process 1000 is described as being performed by the system and/or a processor of the system. However, it is to be understood that the process 1000 can be performed by any component or combination of components of the systems described herein. Similarly, any step, portion of a step, or combination of steps in the process 1000 can be performed by any component or combination of components of the systems described herein. The process 1000 is an example and not intended to limit the scope of the disclosure. The process 1000 can be altered, e.g., by having steps added, removed, rearranged, combined and/or performed concurrently.

The process 1000 begins at step 1005 where the system (e.g., a processing module) using sensor input data receives administration-related data relating to one or more physiological processes of a subject corresponding to an administration event and sensed infusion rate data corresponding to the administration event. At step 1010, the system can then determine, using a processor, and based at least in part upon the administration-related data, first administration-related data associated with the current state of the subject. For example, the current state can be a hemodynamic state. At step 1015, the processor in combination with an algorithm, calculates an amount of fluid to be administered to the subject based at least in part upon the first administration-related data. At step 1020, the processor generates a recommendation regarding subsequent fluid administration based at least in part on the first administration-related data. At step 1025, an administration signal can be sent to a flow controller, the flow controller configured to control an amount of infusion fluid to be administered to the subject.

In some embodiments, process 1000 can further provide additional processing steps 1030. At step 1035, second administration-related data can be received relating to one or more physiological processes of a subject corresponding to a second administration event and second sensed infusion rate corresponding to the second administration event. At step 1040, the processor can determine, based at least in part upon the second administration-related data, second administration-related data associated with the current state of the subject. At step 1045, the processor can generate a second administration signal based at least in part on the first administration-related data and the second administration-related data. At Step 1050, the second fluid administration signal can be sent to the flow controller. The physiological processes of a subject can provide, or be used to calculate, one or more parameters such as of cardiac output, stroke volume, etc. The mass flow (rate) parameter can include total volume or rate.

Figure 11:
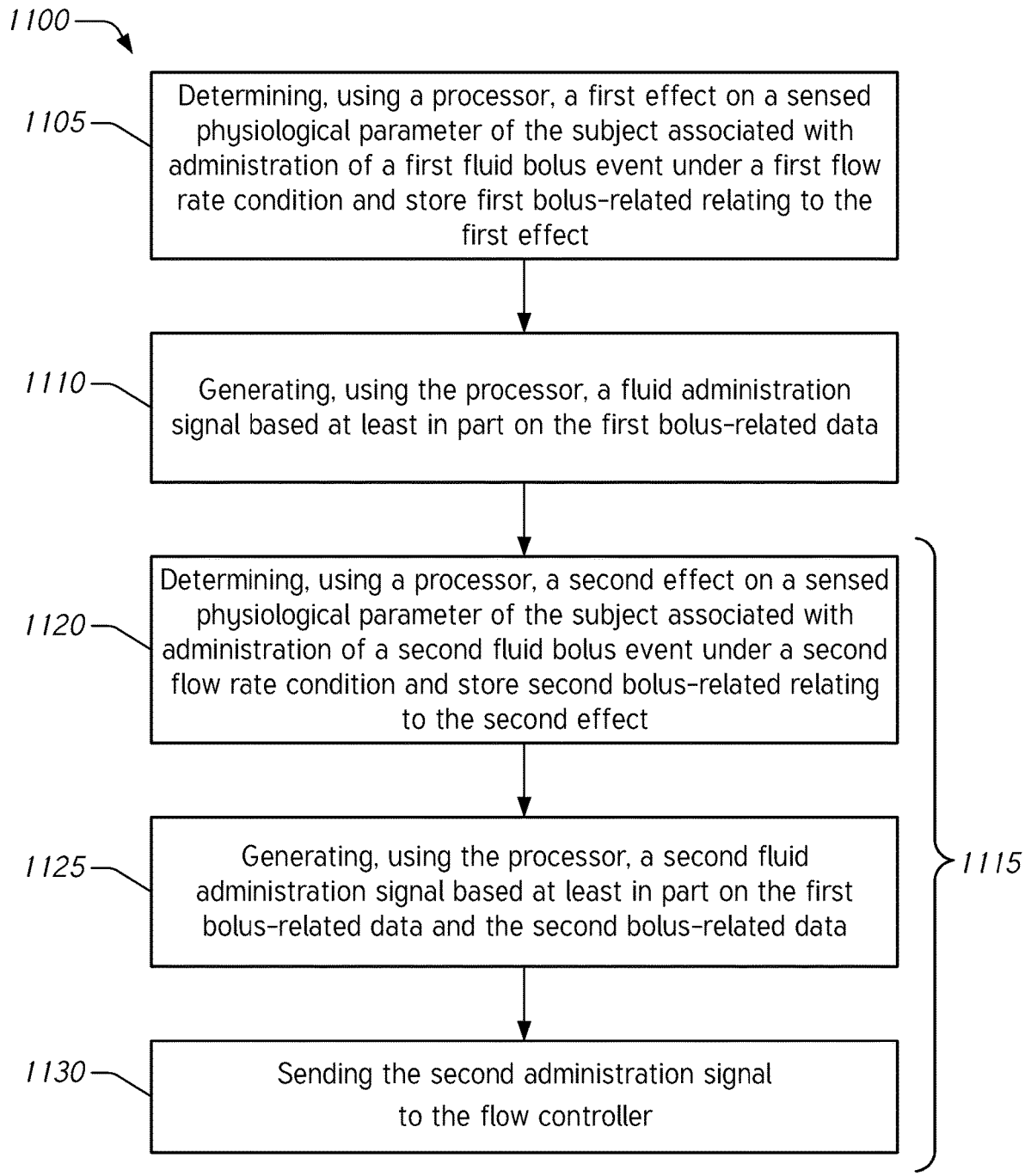
FIG. 11 is a flow chart of another example method as disclosed and described herein.

FIG. 11 illustrates a flowchart of an example process 1100 for providing assisted fluid delivery management in accordance with the systems, apparatuses, and methods disclosed herein. The process 1100 can be performed by any of the subject monitoring systems 100a-100f respectively illustrated in FIGS. 1A-1F and FIG. 2 and/or the systems 300a, 300b, 400a, 400b respectively illustrated in FIGS. 3A, 3B, 4A, and 4B. Accordingly, for ease of description, the process 1100 is described as being performed by the system and/or a processor of the system. However, it is to be understood that the process 1100 can be performed by any component or combination of components of the systems described herein. Similarly, any step, portion of a step, or combination of steps in the process 1100 can be performed by any component or combination of components of the systems described herein. The process 1100 is an example and not intended to limit the scope of the disclosure. The process 1100 can be altered, e.g., by having steps added, removed, rearranged, combined and/or performed concurrently.

The process 1100 starts at step 1105 where the processor, e.g., a processor module, determines a first effect on the sensed physiological parameter of the subject associated with administration to the subject of a first fluid bolus event under a first flow rate condition, and then stores, using the processor first bolus related data relating to the first effect corresponding to the first flow rate condition. The first effect is determined by analyzing signals received from a physiological sensor and a flow probe and can include additional external and internal physiological information relating to the patient's physiological status, or the additional external information can be subject-population data, patient-specific or historical information stored in a computer readable storage medium or in accessible memory. The first bolus-related data relating to the first effect can be stored in accessible memory, such as RAM, ROM, flash or other type of computer readable storage medium. At step 1110, the processor generates a fluid administration signal based at least in part upon the first bolus-related data where the fluid administration signal is usable to assist in administration fluid to the subject. In some embodiments, the processor sends the first fluid administration signal to a flow controller, the flow controller configured to control an amount of infusion fluid administered to a subject In some embodiments, process 1100 can further provide additional processing steps 1115. For example, at step 1120, the processor determines a second effect on the sensed physiological parameter of the subject associated with an administration to the subject of a second fluid bolus event corresponding to a second flow rate condition and then stores, using the processor, second bolus-related data relating to the second effect corresponding to the second flow rate condition. In some embodiments, the second fluid bolus corresponds to infusion of a fluid to the subject at an infusion rate that is the same or different from the first fluid bolus. At step 1125, the processor generates a second fluid administration signal based at least in part upon the first administration-related data and the second administration-related data, where the second fluid administration signal is usable to assist in administration of fluid to the subject. At step 1130, the processor sends the second fluid administration signal to the flow controller.

In some embodiments, the processor and an algorithm are configured to generate a representation of an intervention parameter on a user interface corresponding to the first and/or second fluid administration signals. A user interface can be configured to receive user input indicating acceptance or rejection of the intervention parameter. Responsive to an acceptance of the intervention parameter, the processor can generate a control signal for the flow controller. The algorithm can be used to determine one or more intervention commands and present such commands, e.g., as options to the user on a monitor or its display. The intervention commands can include, for example, the type of fluid bolus to administer, an amount of fluid bolus to administer, a rate and time over which to administer the fluid bolus, and/or a start/stop option.

The methods described herein are configured for assisted delivery hemodynamic management in combination with the systems and apparatuses disclosed herein. Accordingly, the disclosed methods can be performed by any of the subject monitoring systems 100a-100f respectively illustrated in FIGS. 1A-1F and FIG. 2 and/or the systems 300a, 300b, 400a, 400b respectively illustrated in FIGS. 3A, 3B, 4A, and 4B. For example, the processing module 541 (described herein with reference to FIG. 2) can receive administration-related data relating to one or more physiological parameters of the subject. The administration-related data can be received from one or more of the physiological or HD sensor 204 and flow probe 119 or from user input received through interaction with the monitor 310 by way of the graphics engine 549. Upon receiving the administration-related data, the processing module 541 stores administration-related information corresponding to the administration-related data in in accessible memory, such as RAM, ROM, flash or other type of computer readable storage medium. The algorithm 107, using one or more of subject-population data, patient specific data, and/or historic data and the administration-related data, can determine, based at least in part upon the administration-related data, a predicted change in a physiological parameter of the subject 120 in response to administration of a fluid bolus to the subject. The algorithm 107 provides a fluid administration recommendation in response to the predicted change to the graphics engine 549 or monitor 310 on a display or user interface. The user can then respond with a response relating to the recommendation from the algorithm 107. The algorithm 107 can receive user input relating to a recommendation and generate an administration signal related to the recommendation that is sent to the flow controller 301. Alternatively, the fluid administration recommendation can be converted to a signal to cause the fluid flow controller 301 to administer the recommendation automatically.

Another example method for assisted delivery hemodynamic management now described can be used in combination with the systems and apparatuses disclosed herein. For example, the method can be performed by any of the subject monitoring systems 100a-100f respectively illustrated in FIGS. 1A-1F and FIG. 2 and/or the systems 300a, 300b, 400a, 400b respectively illustrated in FIGS. 3A, 3B, 4A, and 4B. The method can include using a processing module for determining a first effect on a physiological parameter of the subject associated with administration to the subject of a first fluid bolus corresponding to a first mass flow parameter and storing a first administration-related data relating to the first effect in accessible memory, such as RAM, ROM, flash or other type of computer readable storage medium. In some embodiments, the first effect corresponds to providing an infusion of a fluid to the subject at a rate of about 2 L/hr to about 6 L/hr. The processing module can then determine a second effect on a physiological parameter of the subject associated with administration to the subject of a second fluid bolus corresponding to a second mass flow or fluid flow rate parameter, and store second administration-related data relating to the second effect in accessible memory, such as RAM, ROM, flash or other type of computer readable storage medium. In some embodiments, the second fluid bolus corresponds to infusion of a fluid to the subject at an infusion rate that is the same or different from the first fluid bolus. A fluid administration signal and/or a fluid administration recommendation can then be determined and provided based at least in part upon at least one of the first effect and the second effect in combination with one or more of subject-population data, historical data, and patient-specific data. The recommendation can be provided to the user on a user interface for acceptance or rejection of the recommendation. In some embodiments, the fluid administration recommendation can be converted to a signal to cause the fluid flow controller to administer the recommendation automatically.

Any infusion fluid known in the art can be used in conjunction with the present system and the disclosed physiological sensors. The IV solution can contain a medicament, such as but not limited to heparin and/or vasodilators and/or cardiac-related medications.

In some embodiments, one, two, or more solutions can be used in conjunction with the disclosed systems. For example, in some embodiments, two or more solutions can be used or administered to the subject concurrently, intermittently, or independently. In some embodiments, the infusion fluid is an isotonic saline solution containing a sufficient concentration of an anticoagulant to substantially prevent blood clotting in and/or near a catheter (not shown) and/or a physiological sensor, and/or a sufficient concentration of or antimicrobial to substantially prevent infection in and/or near the catheter or other insertion device (not shown).

It is generally known that, for a variety of reasons, there may be a delay in correlation between a hemodynamic parameter acquisition event and that of a bolus infusion, e.g., the measured mass flow amount or rate of infusate corresponding to the onset, peak, and or decay profile of a hemodynamic response. The system is configurable to compensate and/or adjust for the "lag" of the flow probe data with that of the sensed hemodynamic data using correction factors empirically or experimentally determined, or historic data.

Example Methods of Controlling Liquid Flow to a Subject

Figure 12:
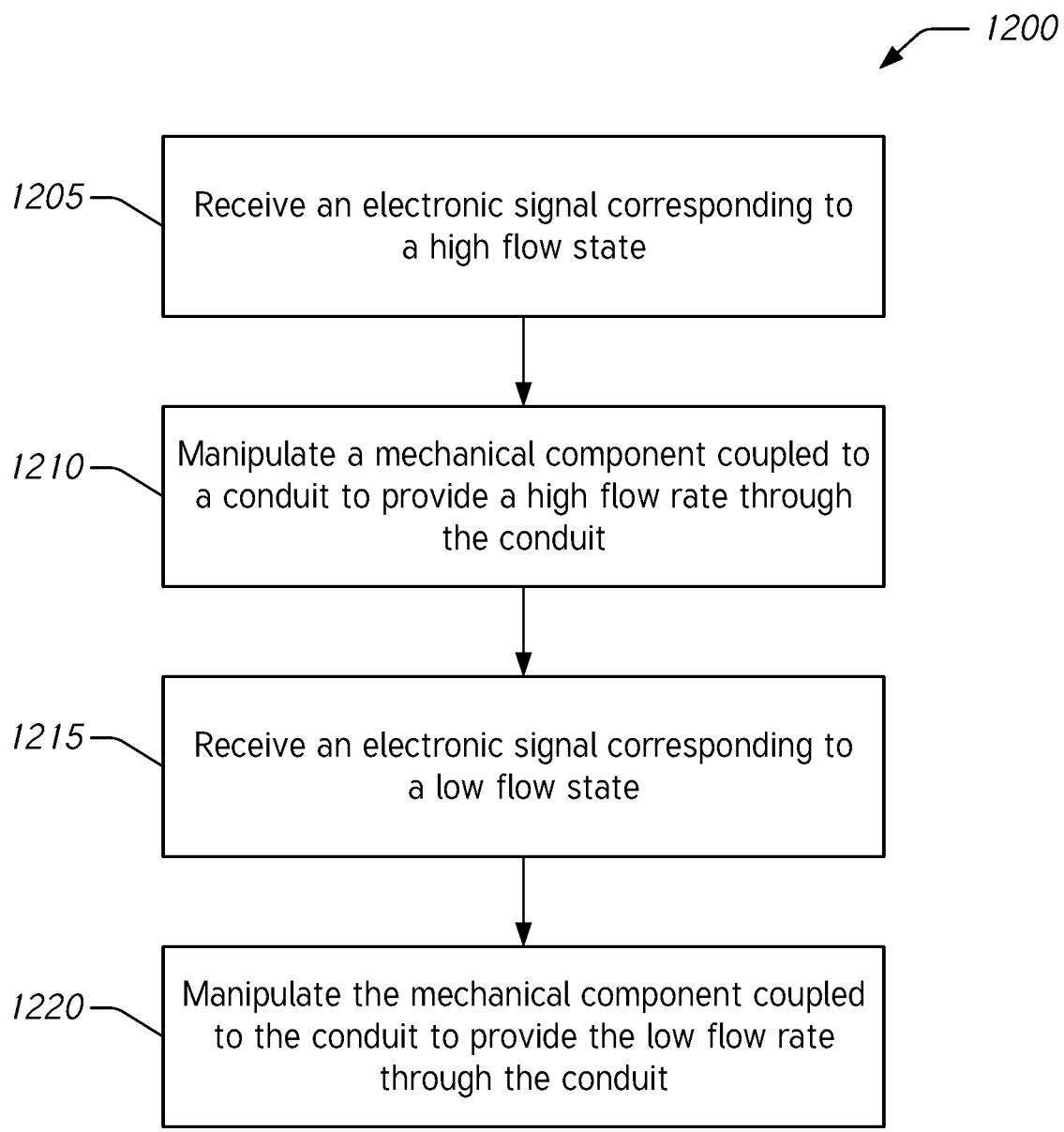
FIG. 12 is a flow chart of an example method for automating the delivery of high-flow rates and low-flow rates to a subject.

FIG. 12 illustrates a flow chart of an example method 1200 for controlling the flow of liquid to a subject using the flow controllers described herein. The method 1200 can be performed using any of the flow controllers and/or monitoring systems described herein, such as the devices and systems described herein with reference to FIGS. 6A-6E. The method 1200 is advantageous because it provides a high flow state for providing fluid boluses and an uninterrupted low flow state to prevent or reduce blood clots.

The method 1200 can be performed by any of the devices or systems described herein. For ease of description, the method 1200 is described as being performed by the flow controller 301a of FIG. 5A. However, it is to be understood that the subject monitoring systems 100a-100f of FIGS. 1A-1F and 2, the systems 300a, 300b, 400a, 400b of FIGS. 3A, 3B, 4A, and 4B, and/or the flow controllers 301a-301e described herein with reference to FIGS. 6A-6E can perform the method 1200. It is also to be understood that any component, subsystem, device, or apparatus of the systems 100a-100f of FIGS. 1A-1F and 2, the systems 300a, 300b, 400a, 400b of FIGS. 3A, 3B, 4A, and 4B, and/or the flow controllers 301a-301e described herein with reference to FIGS. 6A-6E can perform any portion of a step, any individual step, or any combination of steps in the method 1200. Similarly, any combination of components, subsystems, devices, or apparatuses of the systems 100a-100f of FIGS. 1A-1F and 2, the systems 300a, 300b, 400a, 400b of FIGS. 3A, 3B, 4A, and 4B, and/or the flow controllers 301a-301e described herein with reference to FIGS. 6A-6E can perform any portion of a step, any individual step, or any combination of steps in the method 1200.

In step 1205, the flow controller receives an electronic signal corresponding to a high flow state. The electronic signal can be sent by a monitor or other device running an algorithm. The electronic signal can be initiated by a clinician indicating that a bolus is to be delivered to a subject. The electronic signal can be initiated by an algorithm that determines that it is desirable or appropriate to deliver a bolus to a subject. In some embodiments, this determination can be approved by a clinician.

In step 1210, the flow controller manipulates a mechanical component coupled to a conduit to provide a high flow rate through the conduit. The conduit can be internal to the flow controller or it can be a conduit that runs from a fluid source (e.g., an IV bag) to a subject. The mechanical component can be a valve, a pinch valve, a switch, or the like as described herein. Manipulating the mechanical component can include releasing a conduit so that an inner diameter and/or cross-section of the conduit expands relative to a low flow state, unblocking a high flow path so that the fluid flows through the high flow path (instead of or in addition to flowing through the low flow path), or the like.

In step 1215, the flow controller receives an electronic signal corresponding to a low flow state. The electronic signal can be sent by a monitor or other device running an algorithm. The electronic signal can be initiated by a clinician to terminate delivery of a bolus. The electronic signal can be initiated by an algorithm that determines that it is desirable or appropriate to terminate delivery of a bolus. In some embodiments, this determination can be approved by a clinician.

In step 1220, the flow controller manipulates the mechanical component coupled to the conduit to provide a low flow rate through the conduit. Manipulating the mechanical component can include restricting a conduit so that an inner diameter and/or cross-section of the conduit reduces relative to the high flow state, blocking the high flow path so that the fluid flows through the low flow path, or the like.

Example Methods of Detecting and Tracking Fluid Boluses

Figure 13:
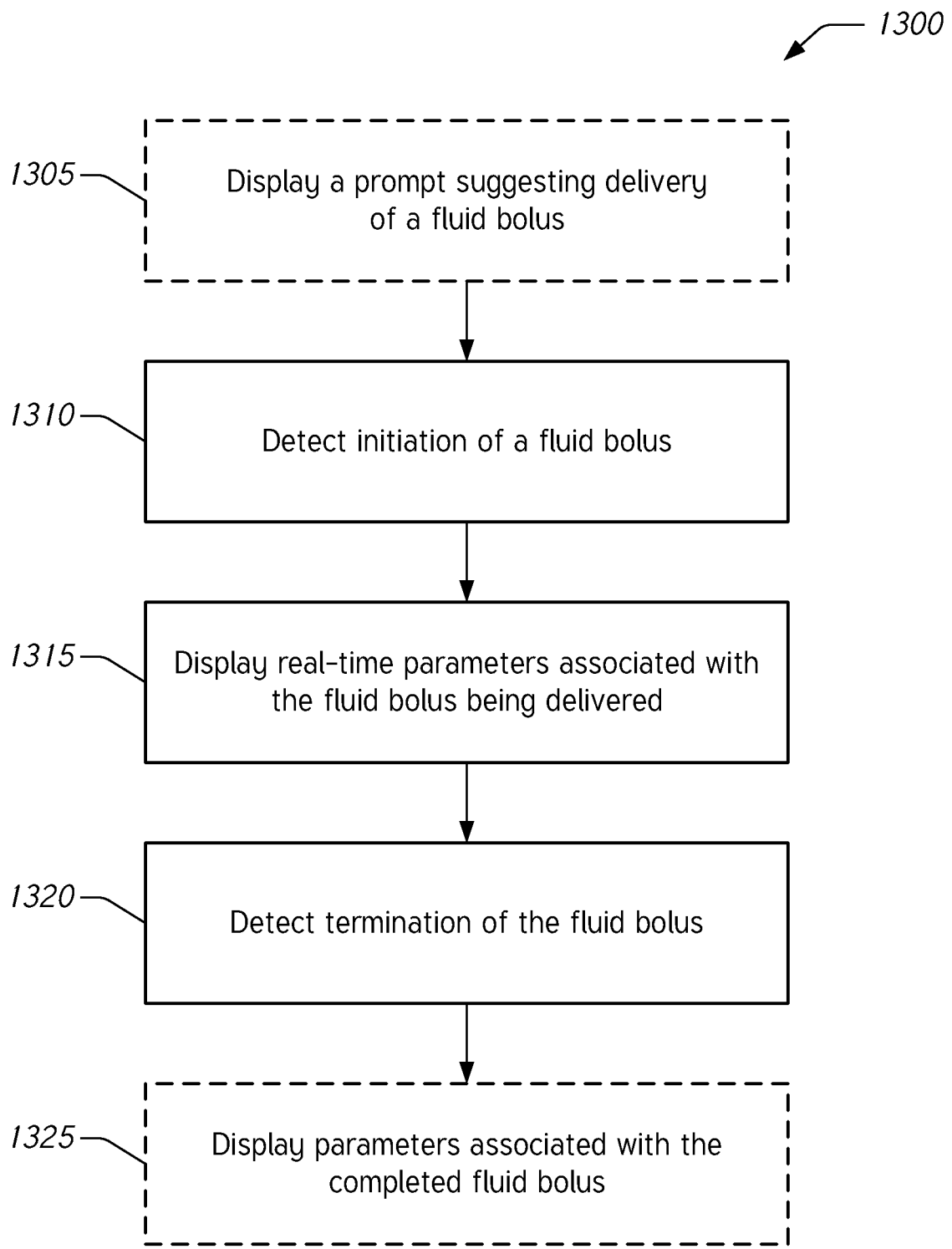
FIG. 13 is a flow chart of an example method for automatically detecting and tracking a fluid bolus.
Figure 14A:
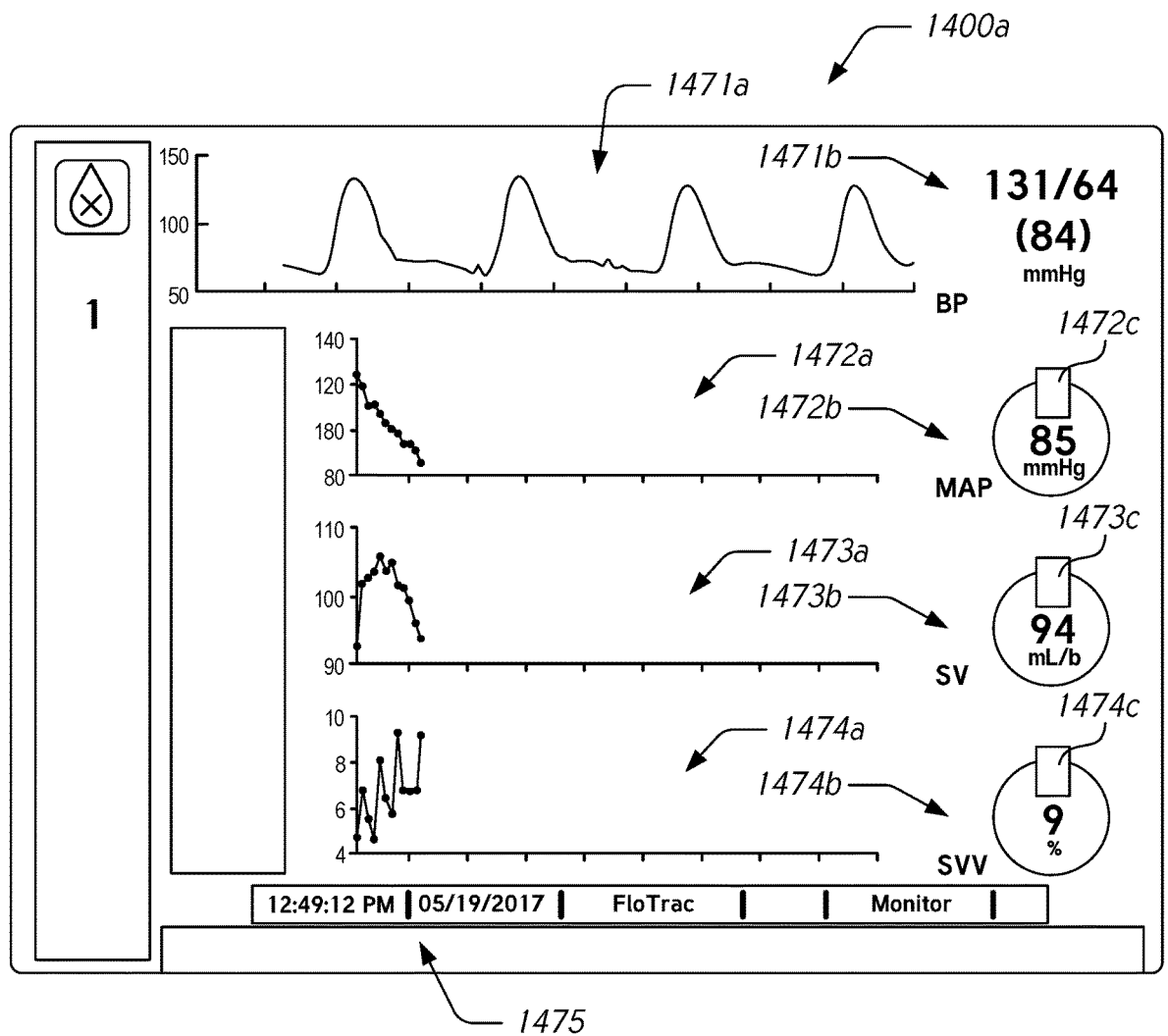
FIGS. 14A, 14B, 14C, and 14D illustrate example displays of user interfaces related to the automatic detection and tracking of a fluid bolus.
Figure 14B:
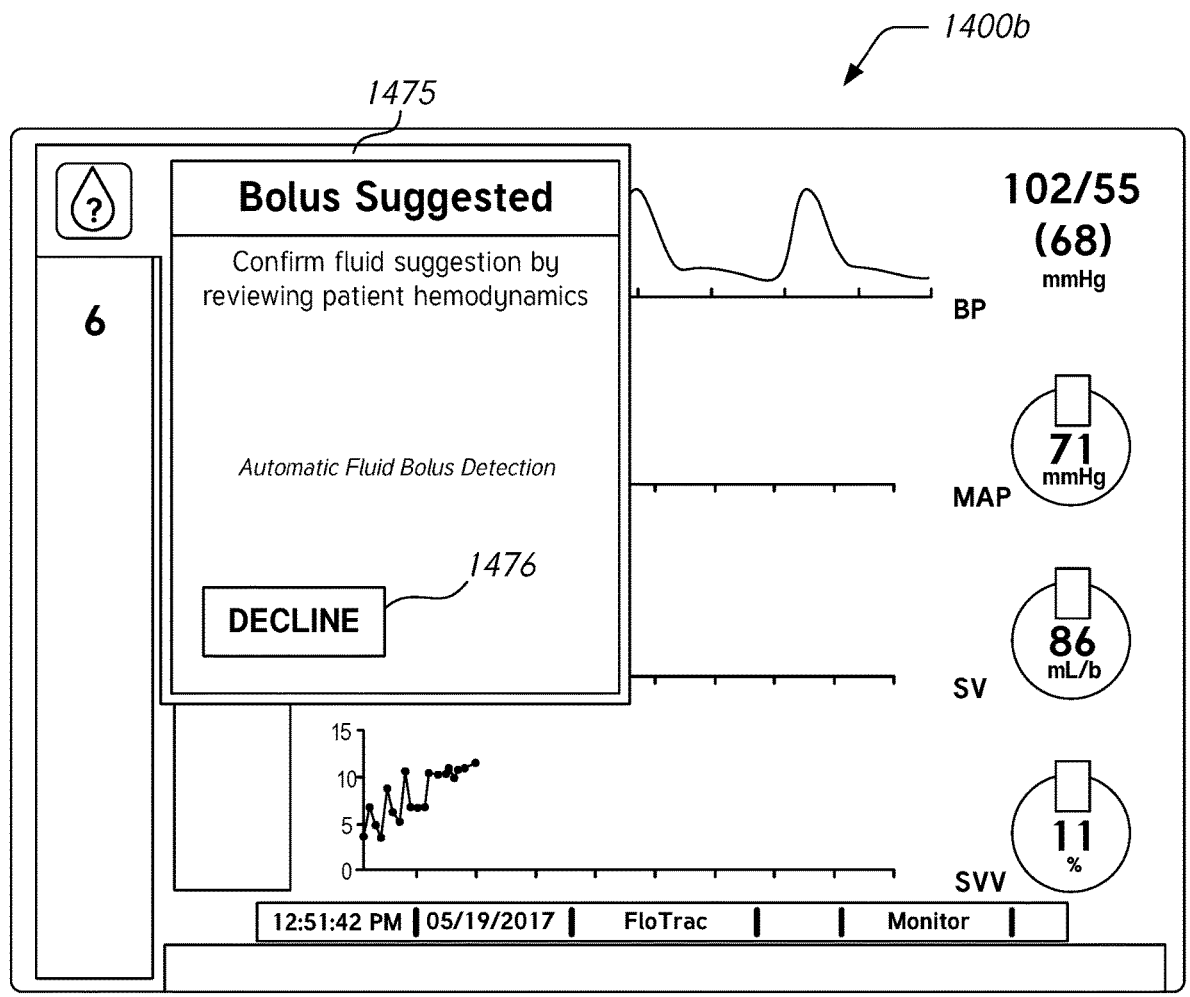
Figure 14C:
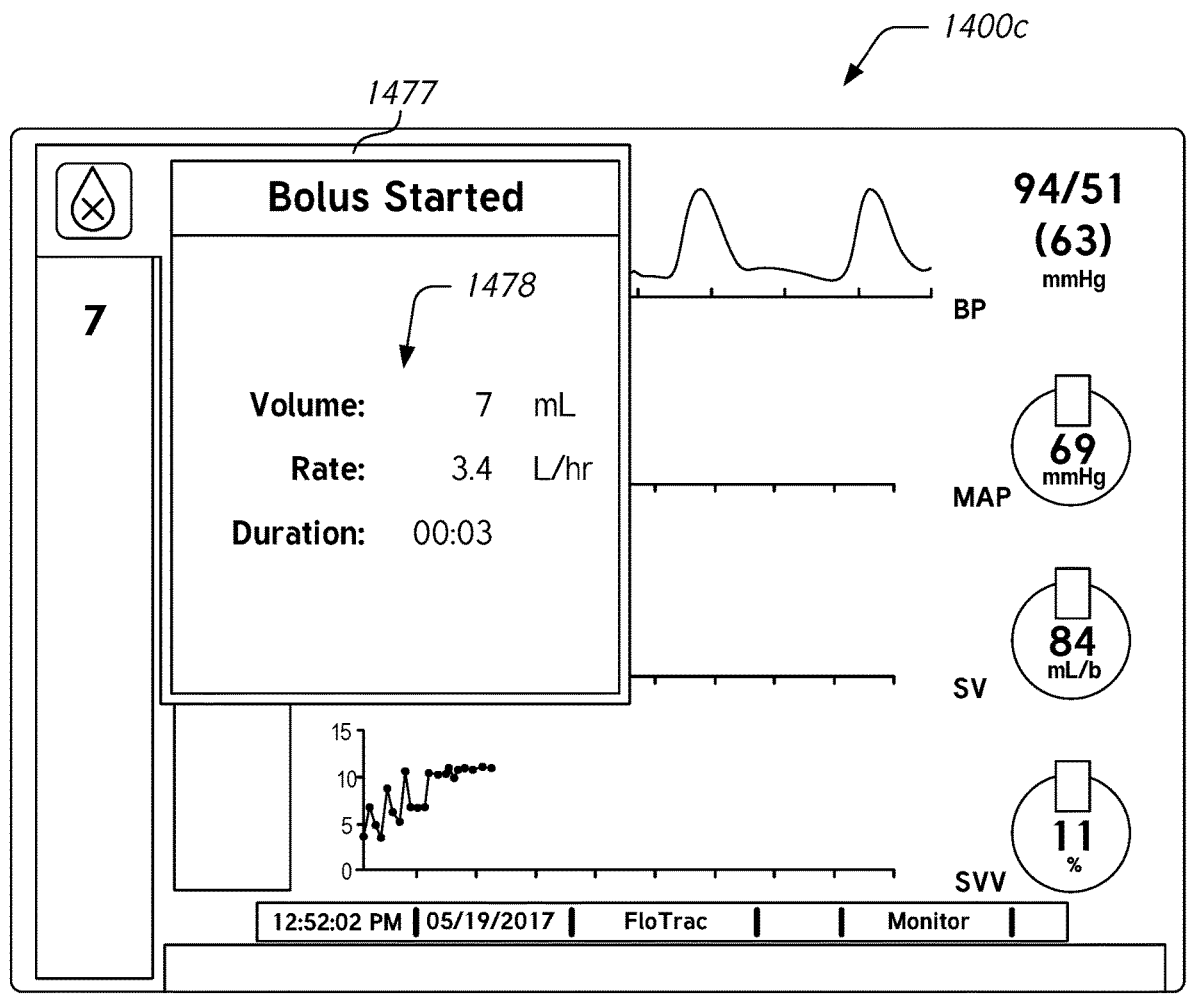
Figure 14D:
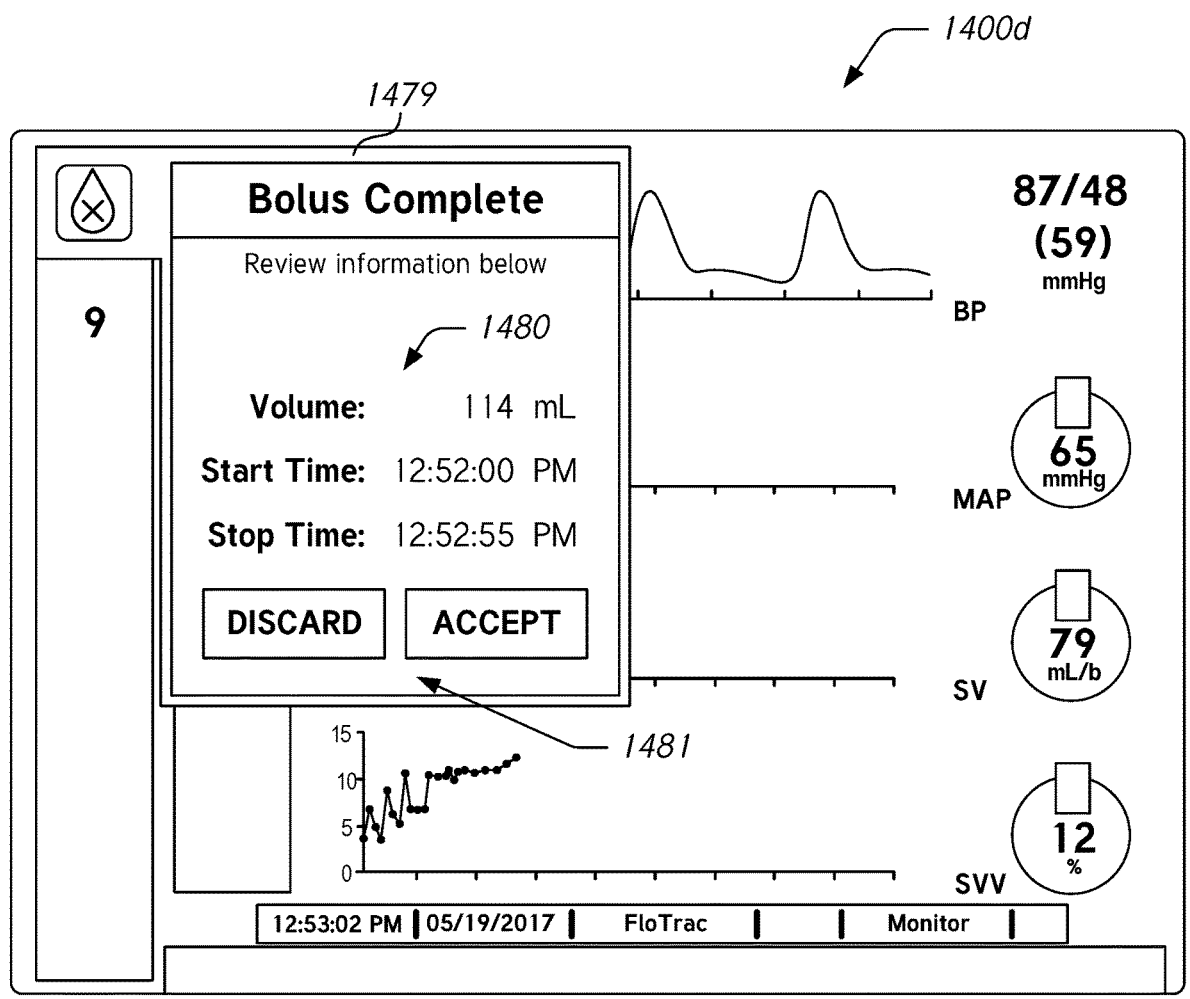

FIG. 13 illustrates a flow chart of an example method 1300 for detecting and tracking fluid boluses using the flow probes, monitors, and algorithms described herein. The method 1300 can be performed using any of the flow probes and/or monitoring systems described herein, such as the devices and systems described herein with reference to FIGS. 1A-1F, 2, 3A, 3B, 4A, 4B, and 14A-14D. The method 1300 is advantageous because it prompts for delivery of a bolus and automatically tracks parameters associated with the fluid bolus, eliminating potential errors arising from manually tracking the fluid bolus.

The method 1300 can be performed by any of the devices or systems described herein. For ease of description, the method 1300 is described as being performed by the monitor 310 of FIG. 1A. However, it is to be understood that the subject monitoring systems 100a-100f of FIGS. 1A-1F and 2, the systems 300a, 300b, 400a, 400b of FIGS. 3A, 3B, 4A, and 4B, and/or the displays 1400a-1400d described herein with reference to FIGS. 14A-14D can perform the method 1300. It is also to be understood that any component, subsystem, device, or apparatus of the systems 100a-100f of FIGS. 1A-1F and 2, the systems 300a, 300b, 400a, 400b of FIGS. 3A, 3B, 4A, and 4B, and/or the displays 1400a-1400d described herein with reference to FIGS. 14A-14D can perform any portion of a step, any individual step, or any combination of steps in the method 1300. Similarly, any combination of components, subsystems, devices, or apparatuses of the systems 100a-100f of FIGS. 1A-1F and 2, the systems 300a, 300b, 400a, 400b of FIGS. 3A, 3B, 4A, and 4B, and/or the displays 1400a-1400d described herein with reference to FIGS. 14A-14D can perform any portion of a step, any individual step, or any combination of steps in the method 1300.

In optional step 1305 (indicated using a box with dashed lines), the monitor displays a prompt suggesting delivery of a fluid bolus. The monitor can run an algorithm, as described herein, that determines when to display the prompt. The determination can be made based at least in part on measured hemodynamic parameters, time since last bolus delivery, a configuration set by a clinician, or a combination of these. The displayed prompt can be configured to receive input from a user interface to decline delivery of the fluid bolus. In such an instance, the algorithm returns to a starting condition to determine when to display the prompt suggesting delivery of the fluid bolus. In some embodiments, the algorithm can be configured to wait a pre-determined amount of time before displaying the prompt again. In some embodiments, alternatively or additionally, a user initiates delivery of a bolus which the system detects and analyzes in the following steps. For example, the user can initiate delivery of a bolus without the monitor displaying a prompt suggesting delivery of a fluid bolus.

In step 1310, the monitor detects initiation of delivery of a fluid bolus. The monitor receives flow-related data from a flow probe, as described herein. The monitor can be configured to analyze this data to automatically determine initiation of a fluid bolus. This advantageously allows the clinician and/or others assisting in the procedure to be free from the responsibility of manually tracking properties of the fluid bolus.

The monitor can be configured to determine initiation of a fluid bolus using different techniques and/or algorithms, examples of which follow. These examples are not intended to describe all of the potential techniques for determining initiation of a fluid bolus. Rather, the description that follows is intended to illustrate various examples of techniques that can be employed individually or in combination. For example, the monitor can determine that a fluid bolus has been initiated when the flow rate exceeds a pre-determined threshold. As another example, the monitor can determine that a fluid bolus has been initiated when a moving average of the flow rate exceeds a pre-determined threshold. As another example, the monitor can determine that a fluid bolus has been initiated when a rate of change of the flow rate exceeds a pre-determined threshold. As another example, the monitor can determine that a fluid bolus has been initiated when a slope of the flow-related data (e.g., the flow rate over a period of time) exceeds a pre-determined threshold.

In some embodiments, the monitor can use wavelet analysis to determine initiation and/or termination of a fluid bolus. Wavelet analysis can be used by the monitor to detect the start and stop of a fluid bolus infusion and differentiate it from an on-going background maintenance fluid flow. Wavelet analysis advantageously allows accurate detection of sharp and sudden signal changes in a relatively noisy background environment. A discrete wavelet transform can be applied continuously on the flow signal to localize discontinuity-types of effects. For this purpose, the Haar wavelet, Daubechies wavelets, Symlet wavelets, and/or Biorthogonal wavelets may be used. The wavelet coefficients can be continuously or intermittently measured in real time for relatively sudden and relatively large changes that characterize a discontinuity in the signal.

Similarly, time-frequency analysis with continuous wavelet transform may be used. The time-frequency plot can show a large variation at points in time where a fluid bolus starts and/or stops. In addition, the short-time Fourier transform may be used to obtain a time-frequency spectrum as well. A simple fast Fourier transform (FFT)-based frequency analysis may be used in a continuous fashion to detect the appearance of high-frequency spectral components associated with the start and stop of a fluid bolus infusion.

Although the thresholds described herein have been described as pre-determined thresholds, the thresholds may change or be updated during operation. The changes may be automated or can be manually entered. In some embodiments, the pre-determined threshold can be adjusted by a user (e.g., clinician) during operation. This can be useful when it is desirable or advantageous to customize the sensitivity and/or specificity of the detection of the start of the fluid bolus. Similarly, the pre-determined threshold can be adjusted by the monitor based on hemodynamic properties, flow-related data, user input, or a combination of these.

In step 1315, the monitor displays real-time parameters associated with the fluid bolus being delivered. The parameters that can be displayed include, for example and without limitation, flow rate, total fluid delivered since initiation of the fluid bolus, duration of the fluid bolus, start time of the fluid bolus, targeted volume to deliver, targeted duration of the fluid bolus, or any combination of these. In addition, the monitor can be configured to display hemodynamic properties to aid the clinician in assessing the fluid responsiveness of the subject.

In step 1320, the monitor detects termination of the fluid bolus. The monitor can be configured to analyze flow-related data from the flow probe to automatically determine termination of the fluid bolus. This advantageously allows the clinician and/or others assisting in the procedure to be free from the responsibility of manually tracking termination of the fluid bolus.

The monitor can be configured to determine termination of the fluid bolus using different techniques and/or algorithms, examples of which follow. These examples are not intended to describe all the potential techniques for determining termination of a fluid bolus. Rather, the description that follows is intended to illustrate various examples of techniques that can be employed individually or in combination. For example, the monitor can determine that a fluid bolus has been terminated when the flow rate falls below a pre-determined threshold for a pre-determined amount of time. As another example, the monitor can determine that a fluid bolus has been terminated when a moving average of the flow rate falls below a pre-determined threshold. As another example, the monitor can determine that a fluid bolus has been terminated when a rate of change of the flow rate is less than a pre-determined threshold. As another example, the monitor can determine that a fluid bolus has been terminated when a slope of the flow-related data (e.g., the flow rate over a period of time) falls below a pre-determined threshold.

Although the thresholds described herein have been described as pre-determined thresholds, the thresholds may change or be updated during operation. The changes may be automated or can be manually entered. In some embodiments, the pre-determined threshold can be adjusted by a user (e.g., clinician) during operation. This can be useful when it is desirable or advantageous to customize the sensitivity and/or specificity of the detection of the termination of the fluid bolus. Similarly, the pre-determined threshold can be adjusted by the monitor based on hemodynamic properties, flow-related data, user input, or a combination of these. The pre-determined threshold for determining termination of the fluid bolus can be different from the pre-determined threshold for determining initiation of the fluid bolus.

In some embodiments, the monitor can be configured to distinguish between a maintenance rate, a line flush, and a fluid bolus based at least in part on the volume of fluid delivered between the determined initiation and termination of fluid delivery. For example, the monitor can be configured to categorize the fluid delivery as a line flush where the volume of fluid delivered between the determined start time and the determined termination time is less than or equal to 20 mL. As another example, the monitor can be configured to categorize the delivery of fluid as a fluid bolus where the volume of fluid delivered between the determined start time and the determined termination time is greater than about 100 mL. As another example, the monitor can be configured to categorize the delivery of fluid as a maintenance rate where the volume of fluid over time is less than about 10 mL per kilogram ideal body weight per hour. In some embodiments, the fluid delivered between determined start and termination times can be categorized as a line flush where the volume is between about 5 mL and about 100 mL, categorized as a fluid bolus where the volume is greater than about 100 mL, and categorized as a maintenance volume outside these ranges.

In optional step 1325, the monitor displays parameters associated with the completed fluid bolus. The parameters can include, for example and without limitation, total fluid volume delivered, peak flow rate, average flow rate, minimum flow rate, duration of fluid bolus, start time of fluid bolus, end time of fluid bolus, or any combination of these. In addition, the monitor can be configured to display hemodynamic properties to aid the clinician in assessing the fluid responsiveness of the subject.

Examples of Automatic Detection and Tracking of a Fluid Bolus

FIGS. 14A, 14B, 14C, and 14D illustrate example user interfaces 1400a, 1400b, 1400c, 1400d displayed in relation to the automatic detection and tracking of a fluid bolus. The user interfaces can be displayed on the monitor 310 described herein with respect to FIGS. 1A-1F, 3A, 3B, 4A, and 4B. The monitor that displays the user interface receives signals from a hemodynamic sensor and a flow probe, analyzes the received signals using an algorithm, and displays the measurements on the user interface. In addition, the monitor is configured to display a prompt suggesting delivery of a fluid bolus, to detect initiation of the fluid bolus, to display real-time parameters associated with the fluid bolus, to detect termination of the fluid bolus, and to display parameters associated with the delivered fluid bolus. In addition, the monitor is configured to display hemodynamic parameters to aid the clinician in assessing the fluid responsiveness of the subject.

The user interface 1400a can include a display 1475 of operational parameters that indicate the current time, date, the types of sensors being used, and operational state. The user interface 1400a also includes multiple display elements configured to illustrate values of hemodynamic parameters as well as the values of the parameters over time. For example, the user interface 1400a includes a blood pressure (BP) graph 1471a of blood pressure over time and a BP element 1471b that displays the real-time value (or last-measured value) of the blood pressure.

Similarly, the user interface 1400a includes a mean arterial pressure (MAP) graph 1472a of mean arterial pressure over time and a MAP element 1472b that displays the real-time value (or last-measured value) of the blood pressure. The MAP element 1472b can also include a MAP indicator 1472c that can change appearance (e.g., color, flashing, brightness, etc.) to help a clinician assess how the measured value compares to a targeted range (e.g., whether it is within or outside a pre-determined range).

Similarly, the user interface 1400a includes a stroke volume (SV) graph 1473a of stroke volume over time and a SV element 1473b that displays the real-time value (or last-measured value) of the stroke volume. The SV element 1473b can also include a SV indicator 1473c that can change appearance (e.g., color, flashing, brightness, etc.) to help a clinician assess how the measured value compares to a targeted range (e.g., whether it is within or outside a pre-determined range).

Similarly, the user interface 1400a includes a stroke volume variation (SVV) graph 1474a of stroke volume variation over time and a SVV element 1474b that displays the real-time value (or last-measured value) of the stroke volume variation. The SVV element 1474b can also include a SVV indicator 1474c that can change appearance (e.g., color, flashing, brightness, etc.) to help a clinician assess how the measured value compares to a targeted range (e.g., whether it is within or outside a pre-determined range).

The monitor can include a processor and memory configured to execute instructions that automatically determine an appropriate or desirable time to deliver a fluid bolus. The user interface 1400b includes a prompt 1475 that suggests delivery of a fluid bolus. The prompt 1475 can include a user interface element 1476 that allows a user to decline the suggestion. In some embodiments, this causes the monitor to wait a programmed amount of time before displaying the prompt 1475 again, even when conditions are such that the monitor would otherwise display the prompt. This allows a user to decline the suggestion without being presented soon thereafter with another prompt for delivery of a fluid bolus.

In some embodiments, the monitor is configured to wait a pre-determined amount of time before issuing a command to a flow controller to initiate a fluid bolus. In various embodiments, the monitor does not initiate the fluid bolus through communication with a flow controller. In certain embodiments, the subject monitoring system includes a manual control of the fluid flow and the monitor is configured to wait for the user to decline the suggestion using the element 1476, to wait until detection of a fluid bolus, or to wait a programmed amount of time before dismissing the prompt 1475.

The monitor can include a processor and memory configured to execute instructions that automatically identify a start time and a stop time of a fluid bolus. Responsive to detecting initiation of a fluid bolus, the monitor displays the user interface 1400c that includes an initiation information box 1477. The initiation information box 1477 indicates that a start of the bolus has been detected as well as flow-related data 1478. The flow-related data 1478 includes the total volume delivered, the flow rate, and the duration of the fluid bolus. These values update in real-time.

Responsive to detecting termination of the fluid bolus, the monitor displays the user interface 1400*d* that includes a termination information box 1479. The termination information box 1479 includes that the fluid bolus has completed and instructs the clinician to review the measured data 1480. The measured data 1480 includes the total volume delivered, the start time, and the stop time of the fluid bolus. The termination information box 1479 includes user interface elements 1481 that allow a user to accept or discard the fluid bolus (e.g., allow or prevent the information from being used to inform the timing of future boluses). In some embodiments, these values can be manually entered.

The start and stop times of a fluid bolus can be determined based at least in part on a change in the flow rate through a conduit from a fluid source to the subject. For example, start time can be determined when a flow rate increases by a pre-determined rate within a pre-determined time. Similarly, stop time can be determined when a flow rate decreases by a pre-determined rate within a pre-determined time. The flow probe can provide data that the monitor uses to track the flow rate between the start time and the stop time to determine the volume of liquid delivered between those times. In some embodiments, start and stop times are determined based on an absolute value of a flow rate surpassing a threshold (for the start time) or falling below a threshold (for the stop time). In various embodiments, start and stop times are determined based on a slope or rate of change of the flow rate. In certain implementations, start and stop times are determined based on a combination of relative flow rate changes and instantaneous changes in flow rate.

In some embodiments, the process flow illustrated by FIGS. 14A-14D can operate without input from a user during the process. The user interfaces 1400*a*-1400*d* illustrate how the monitors described herein can provide information to a clinician. Such embodiments can prompt the clinician to deliver a fluid bolus. The monitor can then automatically detect delivery of a bolus and can display information regarding the fluid bolus while it is being delivered. This information can include for example start time, instantaneous flow rate, average flow rate, total volume delivered, volume left to be delivered, the volume deficit relative to a target delivery volume, and the like. When the monitor automatically detects an end time of the fluid bolus, information about the fluid bolus can be displayed on the display including such information as start time, stop time, and the volume of fluid delivered during the fluid challenge. In some embodiments, this procedure can be accomplished without the clinician or other personnel touching or otherwise providing input to the monitor.

Additional Embodiments

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the present specification supersedes and/or takes precedence over any such contradictory material of the incorporated reference.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described herein. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments. The terms "comprising," "including," "having," "characterized by," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

Reference throughout this specification to "certain embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics can be combined in any suitable manner, as would be apparent to one of ordinary skill in the art from this disclosure, in one or more embodiments.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A monitor for tracking a fluid bolus, the monitor comprising:
   a display;
   a memory; and
   a processor connected to the display and to the memory, the processor configured to execute instructions that cause the monitor to:
      receive flow signals indicative of flow-related data from a flow probe that is communicatively coupled to the monitor, the flow probe configured to measure fluid flow in a conduit between one or more fluid sources and a patient;
      send a control signal to a flow controller that causes the flow controller to initiate a fluid bolus from one of the one or more fluid sources, the flow controller spatially separated from the flow probe;
      automatically detect initiation of the fluid bolus responsive to the received flow-related data from the flow probe indicating that a flow rate has exceeded a first threshold flow rate value;
      display a prompt on the display indicating that the fluid bolus has started, the prompt including real-time flow-related data received from the flow probe;
      automatically detect termination of the fluid bolus responsive to the received flow-related data from the flow probe indicating that the flow rate has fallen below a second threshold flow rate value;
      determine a total volume of fluid delivered between the initiation of the fluid bolus and the termination of the fluid bolus;
      responsive to the determined total volume of fluid being within a line flush volume range, display a prompt on the display indicating that the fluid bolus is categorized as a line flush; and
      responsive to the determined total volume of fluid exceeding a fluid bolus volume threshold, display a prompt on the display indicating the total volume of fluid delivered and that the fluid bolus is categorized as a fluid bolus.

2. The monitor of claim 1 wherein the processor is further configured to display hemodynamic parameters received from a hemodynamic sensor.

3. The monitor of claim 1 wherein the processor is further configured to receive input based on a user interaction with the prompt instructing the flow controller to terminate the fluid bolus.

4. The monitor of claim 1 wherein the processor is further configured to receive input based on a user interaction with a second prompt discarding the flow-related data determined for the fluid bolus.

5. The monitor of claim 1 wherein the processor is further configured to receive input based on a user interaction with a second prompt accepting the flow-related data determined for the fluid bolus.

6. The monitor of claim 1 wherein the processor is further configured to execute the instructions without receiving input from a user.

7. The monitor of claim 1 wherein the processor is configured to determine that the fluid bolus is desirable based at least in part on measured hemodynamic parameters or flow-related data.

8. The monitor of claim 1 wherein the processor is further configured to determine that a fluid bolus is desirable.

9. The monitor of claim 8 wherein the processor is further configured to display a second prompt on the display indicating that a fluid bolus is suggested.

10. The monitor of claim 1 wherein the processor is further configured to display a second prompt on the display indicating that the fluid bolus has ended, the second prompt including flow-related data determined for the fluid bolus.

11. The monitor of claim 1 wherein the processor is further configured to send a control signal to the flow controller that causes the flow controller to terminate the fluid bolus.

12. The monitor of claim 1 wherein the flow controller is coupled to the conduit between the one or more fluid sources and the patient.

13. The monitor of claim 1 wherein the flow controller includes one or more mechanical components that manipulate the conduit between the one or more fluid sources and the patient.

14. A method for automatically detecting and tracking a fluid bolus, the method comprising:
   receiving, from a flow probe, signals containing flow-related data for fluid flowing in a conduit from one or more fluid sources to a patient;
   sending a control signal to a flow controller that causes the flow controller to initiate a fluid bolus from one of the one or more fluid sources, the flow controller spatially separated from the flow probe;
   detecting initiation of the fluid bolus responsive to the received flow-related data from the flow probe indicating that a flow rate has exceeded a first threshold flow rate value;
   displaying a prompt on a display indicating that the fluid bolus has started, the prompt including real-time flow-related data received from the flow probe;
   detecting termination of the fluid bolus responsive to the received flow-related data from the flow probe indicating that a flow rate has fallen below a second threshold flow rate value;
   determining a total volume of fluid delivered between the initiation of the fluid bolus and the termination of the fluid bolus;
   responsive to the determined total volume of fluid being within a line flush volume range, displaying a prompt on the display indicating that the fluid bolus is categorized as a line flush; and
   responsive to the determined total volume of fluid exceeding a fluid bolus volume threshold, displaying a prompt on the display indicating the total volume of fluid delivered and that the fluid bolus is categorized as a fluid bolus.

15. The method of claim 14 further comprising displaying hemodynamic parameters received from a hemodynamic sensor.

16. The method of claim 14 wherein the method executes without receiving input from a user.

17. The method of claim 14 further comprising determining that a fluid bolus is desirable.

18. The method of claim 17 wherein determining that the fluid bolus is desirable is based at least in part on measured hemodynamic parameters or flow-related data.

19. The method of claim 18 further comprising displaying a second prompt on the display indicating that a fluid bolus is suggested.

20. The method of claim 14 further comprising sending a control signal to the flow controller that causes the flow controller to terminate the fluid bolus.

\* \* \* \* \*